United States Patent
Lu et al.

(10) Patent No.: US 9,880,171 B2
(45) Date of Patent: Jan. 30, 2018

(54) IASPP PHOSPHORYLATION AND METASTATIC POTENTIAL

(71) Applicants: LUDWIG INSTITUTE FOR CANCER RESEARCH LTD., New York, NY (US); THE CHANCELLOR, MASTERS AND SCHOLARS OF THE UNIVERSITY OF OXFORD, Oxford (GB)

(72) Inventors: Xin Lu, London (GB); Min Lu, Oxford (GB)

(73) Assignee: LUDWIG INSTITUTE FOR CANCER RESEARCH LTD., Zurich (CH)

(*) Notice: Subject to any disclaimer, the term of this patent is extended or adjusted under 35 U.S.C. 154(b) by 234 days.

(21) Appl. No.: 14/381,119

(22) PCT Filed: Mar. 1, 2013

(86) PCT No.: PCT/US2013/028696
§ 371 (c)(1),
(2) Date: Aug. 26, 2014

(87) PCT Pub. No.: WO2013/131019
PCT Pub. Date: Sep. 6, 2013

(65) Prior Publication Data
US 2015/0285810 A1  Oct. 8, 2015

Related U.S. Application Data

(60) Provisional application No. 61/711,616, filed on Oct. 9, 2012, provisional application No. 61/606,090, filed on Mar. 2, 2012.

(51) Int. Cl.
| | | |
|---|---|---|
| G01N 33/574 | (2006.01) | |
| C07K 16/18 | (2006.01) | |
| C07K 14/47 | (2006.01) | |
| C07K 16/30 | (2006.01) | |
| C07K 16/44 | (2006.01) | |
| G06F 19/00 | (2011.01) | |
| A61K 39/00 | (2006.01) | |

(52) U.S. Cl.
CPC ... *G01N 33/57496* (2013.01); *C07K 14/4703* (2013.01); *C07K 14/4746* (2013.01); *C07K 16/18* (2013.01); *C07K 16/30* (2013.01); *C07K 16/44* (2013.01); *G06F 19/3431* (2013.01); *A61K 2039/505* (2013.01); *C07K 2317/34* (2013.01); *C07K 2317/76* (2013.01); *G01N 2333/4704* (2013.01); *G01N 2333/4748* (2013.01); *G01N 2440/14* (2013.01); *G01N 2800/56* (2013.01)

(58) Field of Classification Search
None
See application file for complete search history.

(56) References Cited

U.S. PATENT DOCUMENTS

| | | |
|---|---|---|
| 7,645,859 B2 | 1/2010 | Lu et al. |
| 2004/0053262 A1 | 3/2004 | Lu |
| 2004/0228866 A1 | 11/2004 | Lu |
| 2005/0123977 A1 | 6/2005 | Lu |
| 2005/0260629 A1 | 11/2005 | Lu |
| 2006/0100143 A1 | 5/2006 | Lu et al. |
| 2006/0127401 A1 | 6/2006 | Lu |
| 2007/0225240 A1 | 9/2007 | Lu et al. |
| 2008/0193488 A1 | 8/2008 | Lu |
| 2008/0260756 A1 | 10/2008 | Lu et al. |
| 2010/0233171 A1 | 9/2010 | Lu |

FOREIGN PATENT DOCUMENTS

WO   WO-2009/026053 A2   2/2009

OTHER PUBLICATIONS

Danhier et al (International Journal of Pharmaceutics, 2010, vol. 392, pp. 20-28).*
Lu et al (Cancer Cell, 2013, vol. 23, pp. 618-633).*
Avery-Kiejda et al., P53 in human melanoma fails to regulate target genes associated with apoptosis and the cell cycle and may contribute to proliferation, BMC Cancer, 11:203 (2011).
Batycka et al., Ultra-fast tandem mass spectrometry scanning combined with monolithic column liquid chromatography increases throughput in proteomic analysis, Rapid Commun Mass Spectrom, 20(14):2074-2080 (2006).
Bergamaschi et al., iASPP oncoprotein is a key inhibitor of p53 conserved from worm to human, Nature Genetics, 33(2):162-167 (2003).
Breyssens, H., Regulation of iASPP expression by chemotherapeutic drugs, Doctoral Thesis, University of College London, Retrieved from the Internet at: <URL:<http://eprints.ucl.ac.uk/17960/>> (2009).
Chapman et al., Improved survival with vemurafenib in melanoma with BRAF V600E mutation, The New England Journal of Medicine, 364(26):2507-2516 (2011).
Cox et al., The RAF Inhibitor Paradox Revisited, Cancer Cell, 21(2):147-149 (2012).
Curtin et al., Distinct sets of genetic alterations in melanoma, The New England Journal of Medicine, 353(20):2135-2147 (2005).
De Lange et al., Synergistic growth inhibition based on small-molecule p53 activation as treatment for intraocular melanoma, Oncogene, 31(9):1105-1116 (2011).
Emanuel et al., The in vitro and in vivo effects of JNJ-7706621: a dual inhibitor of cyclin-dependent kinases and aurora kinases, Cancer Research, 65(19):9038-9046 (2005).

(Continued)

*Primary Examiner* — Karen Canella
(74) *Attorney, Agent, or Firm* — Marshall, Gerstein & Borun LLP

(57) ABSTRACT

Described herein are methods of evaluating metastatic potential of a cancer based on the phosphorylation state and/or intracellular localization of iASPP. Therapeutic regimens designed based on the results of the diagnostic methods are also provided.

45 Claims, 36 Drawing Sheets

(56) References Cited

OTHER PUBLICATIONS

Fedorov et al., A systematic interaction map of validated kinase inhibitors with Ser/Thr kinases, Proc. Natl. Acad. Sci. U.S.A., 104(51):20523-20528 (2007).
Flaherty, Targeting Metastatic Melanoma. Anu. Rev. Med., 63:171-183 (2011).
Forbes et al., Cosmic 2005, British Journal of Cancer, 94(2):318-322 (2006).
Georgieva et al., Expression of cyclins and cyclin dependent kinases in human benign and malignant melanocytic lesions, Journal of Clinical Pathology, 54(s):229-235 (2001).
Hartn1, "Rabbit anti-iASPP", Retrieved from the Internet at: <URL:<http://tools.invitrogen.com/content/sfs/manuals/409600_Rev1008.pdf> (2010).
Houben et al., High-level expression of wild-type p53 in melanoma cells is frequently associated with inactivity in p53 reporter gene assays, PloS One, 6(7):e22096 (2011).
Hu, Y., A Study on the regulation of iASPP, Doctoral Thesis, University of College London, Retrieved from the Internet at: <URL:<http://eprints.ucl.ac.uk/18527/>> (2009).
International Preliminary Report on Patentability, International Bureau, PCT/US2013/028696, dated Sep. 12, 2014.
International Search Report and Written Opinion, International Searching Authority, PCT/US2013/028696, dated Jul. 26, 2013.
Ji et al., p53 Rescue through HDM2 Antagonism Suppresses Melanoma Growth and Potentiates MEK Inhibition, The Journal of Investigative Dermatology, 132(2):356-364 (2011).
Jiang et al., iASPP and Chemoresistance in Ovarian Cancers: Effects on Paclitaxel-Mediated Mitotic Catastrophe, Clinical Cancer Research, 17(21): 6924-6933 (2011).
Johannessen et al., COT drives resistance to RAF inhibition through MAP kinase pathway reactivation, Nature, 468(7326):968-972 (2010).
Joseph et al., The RAF inhibitor PLX4032 inhibits ERK signaling and tumor cell proliferation in a V600E BRAF-selective manner, Proc. Natl. Acad. Sci. U.S.A., 107(33):14903-14908 (2010).
Kamath et al., Proteomic databases and tools to decipher post-translational modifications, Journal of Proteomics, 75(1):127-144 (2011).
Liu et al., Elevated expression of iASPP in head and neck squamous cell carcinoma and its clinical significance, Medical Oncology, 29(5): 3381-3388 (2012).
Lu et al., Restoring p53 Function in Human Melanoma Cells by Inhibiting MDM2 and Cyclin B1/CDK1-Phosphorylated Nuclear iASPP, Cancer Cell, 25(5): 618-633 (2013).
Muthusamy et al., Amplification of CDK4 and MDM2 in malignant melanoma, Genes Chromosomes & Cancer, 45(5):447-454 (2006).
Nazarian et al., Melanomas acquire resistance to B-RAF(V600E) inhibition by RTK or N-RAS upregulation, Nature, 468(7326):973-977 (2010).
Notari et al., Inhibitor of apoptosis-stimulating protein of p53 (iASPP) prevents senescence and is required for epithelial stratification, Proc. Natl. Acad. Sci. U.S.A., 108(40):16645-16650 (2011).
Polsky et al., HDM2 protein overexpression and prognosis in primary malignant melanoma, Journal of the National Cancer Institute, 94(23):1803-1806 (2002).
Polsky et al., HDM2 protein overexpression, but not gene amplification, is related to tumorigenesis of cutaneous melanoma, Cancer Research, 61(20):7642-7646 (2001).
Poulikakos et al., Mutant BRAF melanomas—dependence and resistance, Cancer Cell, 19(1):11-15 (2011).
Poulikakos et al., RAF inhibitor resistance is mediated by dimerization of aberrantly spliced BRAF(V600E), Nature, 480(7377):387-390 (2011).
Poulikakos et al., Resistance to MEK inhibitors: should we co-target upstream?, Science Signaling, 4(166):pe16 (2011).
Robinson et al., Biochemical and structural studies of ASPP proteins reveal differential binding to p53, p63, and p73, Structure, 16(2):259-268 (2008).

Sachdev et al., Nuclear localization of IkappaB alpha is mediated by the second ankyrin repeat: the IkappaB alpha ankyrin repeats define a novel class of cis-acting nuclear import sequences, Molecular and Cellular Biology, 18(5):2524-2534 (1998).
Samuels-Lev et al., ASPP proteins specifically stimulate the apoptotic function of p53, Molecular Cell, (4)8:781-794 (2001).
Schittek et al., The increased expression of Y box-binding protein 1 in melanoma stimulates proliferation and tumor invasion, antagonizes apoptosis and enhances chemoresistance, International Journal of Cancer, 120(10):2110-2118 (2007).
Slee et al., The N-terminus of a novel isoform of human iASPP is required for its cytoplasmic localization, Oncogene, 23(56):9007-9016 (2004).
Song et al., Overexpression of cyclin B1 in human esophageal squamous cell carcinoma cells induces tumor cell invasive growth and metastasis, Carcinogenesis, 29(2):307-315 (2008).
Tseng et al., Contrasting effects of nutlin-3 on TRAIL- and docetaxel-induced apoptosis due to upregulation of TRAIL-R2 and Mcl-1 in human melanoma cells, Molecular Cancer Therapeutics, 9(12):3363-3374 (2010).
Van Impe et al., A new role for nuclear transport factor 2 and Ran: nuclear import of CapG, Traffic, 9(5):695-707 (2008).
Yang et al., Identification of a novel inhibitor of nuclear factor-kappaB, RelA-associated inhibitor, The Journal of Biological Chemistry, 274(22):15662-1567 (1999).
Breyssens, "Regulation of iASPP expression by chemotherapeutic drugs," Doctoral Thesis, University College London, Ludwig Institute for Cancer Research, and University of Oxford (2009).
Ying Hu, "A Study on the Regulation of iASPP," Doctoral Thesis, Ludwig Institute for Cancer Research, University of Oxford, and University College London (2009).
Al-Hillawi, et al., "Phosphorylation-specific antibodies for human cardiac troponin-I," Eur. J. Biochem. 256, 535-540 (1998).
Bartkova, et al. "ATM Activation in Normal Human Tissues and Testicular Cancer," Cell Cycle, 4:838-845 (Jun. 2005).
Blaydes, et al., "The Development and Use of Phospho-Specific Antibodies to study Protein Phosphorylation," Methods in Molecular Biology, vol. 99, pp. 177-189 (2000).
Brown, et al., "PDGF-Receptor Activation Induces p120-Catenin Phosphorylation at Serine 879 via a PKCα-Dependent Pathway," Exp Cell Res.315:39-49 (Jan. 1, 2009).
*Blue Calypso, LLC* v. *Groupon, Inc.*, (Fed. Cir. 2015-1396, decided Mar. 1, 2016).
Dopfer, et al. "Analysis of novel phosphor-ITAM specific antibodies in a S2 reconstitution system for TCR-CD3 signalling," Imm. Letters 130:43-50 (2010).
Emanuel, et al., "The In vitro and In vivo Effects of JNJ-7706621: A Dual Inhibitor of Cyclin-Dependent Kinases and Aurora Kinases," Cancer Res; 62:19, pp. 9038-9046 (Oct. 1, 2005).
Fedorov, et al., "A systematic interaction map of validated kinase inhibitors with Ser/Thr kinases," PNAS, vol. 104, No. 51, pp. 20523-20528 (Dec. 18, 2007).
Neumann et al., "Phosphorylation of S409/410 of TDP-43 is a consistent feature in all sporadic and familial forms of TDP-43 proteinopathies," Acta Neuropathol., 117:137-149 (2009).
Pollok-Kopp, et al., "Dynamics of protein kinase C-mediated phosphorylation of the complement C5a receptor on serine 334," J. Biol. Chem. 282(7): 4345-53 (Feb. 16, 2006). Abstract Only.
Stephan et al., "Ionizing radiation-dependent and independent phosphorylation of the 32-kDa subunit of replication protein a during mitosis," Nucleic Acids Res., 37:6028-41 (2009).
Vaughan, et al., "Generation and characterization of a novel phospho-specific monoclonal antibody to p120-catenin serine 879," Hybridoma, 26(6):407-15 (Dec. 2007). Abstract Only.
Vielemeyer, et al., "Direct Selection of Monoclonal Phosphospecific Antibodies without Prior Phosphoamino Acid Mapping," J. Biol. Chem., 284:20791-20795 (2009).
Zafrullah et al., "Kinase Suppressor of Ras Transphosphorylates c-Raf-1," Biochem. Biophys. Res. Commun., 390:434-440 (2009).

* cited by examiner

FIGURE 2B
Table 1

| Origin | Cell lines | Ratio of slow-migrating iASPP | iASPP localization |
|---|---|---|---|
| Melanoma | SK-MEL23 | ++++ | N |
| | SK-MEL37 | + | N + C |
| | WM115 | ++++ | N |
| | WM278 | ++ | N + C |
| | IGR37 | ++++ | N |
| | IGR39 | ++ | N + C |
| | 501-MEL | ++ | N + C |
| | Me300 | ++ | N + C |

Ratio of slow-migrating iASPP:
 + 0-20%, ++ 20-50%, +++ 50-80%, ++++ 80-100%.

iASPP localization:
 N predominantly nuclear, C predominantly cytoplasmic, N + C relatively equal

| Origin | Cell lines | Ratio of slow-migrating iASPP | iASPP localization |
|---|---|---|---|
| Gastrointestin | GIST480 | + | C |
| | GIST882 | + | C |
| Osteosarcoma | U2OS | + | C |
| | Saos-2 | + | C |
| Epithelium | HaCaT | + | C |
| | A431 | + | C |
| Breast | MCF-7 | + | C |
| Renal | XK1 | + | C |
| | SK RC12 | + | C |
| | SK RC12 | + | C |
| | RCC4 | + | C |
| Lung | H1299 | + | C |
| | NCL-H727 | + | C |
| | SHP-77 | + | C |
| Testis | TERA-1 | + | C |
| | TERA-2 | + | C |
| Leukaemia | THP-1 | + | C |
| | HMC-1 | + | C |

- THP-1 = immature normal human macrophages derived from peripheral blood of leukemic patient
- HMC-1 = immature normal human mast cells derived from leukemic patient

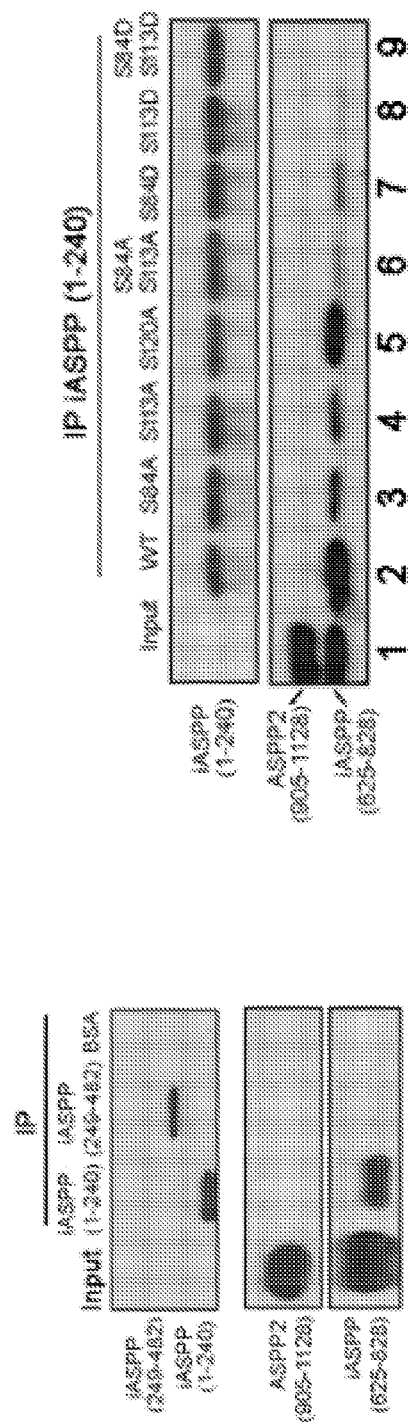
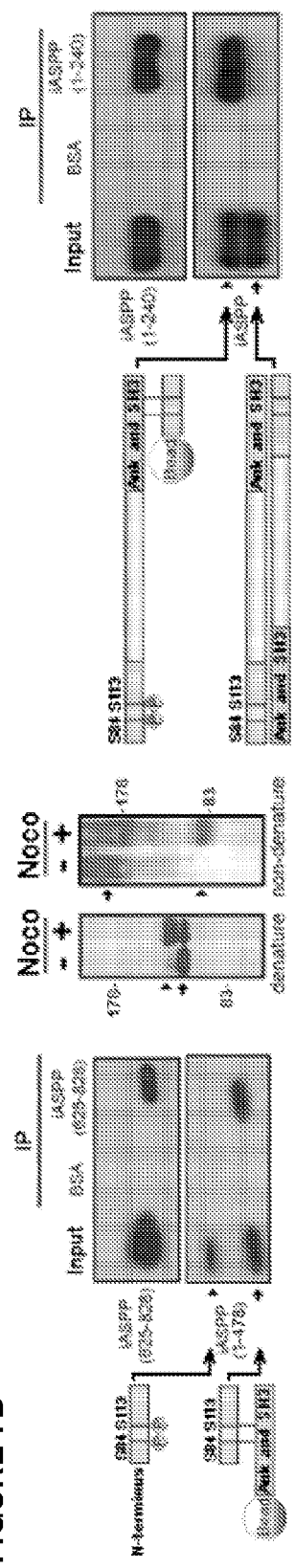
FIGURE 7A
FIGURE 7B

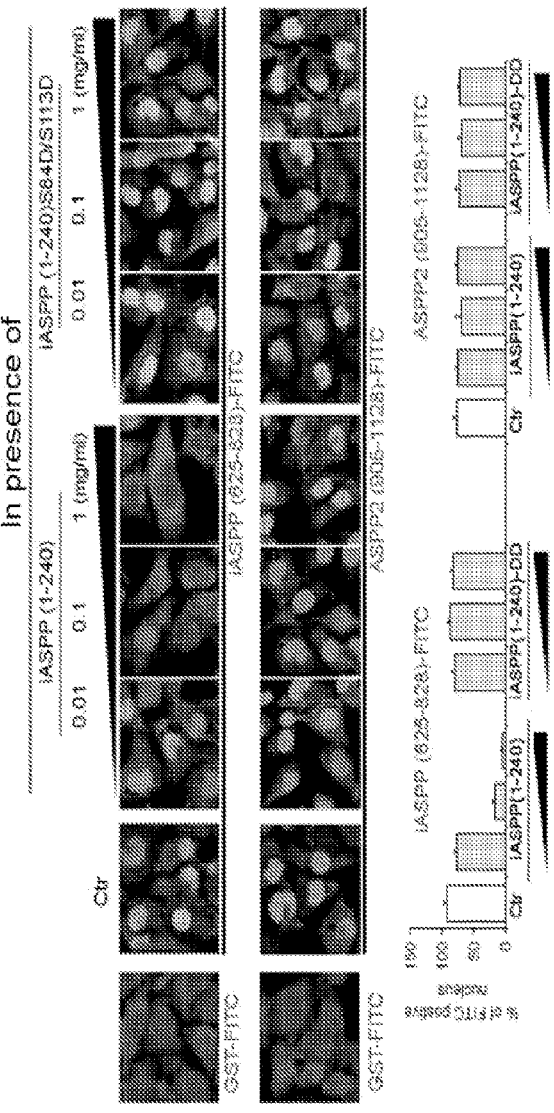
FIGURE 7E
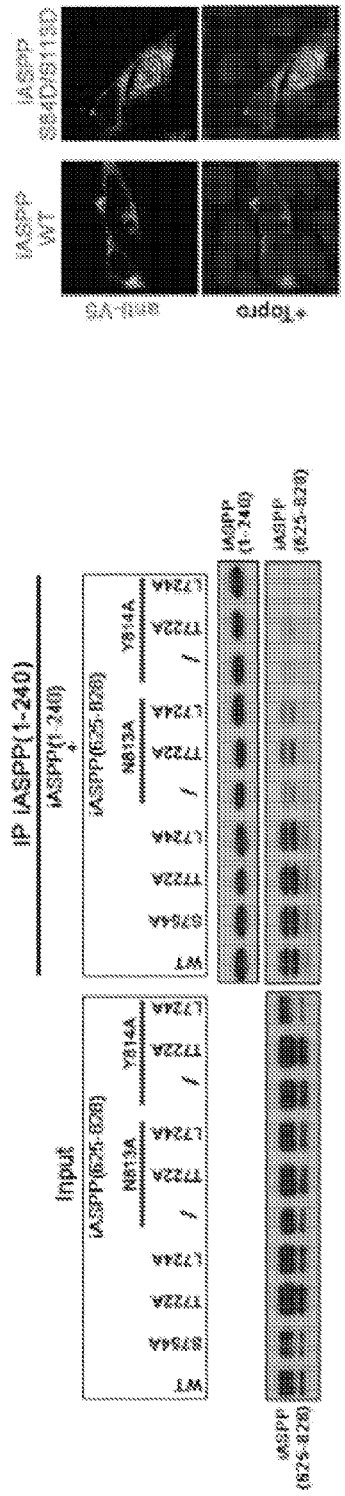
FIGURE 7C
FIGURE 7D

Table 2

| SGC ID | target(s) | modification block | |
|---|---|---|---|
| | | 10 µM | 2 µM |
| K00590a | Aurora | - | - |
| K00603a | Aurora | - | - |
| K00625a | Aurora | - | - |
| K00861a | Plk1 | - | - |
| K00972a | Pim1 | - | - |
| K00778a | Pim1 | - | - |
| K01742a | Pim1 | - | - |
| K00500 | Pim1 | - | - |
| K00616a | CDKs, Aurora | + | + |
| K00020 | CDKs | - | - |

K00016a: JNJ-7706621, IC50 for CylinB/cdk1 = 9nm;
K00020: Roscovitine, IC50 for CylinB/cdk1 = 650 nm;
K00014: Purvalanol A, IC50 for CylinB/cdk1 = 4 nm.

| SGC ID | target(s) | modification block | |
|---|---|---|---|
| | | 10 µM | 2 µM |
| K00750a | CDKs, Clk, dirk1 | + | - |
| K00518 | Clk, Dyrk1 | + | - |
| K00969a | Clk1 | + | - |
| K01874a | Clk1 | ± | - |
| K00014 | CDKs | ± | - |
| K00935a | Mps1 | + | - |
| K00936a | Mps1, Plk1? | - | - |
| K00964a | FAK, Mps1 | + | - |

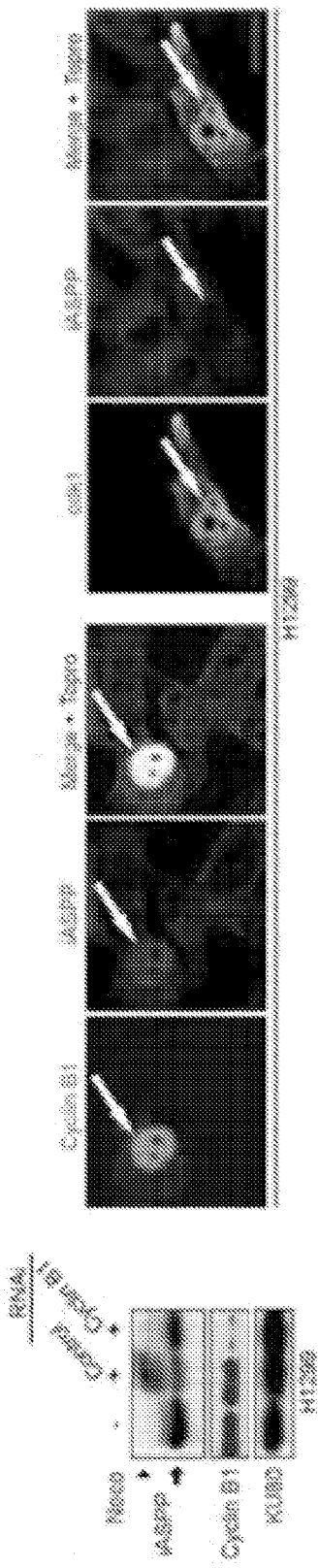
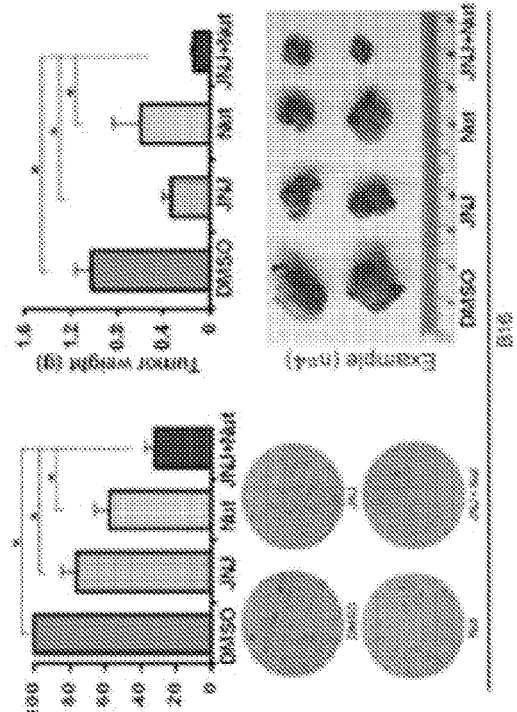
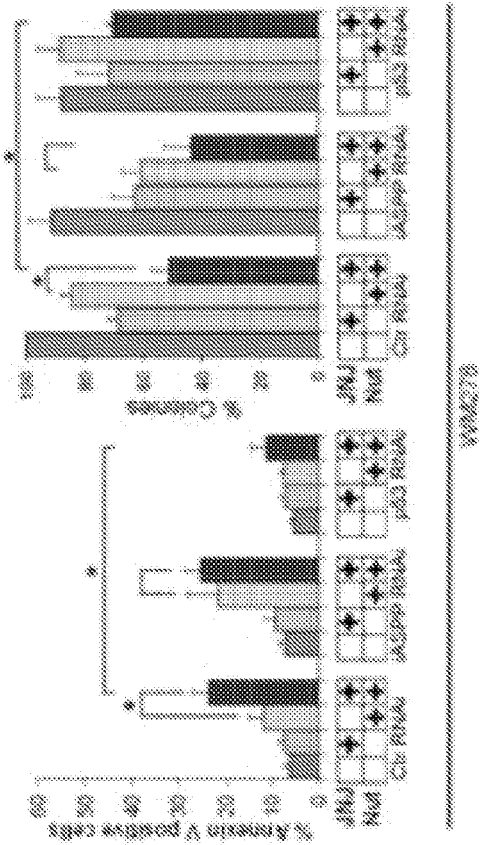
FIGURE 19A
FIGURE 19B
FIGURE 19C

FIGURE 20A

Table 2

| Compound description (name) | target(s) | Block effect | |
|---|---|---|---|
| | | 10 µM | 2 µM |
| JNJ-7706621 | CDK1m Aurora | +++ | +++ |
| Aurora Kinase Inhibitor II | Aurora | - | - |
| Aurora Kinase Inhibitor III | Aurora | - | - |
| VX680 | Aurora | - | - |
| PLK inhibitor I | Plk1 | - | - |
| Pim1 inhib IV | Pim1 | - | - |
| Pim1 Inhib II | Pim1 | + | - |
| KH-CARB10 | Pim1 | + | - |
| RO-3308 | CDK1 | +++ | + |
| 229_0254_4145 | Clk1, Dyrk1 | +++ | + |
| KH-C15A | Clk1 | +++ | + |
| KH-CB19T | Clk1 | ++ | + |
| Purvalanol A | CDKs | ++ | + |
| 229_0242_0168 | Pim1 | - | - |
| Roscovitine | CDK2 | + | - |

Block effect: +++ very effective; ++ effective, ; weakly effective, - negative

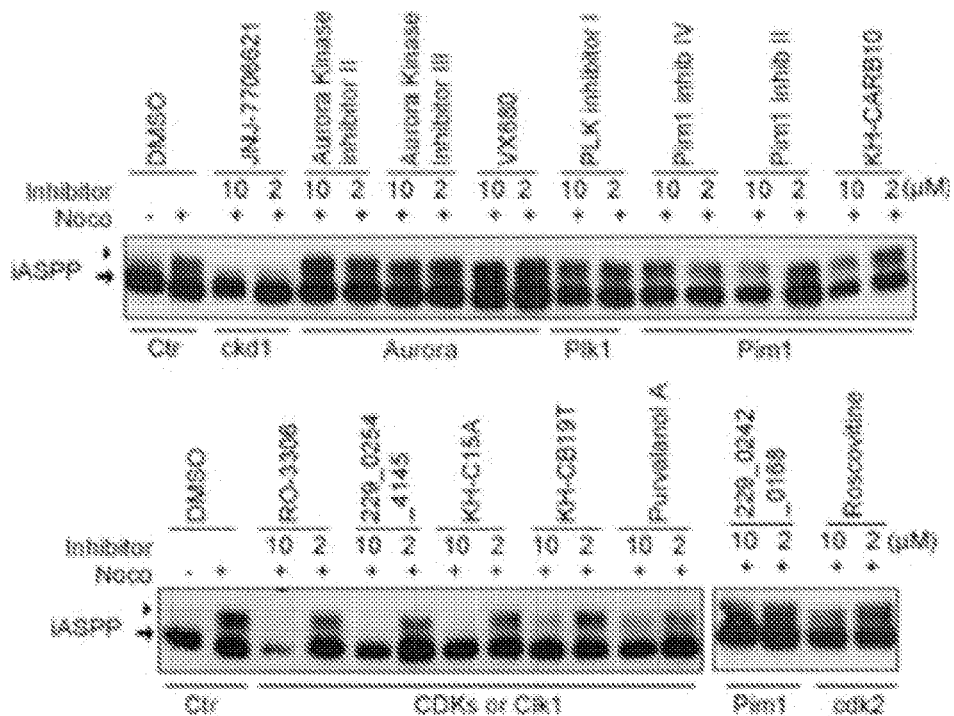

IASPP PHOSPHORYLATION AND METASTATIC POTENTIAL

BACKGROUND OF THE INVENTION

Melanoma is the most lethal skin tumour, and its incidence is rising. Metastatic melanoma is refractory to treatment and is associated with a very poor prognosis. Advanced/metastatic melanoma frequently harbours mutations in the RAS-BRAF-MAPK oncogene and in the p16ink4A-Rb and p14Arf-p53 tumour suppressor pathways. Around 20% and 44% of melanomas harbor active mutations of N-RAS and B-RAF, respectively, and these tumours have elevated RAS/RAF kinase activities (Forbes et al., 2006). Similarly, deletion in the p16ink4A locus, which will inactivate both p16ink4a and p14Arf, also occurs in around 50% of melanomas (Curtin et al., 2005). P16ink4a is an inhibitor of cyclin dependent kinases, cyclinD1/cdk4 in particular. Melanomas containing p16ink4a mutations will have elevated cyclinD1/cdk4 kinase activity that will in turn phosphorylate the tumour suppressor Rb and inactivate its ability to arrest the cell at G1 phase of the cell cycle. Mutation of p14Arf will remove its ability to block the action of mdm2, an inhibitor and E3 ubiquitin ligase of p53. As a result, p14Arf mutant melanoma cells may have wild type p53, but its tumour suppressive functions are lost. The importance of RAS-RAF oncogene and p16ink4a/Rb and p14Arf/p53 tumour suppressor pathways in the development and maintenance of melanomas is underscored by a plethora of experimental evidence. This knowledge has led to the recent success of B-RAF inhibitors, such as PLX4032, as new melanoma therapeutic agents. PLX4032 selectively inhibits proliferation of tumour cells that harbour the B-RafV600E mutation (Joseph et al., 2010). Despite promising efficacy in inhibiting melanoma growth in the initial stages of treatment, the majority of PLX4032 treated patients relapsed within a few months, largely due to acquired drug resistance. As expected, the majority of the drug resistance was caused by mutations affecting the RAS/MAPK pathways (Chapman et al., 2011; Cox and Der, 2012; Johannessen et al., 2010; Nazarian et al., 2010; Poulikakos and Rosen, 2011; Poulikakos and Solit, 2011). (Chapman et al., 2011; Johannessen et al., 2010; Nazarian et al., 2010). To overcome acquired drug resistance, co-targeting B-RAFV600E and MEK has been suggested (Poulikakos 2011). As both B-RAF and MEK are in the same pathway, it is difficult to predict whether targeting these two components of the same pathway will be sufficient to eliminate all melanoma cells. An alternative strategy would be to induce synthetic lethality of melanoma cells by co-targeting two independent pathways that are both critical in melanoma development and maintenance.

The tumor suppressor p53 pathway is of particular interest. B-RAFV600E is present in around 50% of human melanomas; however, 80% of human melanomas express wild type p53 implying that a large number of B-RAFV600E melanomas also contain wild type p53. It has been established that growth suppression induced by B-RAFV600E inhibitors is independent of p53. It is also known that the tumor suppressive function of p53 is largely lost in melanoma cells expressing wild type p53 expressing tumors.

Overexpression of mdm2 or and mdmX are two inhibitors of p53, has been observed in melanomas, and this was shown to contribute to the inactivation of wild type p53 function (Muthusamy et al., 2006; Polsky et al., 2001). To restore the tumor suppressive function of p53 in human tumors, including melanomas that express wild type p53, agonists of p53 such as Nutlin3 have been developed and tested in Phase II clinical trials. Nutlin3 suppresses tumor growth by inducing cell cycle arrest through it ability to prevent mdm2 from targeting p53 for degradation. Unfortunately, nutlin3 failed to reactivate p53 in all wild type p53-expressing melanoma cells (de Lange et al., 2011; Ji et al., 2011). It is therefore important to identify an alternative strategy for reactivating the tumor suppressing function of p53 in melanoma cells.

A need exists for modulators of apoptosis. For example, pro-apoptotic modulators may be useful for treating or palliating cancers or other conditions characterized by undesirable or uncontrolled cell growth. Anti-apoptotic factors may be useful for treating or palliating degenerative conditions.

SUMMARY OF THE INVENTION

The present invention has numerous aspects and is based in part on discoveries described herein involving iASPP molecular and cell biology, including discoveries including iASPP phosphorylation, iASPP intracellular localization, the effect of iASPP phosphorylation and location of metastasis of a cancer cell and other insights.

In one aspect of the invention, a method of evaluating metastatic potential of a cancer is provided. In some variations, the method comprises (a) measuring phosphorylation state and/or intracellular localization of inhibitory Apoptosis-Stimulating Protein of p53 (iASPP) in a cancer cell from a mammalian subject, and (b) diagnosing (or evaluating or scoring) metastatic potential of the cancer based on the phosphorylation state and/or intracellular localization of iASPP in the cancer cell measured according to step (a). In some embodiments, the methods comprises measuring phosphorylation state and/or intracellular localization of iASPP in a plurality of cancer cells from the mammalian subject, and diagnosing metastatic potential of the cancer based on an average measurement from the plurality of the cells, or from a percentage of the cells that exceed a cutoff or reference measurement. The diagnosing of metastatic potential is optionally made from the percentage of total iASPP that is phosphorylated or the percentage of total iASPP that is localized in the nucleus of the cell.

Without intending to limit the invention to any particular theory, it appears that iASPP phosphorylation and iASPP localization to the nucleus are biologically related, and both phenomena are useful—if not interchangeable—indicators of the metastatic potential of a cancer. Therefore, if an aspect of the invention is described in the context of iASPP phosphorylation, the invention should be understood to include a related embodiment involving iASPP intracellular localization, and vice versa. For brevity, not all aspects have been described in duplicate with respect to these phenomena.

In any of the methods described herein, the mammalian subject is preferably human. Coding and deduced amino acid sequences for a wild type human iASPP are set forth in SEQ ID NO: 1 and 2, respectively.

In some embodiments, the cancer cell is from a primary tumor from the subject. For example, the cell(s) may be obtained from a biopsy, of following tumor resection from a patient.

The diagnostic methods described herein optionally comprise screening the cancer cell for at least one parameter selected from the group consisting of: a p53 mutation that reduces a tumor suppressive function of p53, an elevated measurement of mdm2 protein or mRNA, and a B-RafV600E mutation; and diagnosing metastatic potential of the cancer based on the phosphorylation state and/or intracellular localization of iASPP in the cancer cell and from the presence or absence of the at least one parameter. In some embodiments, the at least one parameter comprises the p53 mutation that reduces a tumor suppressive function of p53.

The data collected relating to these parameters has relevance to the selection of a course of therapy for the subject with the cancer, as described in greater detail below. Methods that include prescribing or administering a therapy based on the data obtained with respect to these parameters also is an aspect of the invention.

The measuring of phosphorylated iASPP can occur after a cancer diagnosis has been made and prior to in initiation of a standard of care cancer therapy (e.g., chemotherapy). In some embodiments, the measuring of phosphorylated iASPP occurs after a cancer has become resistant to a standard of care therapy (e.g., chemotherapy). These embodiments are not mutually exclusive. A subject undergoing cancer therapy can be monitored for phosphorylated iASPP expression to identify a time point at which phosphorylated iASPP becomes elevated and therapy with a cdk1 inhibitor is indicated according to the invention.

In some embodiments, measuring of the phosphorylation state comprises at least one of: an analytical technique that provides an absolute measure of phosphorylated iASPP; an analytical technique that provides a relative measure of phophorylated iASPP to total iASPP in the cell; and an analytical technique that provides a relative measure of phosphorylated iASPP to unphosphorylated iASPP in the cell.

To assess the relative level of phosphorylated iASPP expression, the level of phosphorylated iASPP expression in a cancer tissue sample can be subjected to one or more of various comparisons. In general, it can be compared to: (a) phosphorylated iASPP expression level(s) in normal tissue from the organ in which the cancer originated; (b) phosphorylated iASPP expression level(s) in a collection of comparable cancer tissue samples; (c) phosphorylated iASPP expression level(s) in a collection of normal tissue samples; or (d) phosphorylated iASPP expression level(s) in an arbitrary standard. In some embodiments, the screening methods described herein comprises comparing the expression of phosphorylated iASPP in the tumor (or vessel tissue or tumor fluid) to the level of phosphorylated iASPP expression in healthy tissue of the same type as the tumor, wherein elevated phosphorylated iASPP expression in the tumor (or vessel tissue or tumor fluid) to compared to the healthy tissue identifies the metastatic potential of the cancer.

In some embodiments, the measuring comprises measuring the phosphorylation state of iASPP in the cancer cell, wherein the phosphorylation is serine phosphorylation at an iASPP serine residue corresponding to serine 84 (Ser84) and/or serine 113 (Ser113) in the human iASPP amino acid sequence of SEQ ID NO: 2.

The measuring step of the methods described herein optionally comprises comparing the measurement of phosphorylated iASPP to a reference measurement of phosphorylated iASPP, and scoring the phosphorylated iASPP measurement from the sample as elevated based on statistical analysis or a ratio relative to the reference measurement. In some embodiments, the reference measurement comprises at least one of the following (a) a measurement of phosphorylated iASPP from healthy tissue of the subject of the same tissue type as the sample; (b) a database containing multiple phosphorylated iASPP measurements from healthy or cancerous tissues from other subjects; or (c) a reference value calculated from multiple phosphorylated iASPP measurements from healthy or cancerous tissues from other subjects, optionally further including statistical distribution information for the multiple measurements, such as standard deviation.

In some embodiments, a phosphorylated iASPP measurement of at least 1.0 standard deviation greater than a median phosphorylated iASPP measurement in corresponding healthy tissue is scored as elevated phosphorylated expression. In other embodiments, a phosphorylated measurement that is statistically significantly greater than phosphorylated iASPP measurements in corresponding healthy tissue, with a p-value less than 0.1 is scored as elevated phosphorylated iASPP expression.

In some variations, the level of phosphorylated iASPP in a subject is compared to a predetermined "cut-off" concentration of phosphorylated iASPP that has been determined from observations to represent an elevated measure of phosphorylated iASPP that (when equaled or exceeded) is predictive of metastatic potential in the cancer. Determination of a suitable cut-off is made using, e.g., statistical analysis of phosphorylated iASPP concentration data collected from multiple healthy and/or cancer patients. If a "cut-off" value is employed, the cut-off concentration preferably is statistically determined to have optimal discriminating value to identify cancer with metastatic potential. It will be appreciated that statistical analysis of a dataset will permit clinicians to make informed decisions based on concentrations other than the optimal discriminating concentration (e.g., above or below the optimal discriminating concentration). For example, using receiver-operating-characteristic curves, or using other statistical summaries of phosphorylated iASPP concentration and metastases outcome data collected according to the invention, the practitioner is capable of selecting a cut-off phosphorylated iASPP concentration having a desired level of sensitivity or specificity for predicting the metastatic potential of the cancer.

The output or conclusion from methods as described here are not limited to binary classification of tumors having (or not having) metastatic potential. Cancers can be stratified into two, three, four, five, or more categories of metastatic risk potential, based on the measurement of iASPP phosphorylation (or iASPP intracellular localization). For example, the percent of total iASPP that is phosphorylated, or localized to the nucleus, can be used to stratify the cancers.

A variety of techniques can be used to measure iASPP, and to measure iASPP phosphorylation or intracellular localization, and all such techniques are contemplated for practicing the invention.

The diagnostic methods described herein optionally comprises contacting the cancer cell, or protein isolated from the cancer cell, with a binding partner that specifically binds phosphorylated iASPP, and measuring the phosphorylation state of iASPP by measuring the amount of the binding partner-iASPP complex formed. In some embodiments, the binding partner comprises a detectable label. In some embodiments, the diagnostic methods comprise contacting the cancer cell, or protein isolated from the cancer cell, with a first binding partner and a second binding partner, wherein the first binding partner binds iASPP and the second binding partner specifically binds the phosphorylated iASPP, wherein the second binding partner comprises a detectable label, and measuring the phosphorylation state of iASPP by measuring the amount of second binding partner-iASPP complex formed. The phosphorylated iASPP recognized by the second binding partner optionally comprises one or more phosphorylated serine residues. In some embodiments, the serine residues are selected from the group consisting of Ser84 and Ser113. In some embodiments, the first binding partner is an antibody that binds to an epitope comprising all or part of, or contained within, amino acids 501-510 of SEQ ID NO: 2 and the second binding partner is an antibody that binds to an epitope comprising all or part of, or contained within, amino acids 107-118 of SEQ ID NO: 2, wherein the amino acid at position 113 of SEQ ID NO: 2 in the epitope is phosphorylated.

In some embodiments, the diagnostic methods comprise contacting the cancer cell, or protein isolated from the cancer cell, with a first binding partner and a second binding partner that binds iASPP, wherein the first binding partner binds phosphorylated and unphosphorylated iASPP, and wherein the second binding partner binds an epitope of iASPP that includes Ser84 or Ser113 of iASPP (SEQ ID NO: 2) and selectively binds iASPP when said serine in said epitope is unphosphorylated, and wherein the second binding partner comprises a detectable label, and measuring the phosphorylation state of iASPP by measuring the amount of second binding partner-iASPP complex formed. In some embodiments, the first binding partner is an antibody that binds to an epitope comprising all or part of, or contained within, amino acids 501-510 of SEQ ID NO: 2 and the second binding partner is an antibody that binds to an epitope comprising all or part of, or contained within, amino acids 111-122 of SEQ ID NO: 2.

In some embodiments, the diagnostic methods comprise measuring total iASPP in a cell. For example, in some embodiments, the method comprises measuring total iASPP in the cell, and measuring unphosphorylated iASPP in the cell, wherein a difference between total iASPP and unphosphorylated iASP provides an indication of the amount of phosphorylated iASPP in the cell. The method optionally comprises measuring unphosphorylated iASPP in the cell comprises contacting the cancer cell, or protein isolated from the cancer cell, with a binding partner that preferentially binds iASPP in which one or more serine residues selected from serine 84 (Ser84, SEQ ID NO: 2) and serine 113 (Ser113, SEQ ID NO: 2) is not phosphorylated. An exemplary antibody that recognizes an unphosphorylated epitope is antibody LX128.5.

Measuring iASPP phosphorylation in a cell comprises, in some embodiments, contacting the cancer cell, or protein isolated from the cancer cell, with a binding partner that preferentially binds iASPP in which one or more serine residues selected from serine 84 (Ser84, SEQ ID NO: 2) and serine 113 (Ser113, SEQ ID NO: 2) is phosphorylated, and measuring the phosphorylation state of iASPP by measuring the amount of polypeptide-binding partner complex formed, to provide a measure of iASPP that is phosphorylated at one or more of the serine residues. In such embodiments, the binding partner is an antibody that preferentially recognizes an iASPP epitope in which one or more serine residues selected from serine 84 (Ser84, SEQ ID NO: 2) and serine 113 (Ser113, SEQ ID NO: 2) is phosphorylated, compared to epitopes of iASPP in which Ser84 and Ser113 are unphosphorylated. In some embodiments, the binding is measured in situ in a tumor biopsy.

In another aspect, described herein is a method of measuring iASPP phosphorylation state in a cancer cell from a mammalian subject, wherein the method comprises contacting the cancer cell, or a sample derived from the cancer cell (such as a cell lysate or cellular fraction, or protein isolated from the cancer cell, with a binding partner that specifically binds phosphorylated iASPP, and measuring the phosphorylation state of iASPP by measuring the amount of the binding partner-iASPP complex formed. In some embodiments, the binding partner comprises a detectable label. In some embodiments, the assaying method comprises contacting the cancer cell, or the sample derived from the cell, or the protein isolated from the cancer cell, with a first binding partner and a second binding partner, wherein the first binding partner binds iASPP and the second binding partner specifically binds the phosphorylated iASPP, wherein the second binding partner comprises a detectable label, and measuring the phosphorylation state of iASPP by measuring the amount of second binding partner-iASPP complex formed (e.g., using a procedure that includes measuring the detectable label). The phosphorylated iASPP recognized by the second binding partner optionally comprises one or more phosphorylated serine residues. In some embodiments, the serine residues are selected from the group consisting of Ser84 and Ser113. In some embodiments, the first binding partner is an antibody that binds to an epitope comprising all or part of, or contained within, amino acids 501-510 of SEQ ID NO: 2 and the second binding partner is an antibody that binds to an epitope comprising all or part of, or contained within, amino acids 107-118 of SEQ ID NO: 2, wherein the amino acid at position 113 of SEQ ID NO: 2 is phosphorylated in the epitope.

In some embodiments, the assaying methods comprise contacting the cancer cell, or a biological sample derived from the cancer cell (such as a cell lysate or subcellular fraction, or protein isolated from the cancer cell, with a first binding partner and a second binding partner that binds iASPP, wherein the first binding partner binds phosphorylated and unphosphorylated iASPP, and wherein the second binding partner binds an epitope of iASPP that includes Ser84 or Ser113 of iASPP (SEQ ID NO: 2) and selectively binds iASPP when said serine in said epitope is unphosphorylated, and wherein the second binding partner comprises a detectable label, and measuring the phosphorylation state of iASPP by measuring the amount of second binding partner-iASPP complex formed. In some embodiments, the first binding partner is an antibody that binds to an epitope comprising all or part of, or is contained within, amino acids 501-510 of SEQ ID NO: 2 and the second binding partner is an antibody that binds to an epitope comprising all or part of, or is contained within, amino acids 111-122 of SEQ ID NO: 2.

The diagnostic or assaying methods described herein optionally include a separation step to determine a measurement of phosphorylated iASPP in a sample. In such embodiments, the measuring comprises separating phosphorylated and unphosphorylated iASPP, and measuring iASPP phosphorylation by measuring the amounts of separated phosphorylated and unphosphorylated iASPP. The separating can be performed by any means known in the art, such as gel electrophoresis. In some embodiments, the measuring comprises isolating iASPP from the cancer cell, and measuring phosphorylated serine in the isolated iASPP.

The diagnostic or assaying methods described herein optionally comprise the step of making a communication that includes metastatic potential of the cancer based on the phosphorylation state and/or intracellular localization of iASPP in the cancer cell available to the individual or to a third party. In some embodiments, the communication is made available to the individual or third party by a secured internet interface. Exemplary third party include, but are not limited to a physician or another health care worker, or an insurer or health care payer government or private entity.

As described herein and depicted in figures, phosphorylated iASPP appears to migrate at a different speed in gel electrophoresis. Thus, in some variations, the measurement of amounts of fast- and slow-migrating forms of iASPP is used as a tool for measuring the amount of iASPP phosphorylation from a cell or cell lysate. This can be accomplished, for example, by gel electrophoresis and western blotting.

In various embodiments, the diagnosing comprises comparing the amount of phosphorylated iASPP in the cancer cell with a measurement of phosphorylated iASPP from healthy cells of the same type as the cancer cell, wherein increased iASPP phosphorylation in the cancer cell indicates that the cancer is at increased risk for metastases. In some embodiments, the diagnosing comprises comparing the percentage of iASPP that is phosphorylated in the cancer cell with a calculation of the percentage of iASPP that is phosphorylated in a healthy cell of the same type as the cancer cell, wherein increased percentage of phosphorylated iASPP in the cancer cell indicates that the cancer is at increased risk for metastases.

In various embodiments, the iASPP polypeptide or the binding partner is attached to a solid support, and binding is detected by detecting a complex between the polypeptide and the binding partner on the solid support. The binding partner optionally comprises a detectable label, and wherein binding is detected by detecting the label in a complex between the iASPP polypeptide and the binding partner.

The diagnostic methods, in various embodiments, comprise measuring intracellular localization of iASPP in the cancer cell, wherein the measuring comprises at least one of an analytical technique that provides an absolute measure of iASPP in the nucleus of the cancer cell, an analytical technique that provides a relative measure of iASPP in the nucleus to total iASPP in the cell, and an analytical technique that provides a relative measure of iASPP in the nucleus to iASPP in the cytoplasm of the cell. In some embodiments, the method comprises comparing the measure of iASPP in the nucleus of the cancer cell with a measure of iASPP in a healthy cell of the same type as the cancer cell, wherein increased iASPP in the nucleus of the cancer cell compared to the healthy cells indicates an increased metastatic potential for the cancer.

Measuring intracellular localization of iASPP can be performed by methods known in the art, such as immunohistochemistry. For example, the intracellular localization of iASPP can be measured by immunohistochemical staining of the cancer cell with an antibody that specifically binds iASPP. In some embodiments, the measuring further comprises contacting the cancer cell with a nucleus-specific marker.

For any of the diagnostic methods described herein, repeating the measuring steps is specifically contemplated. For example, in some embodiments, the method comprises repeating the measuring in a plurality of cancer cells from the subject, wherein an increased percentage of cancer cells with phosphorylated iASPP or nuclear-localized iASPP indicates an increased metastatic potential for the cancer.

In various embodiments, the diagnostic methods further comprise measuring the mitotic index of the cancer.

Any available technique can be used for measuring phosphorylated iASPP expression, including direct and indirect techniques. Exemplary techniques for measuring amounts or concentrations of phosphorylated iASPP in a sample are immunological techniques that involve use of a polyclonal or monoclonal antibody that specifically binds phosphorylated iASPP, or use of a phosphorylated iASPP-binding fragment of such an antibody. For example, the measuring comprises contacting the biological sample with a iASPP antibody that preferentially binds a phosphorylated form of iASPP or antigen-binding fragment thereof. Quantification of the amount of bound antibody (e.g., using a label or second, labeled antibody) provides a measurement of phosphorylated iASPP expressed in the sample. The use of immunoassays such as radioimmunoassay, immunoradiometric assay (labeled antibody), or an enzyme-linked immunosorbant assay (ELISA) are contemplated.

The screening methods described herein may optionally comprise the step of prescribing for or administering to the subject identified as having elevated phosphorylated iASPP expression in the biological sample a composition comprising a molecule that suppresses expression or phosphorylation activity of cyclinB1/cdk1. Data presented herein implicate cyclinB1/cdk1 as a kinase responsible for phosphorylation of iASPP. The human cDNA and deduced amino acid sequences for this enzyme are set forth in Genbank Accession No. NM_001786 and Swiss/Prot Accession Nos. P06943, respectively.

Another aspect of the invention is an iASPP binding partner selected from the group consisting of (a) antibody that specifically binds iASPP polypeptide and preferentially binds to iASPP having a phosphorylated serine compared to binding to iASPP without the phosphorylated serine, wherein said serine residue corresponds to a serine selected from the group consisting of Ser84 and Ser113 of the human iASPP amino acid sequence of SEQ ID NO: 2; (b) a fragment of (a) that specifically binds iASPP polypeptide and preferentially binds to iASPP having the phosphorylated serine; and (c) a polypeptide that comprises (b) and that specifically binds iASPP polypeptide and preferentially binds to iASPP having the phosphorylated serine. The binding partner optionally binds to an epitope of the phosphorylated peptide comprising a portion of amino acids 81-130 of SEQ ID NO: 2, wherein one or both of the serine residues as positions 84 and 113 of SEQ ID NO: 2 are phosphorylated. In some embodiments, the binding partner binds to an epitope of the phosphorylated peptide comprising all or part (some) of amino acids 107-118 of SEQ ID NO: 2, wherein the serine at position 113 of SEQ ID NO: 2 is phosphorylated.

In some embodiments, the binding partner is an antibody or antibody fragment. In some embodiments, the antibody or antibody fragment (including, but not limited to, Fab, Fab', F(ab')2, ScFv and Fv fragments) does not bind to unphosphorylated iASPP.

Also provided is an iASPP binding partner selected from the group consisting of (a) antibody that specifically binds iASPP polypeptide and preferentially binds to iASPP having an unphosphorylated serine compared to binding to iASPP with the phosphorylated serine, wherein said serine residue corresponds to a serine selected from the group consisting of Ser84 and Ser113 of the human iASPP amino acid sequence of SEQ ID NO: 2; (b) a fragment of (a) that specifically binds iASPP polypeptide and preferentially binds to iASPP having the unphosphorylated serine; and (c) a polypeptide that comprises (b) and that specifically binds iASPP polypeptide and preferentially binds to iASPP having the unphosphorylated serine. In some embodiments, the iASPP binding partner binds to an epitope of the unphosphorylated iASPP that comprises all or some of, or is contained within amino acids 111-122 of SEQ ID NO: 2. Antibody LX128.5 is an exemplary antibody that preferentially recognizes an epitope of the N-terminus of unphosphorylated iASPP.

Another aspect is a kit comprising a first antibody that recognizes an iASPP polypeptide having at least one phosphorylated serine residue selected from the group consisting of Ser84 and Ser113 and optionally a second antibody that binds to iASPP at an epitope distinct from that recognized by the first antibody. The first antibody, in some embodiments, binds to an epitope comprising all or some of amino acids 107-118 of SEQ ID NO: 2, wherein the serine at position 113 of SEQ ID NO: 2 is phosphorylated in the epitope. In some embodiments, the second antibody binds phosphorylated and unphosphorylated iASPP. The second antibody, in some embodiments, binds to an epitope comprising all or some of amino acids 501-510 of SEQ ID NO: 2. In some embodiments, the kit further comprises a nucleus specific marker.

Another aspect is a kit comprising a first antibody and a second antibody, wherein the first antibody recognizes an iASPP polypeptide and the second antibody binds an epitope of iASPP that includes Ser84 or Ser113 of iASPP (SEQ ID NO: 2) and selectively binds iASPP when said serine in said epitope is unphosphorylated, and wherein the second antibody optionally comprises a detectable label, such as a radioisotope or a fluorophor or an enzyme or enzyme substrate. In some embodiments, the second antibody binds to iASPP at an epitope distinct from that recognized by the first antibody. In some embodiments, the first antibody binds to an epitope comprising all or some of amino acids 501-510 of SEQ ID NO: 2 and the second antibody binds to an epitope comprising all or some of amino acids 111-122 of SEQ ID NO: 2. The kit optionally comprises a nucleus-specific marker.

In some variations, iASPP binding partners described herein are antibodies (including antibody fragments and engineered antibody molecules). For example, the invention includes:

A. An antibody that specifically binds to an epitope of human iASPP (SEQ ID NO: 2), wherein the epitope includes a serine of the iASPP at position 84 or 113 of SEQ ID NO: 2, and wherein the antibody preferentially or selectively or specifically binds the iASPP when the serine in the epitope is unphosphorylated.

A1. The antibody according to paragraph A that comprises a monoclonal antibody or comprises an antigen-binding fragment thereof.

A2. The antibody according to paragraph A or A1 that further comprises a detectable label.

A3. The antibody according to any one of paragraphs A-A2, wherein the epitope includes the serine at position 84 of SEQ ID NO: 2 (Ser84).

A4. The antibody according to paragraph A or A1, wherein the epitope includes the serine at position 113 of SEQ ID NO: 2 (Ser113).

A5. The antibody according to paragraph A4, wherein the epitope comprises or is contained within amino acids 107-118 of SEQ ID NO: 2.

A6. A composition comprising the antibody according to any one of paragraphs A-A4 that is substantially free of antibody that binds the iASPP when the serine is phosphorylated.

A7. The composition according to paragraph A6 that includes the antibody that binds to the epitope that includes Ser84 and the antibody that binds to the epitope that includes Ser113.

In related variations, the invention includes:

B. An antibody that specifically binds to an epitope of human iASPP (SEQ ID NO: 2), wherein the epitope includes a serine of the iASPP at position 84 or 113 of SEQ ID NO: 2, and wherein the antibody preferentially or selectively or specifically binds the iASPP when the serine in the epitope is phosphorylated.

B1. The antibody according to paragraph B that comprises a monoclonal antibody or comprises an antigen-binding fragment thereof.

B2. The antibody according to paragraph B or B1 that further comprises a detectable label.

B3. The antibody according to any one of paragraphs B-B2, wherein the epitope includes the serine at position 84 of SEQ ID NO: 2 (Ser84), wherein the serine is phosphorylated.

B4. The antibody according to paragraph B or B1, wherein the epitope includes the serine at position 113 of SEQ ID NO: 2 (Ser113), wherein the serine is phosphorylated.

B5. The antibody according to paragraph B4, wherein the epitope comprises or is contained within amino acids 107-118 of SEQ ID NO: 2, wherein the serine is phosphorylated.

B6. A composition comprising the antibody according to any one of paragraphs B-B4 that is substantially free of antibody that binds the iASPP when the serine is unphosphorylated.

B7. The composition according to paragraph B6 that includes the antibody that binds to the epitope that includes phosphorylated Ser84 and the antibody that binds to the epitope that includes phosphyrlated Ser113.

As described elsewhere herein, the invention includes kits in which iASPP binding partners are packaged with each other and/or with other reagents that are useful together for evaluating iASPP phosphorylation status. For example the invention includes:

C. A kit containing the antibody or composition according to any one of paragraphs A-A7 and B-B7.

C1. The kit according to paragraph C that further includes a capture antibody that binds an epitope of human iASPP that is present in the iASPP irrespective of whether the serines at positions 84 and 113 are phosphorylated.

C2. The kit according to paragraph C1, wherein the capture antibody binds an epitope of iASPP that comprises or is contained within amino acids 501-510 of SEQ ID NO: 2.

C3. The kit according to paragraph C1 or C2, wherein the capture antibody is bound to a solid support.

C4. The kit according to any one of paragraphs C to C3 that includes an antibody according to any one of paragraphs A-A7 and an antibody according to any one of paragraphs B-B7.

C5. The kit according to any one of paragraphs C to C3 that includes the antibody according to paragraph A3 and the antibody according to paragraph A4 or A5.

C6. The kit according to any one of paragraphs C to C3 and C5 that includes the antibody according to paragraph B3 and the antibody according to paragraph B4 or B5.

C7. The kit according to any one of paragraphs C to C6 further comprising one or more compositions selected from wash reagents, detecting reagents useful for detecting and/or measuring a bound antibody (especially measuring a labeled antibody bound to its target); and a cell nucleus-specific marker.

C8. The kit according to any one of paragraphs C to C7 wherein the elements are packaged together but not in admixture.

The iASPP phosphorylation assays described herein are themselves an aspect of the invention. As taught in detail herein, the results of such assays can be used by the party performing the assays, or a third party, to evaluate cancer status of a subject and for selection, monitoring, and changing treatment approaches. Likewise, the results of such assays are useful in a laboratory and research context for characterizing cancer cell lines, monitoring changes in cancer cell lines, and evaluating therapeutic compound candidates against cancer cell lines having different iASPP phosphorylation characteristics. Thus, aspects of the invention include iASPP phosphorylation assays such as the following:

D. A method of measuring a phosphorylation state of iASPP comprising: contacting iASPP protein with the antibody or composition according to any one of paragraphs A-A6 and B-B6, and measuring the amount of antibody that is bound to the iASPP or measuring the amount of antibody-iASPP complex.

D1. The method according to paragraph D, wherein the iASPP is in a biological sample, and the method comprises contacting the biological sample with the antibody or composition.

D2. The method according to paragraph D1, wherein the biological sample is from a cancer cell or a tumor from a mammalian subject.

D3. The method according to any one of paragraphs D1-D2, further comprising measuring the total iASPP in the sample.

D4. The method according to paragraph D3, further comprising comparing the measurement of total iASPP with the measurement of phosphorylated iASPP and/or the measurement of unphosphorylated iASPP to derive a measurement of the percentage of total iASPP that is phosphorylated or unphosphorylated.

D5. The method according to any one of paragraphs D2-D4, comprising repeating the method using a biological sample from a non-cancerous cell or tissue of the same tissue type as the cancer cell or the tumor, and comparing the measures of iASPP phosphorylation in the cancer versus non-cancerous cells.

D6. The method according to any one of paragraphs D-D5, comprising performing the measuring repeatedly with a plurality of cancer cells from the mammalian subject and generating an average measurement of other statistical analysis from the repeated measurements.

D7. The method according to any one of paragraphs D-D5, comprising performing the measuring with a lysate from a plurality of cancer cells from the mammalian subject.

D8. The method according to any one of paragraphs D1 to D7, further comprising screening the cancer cells for evidence of a p53 mutation.

Inhibitor peptides are also considered an aspect of the invention. For example, in some embodiments, the inhibitor peptide is an isolated peptide that comprises an amino acid sequence selected from the group consisting of (a) a fragment of the iASPP amino acid sequence set forth in SEQ ID NO: 2, wherein the fragment binds to a kinase that phosphorylates iASPP at a serine residue selected from the group consisting of Ser84 and Ser113 of SEQ ID NO: 2; (b) an analog of (a) wherein from 1-10 amino acids have been deleted, inserted, or replaced with different amino acids, wherein said analog binds to the kinase that phosphorylates iASPP at a serine residue selected from the group consisting of Ser84 and Ser113 of SEQ ID NO: 2; (c) a cyclized version of (a) or (b) that binds to the kinase that phosphorylates iASPP at a serine residue selected from the group consisting of Ser84 and Ser113 of SEQ ID NO: 2; wherein the peptide binds to the kinase that phosphorylates iASPP at a serine residue selected from the group consisting of Ser84 and Ser113 of SEQ ID NO: 2, and wherein the peptide inhibits the kinase from phosphorylating iASPP. In some embodiments, the kinase is cyclinB1/cdk1.

In some embodiments, the isolated peptide comprises an amino acid sequence that is at least 90% identical to the amino acid sequence set forth in SEQ ID NO: 2 or a fragment thereof, wherein the peptide binds to a kinase that phosphorylates iASPP at a serine residues selected from the group consisting of Ser84 and Ser113 of SEQ ID NO: 2 and wherein the peptide inhibits the kinase from phosphorylation of the serine residue. In some embodiments, the peptide variants of the invention do not include S84D or S113D mutations. Data presented herein shows that iASPP with these mutations mimics phosphorylated wildtype iASPP.

In some embodiments, the isolated peptide comprises a fragment of SEQ ID NO: 2 that optionally includes or consists of amino acids 1-240 of SEQ ID NO: 2 or amino acids 81-130 of SEQ ID NO: 2 or amino acids 107-118 of SEQ ID NO: 2.

Also provided is an isolated peptide that comprises an amino acid sequence at least 95% or more identical to amino acids 1-240 of SEQ ID NO: 2, or a fragment thereof that inhibits translocation of iASPP into the nucleus of a cancer cell. In some embodiments, the peptide variants of the invention do not include S84D or S113D mutations. Data presented herein shows that iASPP with these mutations mimics phosphorylated wildtype iASPP.

A composition comprising any of the isolated peptides described herein and a pharmaceutically acceptable carrier are also contemplated.

Another aspect of the invention is a method of treating a subject with cancer. For example, a method of the invention comprises administering to a subject with cancer an agent that inhibits cdk1 phosphorylation of iASPP. In some variations, the administering step is preceded by a diagnostic step or method as described herein, that identifies the subject as having a cancer with elevated metastatic potential due to iASPP phosphorylation or iASPP nuclear localization.

Aspects of the invention that are described herein as methods (especially methods that involve treatment) can alternatively be described as (medical) uses of reagents or therapeutics. For example, in one variation, the invention is a use of a composition that comprises a molecule that suppresses expression or activity of cdk1 for the treatment of cancer in a subject identified with cancer and identified with elevated phosphorylated iASPP expression in the cancer (wherein the subject is identified as having elevated phosphorylated iASPP expression in the cancer by a method described herein).

In the treatment methods (or uses) described herein, the methods optionally comprises administering a standard or care therapeutic to the subject in combination with the cdk1 inhibitor. With respect to any combination treatment or therapy regimens described herein, the cdk1 inhibitor composition can be administered simultaneously with the other active agents, which may be in admixture with the cdk1 inhibitor, or may be in a separate composition. Each composition preferably includes a pharmaceutically acceptable diluent, adjuvant, or carrier. When the agents are separately administered, they may be administered in any order.

In another aspect, disclosed herein is a therapeutic regimen for treating a cancer in a mammalian subject, the method comprising: (a) measuring phosphorylation state and/or intracellular localization of inhibitory Apoptosis-Stimulating Protein of p53 (iASPP) in a cancer cell from a mammalian subject, (b) screening the cancer cell for at least one parameter selected from the group consisting of: a p53 mutation that reduces a tumor suppressive function of p53, an elevated measurement of mdm2 protein or mRNA, and a B-RafV600E mutation; and (c) prescribing and/or administering a therapeutic regimen that includes an inhibitor of iASPP phosphorylation for a subject with a cancer characterized by elevated iASPP phosphorylation and/or iASPP nuclear localization. In some embodiments, the therapeutic regimen comprises prescribing and/or administering a therapeutic regimen that includes an inhibitor of iASPP phosphorylation and an inhibitor of mdm2-induced degradation of p53, for a subject with a cancer characterized by elevated iASPP phosphorylation and/or iASPP nuclear localization and the absence of a p53 mutation that reduces the tumor suppressive function of p53. (The presence of a wild type p53 is scored as the absence of a p53 mutation that reduces tumor suppressive function of p53.) The therapeutic regimen optionally comprises prescribing and/or administering a therapeutic regimen that includes an inhibitor of iASPP phosphorylation and an inhibitor B-RafV600E, for a subject with a cancer characterized by elevated iASPP phosphorylation and/or iASPP nuclear localization and the presence of the B-Raf-V600E mutation.

In some embodiments, the inhibitor of iASPP phosphorylation is an inhibitor of cyclin B1/cdk1, such as K00616a or JNJ-7706621. The inhibitor of mdm2-induced degradation of p53 is optionally Nutlin3, and the inhibitor of B-RafV600E is optionally GDC-0879, PLX-4720, Sorafenib, Tosylate Vemurafenib (also known as PLX4032, RG7204 or RO5185426, marketed as Zelboraf™).

The therapeutic regimen optionally comprises prescribing a standard-of-care therapy to a mammalian subject in whom elevated iASPP phosphorylation and/or elevated iASPP nuclear localization is absent from the cancer cell.

In some variations, the invention is simply the treatment steps without first determining the phosphorylation state of iASPP in a cancer cell of a mammalian subject.

The invention includes use of measurement of a phosphorylation state and/or intracellular localization of inhibitory Apoptosis-Stimulating Protein of p53 (iASPP) in a cancer cell from a mammalian subject for assessing the metastatic potential of the cancer and/oe selection of a therapeutic regimen. Such a use optionally comprises use of a measurement of at least one parameter selected from the group consisting of: a p53 mutation that reduces a tumor suppressive function of p53, an elevated measurement of mdm2 protein or mRNA, and a B-RafV600E mutation; for the selection of a therapeutic regimen for the mammalian subject. In some embodiments, the therapeutic regimen includes an inhibitor of iASPP phosphorylation for a subject with a cancer characterized by elevated iASPP phosphorylation and/or iASPP nuclear localization, and optionally wherein the therapeutic regimen further includes an inhibitor of mdm2-induced degradation of p53, for a subject with a cancer characterized by elevated iASPP phosphorylation and/or iASPP nuclear localization and the absence of a p53 mutation that reduces the tumor suppressive function of p53, and an inhibitor B-RafV600E, for a subject with a cancer characterized by elevated iASPP phosphorylation and/or iASPP nuclear localization and the presence of the B-Raf-V600E mutation.

Another aspect of the invention is a system for identifying metastatic potential of a cancer in a human subject, the system comprising (a) at least one processor; (b) at least one computer-readable medium; (c) a database operatively coupled to a computer-readable medium of the system and containing population information correlating the phosphorylation state or intracellular localization of iASPP in cancer and metastasis data in a population of humans; (d) a measurement tool that receives an input about the human subject and generates information from the input about the iASPP phosphorylation or iASPP intracellular localization in a cancer cell from the human subject; and (e) an analysis tool or routine that: (i) is operatively coupled to the database and the measurement tool, (ii) is stored on a computer-readable medium of the system, (iii) is adapted to be executed on a processor of the system, to compare the information about the human subject with the population information in the susceptibility database and generate a conclusion with respect to susceptibility to metastatic potential of the cancer in the human subject.

In some embodiments, the database optionally includes population information correlating the presence or absence of a p53 mutation that reduces a tumor suppressive function of p53 and metastasis data in the population of humans, wherein the measurement tool further generates information from the input about the presence or absence of a p53 mutation in the cancer cell from the human subject that reduces a tumor suppressive function of p53, and wherein the analysis tool generates a conclusion with respect to susceptibility to metastatic potential of the cancer in the human subject using both information about the phosphorylation state or intracellular localization of iASPP and the information about the p53 mutation.

As described below in detail, some variations of a system of the invention include a medical protocol database operatively connected to a computer-readable medium of the system and containing information correlating iASPP phosphorylation state (and any of the one or more additional parameters described herein) and medical protocols for treating human subjects with cancer. Such a system further includes a medical protocol tool or routine to compare or correlate the conclusion obtain from the analysis routine and the medical protocol database, and generate a protocol report with respect to the probability that one or more medical protocols will achieve a therapeutic goal, or a protocol report assessing the relative merits of different protocols for the subject's cancer.

The invention also includes compounds, compositions, methods, and systems for treatment of cancers.

Also provided is a composition comprising an inhibitor of cyclin B1/cdk1-induced phosphorylation of iASPP and a pharmaceutically acceptable carrier. The composition optionally further comprises an inhibitor of mdm2-induced degradation of p53. In some embodiments, the composition further comprises an inhibitor of B-RafV600E.

Another aspect of the invention is a unit dose comprising an inhibitor of cyclin B1/cdk1-induced phosphorylation of iASPP; an inhibitor of mdm2-induced degradation of p53; and an inhibitor B-RafV600E; wherein the inhibitors are packaged together, and at least two of the inhibitors are not in admixture. In some embodiments, the three inhibitors are not in admixture.

Yet another aspect is a method of treating a mammalian subject with cancer, wherein the method comprises administering to the subject an inhibitor of cyclin B1/cdk1-induced phosphorylation of iASPP; an inhibitor of mdm2-induced degradation of p53; and an inhibitor B-RafV600E; wherein the inhibitors are administered in amounts effective to inhibit proliferation of the cancer. In some embodiments, the inhibitors are optionally administered in amounts effective to induce death of cancer cells in the mammalian subject.

Aspects of the invention that are described herein as methods (especially methods that involve treatment) can alternatively be described as (medical) uses of reagents or therapeutics. For example, in one variation, the invention is a use of a composition that comprises a molecule that suppresses expression or activity of cdk1 for the treatment of cancer in a subject identified with cancer and identified with elevated phosphorylated iASPP expression in the cancer (wherein the subject is identified as having elevated phosphorylated iASPP expression in the cancer by a method described herein).

In the treatment methods (or uses) described herein, the methods optionally comprises administering a standard or care therapeutic to the subject in combination with the inhibitor of cyclin B1/cdk1-induced phosphorylation of iASPP; an inhibitor of mdm2-induced degradation of p53; and/or an inhibitor B-RafV600E. With respect to any combination treatment or therapy regimens described herein, the cdk1 inhibitor composition can be administered simultaneously with the other active agents, which may be in admixture with the inhibitor of cyclin B1/cdk1-induced phosphorylation of iASPP; an inhibitor of mdm2-induced degradation of p53; and/or inhibitor B-RafV600E, or may be in a separate composition. Each composition preferably includes a pharmaceutically acceptable diluent, adjuvant, or carrier. When the agents are separately administered, they may be administered in any order.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicant(s) by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE FIGURES

FIG. 2 is a summary of iASPP (slow versus fast migrating forms) and cellular localization in the various cancer cell lines that were examined.

FIG. 7. S84/S113 phosphorylation of iASPP prevents N- and C-terminal self-interaction and promotes iASPP nuclear localization. A. N- and C-terminal iASPP self-interacts, and iASPP(1-240 of SEQ ID NO: 2)S84D/S113D fails to interact with C-terminal iASPP in vitro. Upper panel: 10 µg/ml purified GST-tagged iASPP (1-240 of SEQ ID NO: 2) or iASPP (249-482 of SEQ ID NO: 2) were incubated with 10 µg/ml purified 6*His-tagged iASPP (625-828 of SEQ ID NO: 2) or ASPP2 (905-1128 of SEQ ID NO: 2) in NP40 buffer for 2 hours. iASPP (1-240 of SEQ ID NO: 2) and iASPP (249-482 of SEQ ID NO: 2) were pulled down by glutathione beads. Bound iASPP (625-828 of SEQ ID NO: 2) and ASPP2 (905-1128 of SEQ ID NO: 2) were determined using anti-His antibodies. Lower panel: 10 µg/ml purified iASPP (1-240 of SEQ ID BO: 2)-GST mutants were incubated with 10 µg/ml mixture of iASPP (625-828 of SEQ ID NO: 2)-His and ASPP2 (905-1128 of SEQ ID NO: 2)-His in NP40 buffer for 2 hours. Interaction was determined as above. B. Modification of iASPP abrogates N- and C-terminus self interaction and changes iASPP molecule conformation. Upper left panel: iASPP(1-478 of SEQ ID NO: 2)-V5 was overexpressed in iASPP (−/−) MEFs and a slow-migrating expression pattern was induced by nocodazole treatment. Cells were suspended in NP40 buffer, and interactions between overexpressed iASPP(1-478 of SEQ ID NO: 2)-V5 and purified iASPP(625-828 of SEQ ID NO: 2)-His were determined by co-immunoprecipitation. Cartoon figure shows the scheme of selectively binding between unmodified iASPP(1-478 of SEQ ID NO: 2) and iASPP (625-828 of SEQ ID NO: 2). Lower panel: endogenous iASPP in H1299 showed a slow-migrating pattern of expression after nocodazole treatment. Cells were suspended in NP40 buffer, and interaction between endogenous iASPP and iASPP (1-240 of SEQ ID NO: 2)-GST was determined by co-immunoprecipitation. Cartoon figure shows the scheme of selective binding between modified iASPP and iASPP(1-240 of SEQ ID NO: 2). Upper right panel: H1299 cells were treated with or without nocodazole and iASPP mobility shift were determined in non-denaturing or denaturing WB. C. N-terminal iASPP binds N813 and Y814 of C-terminal iASPP (SEQ ID NO: 2). 20 µl iASPP (1-240 of SEQ ID NO: 2)-GST pre-bound glutathione beads were incubated with 3 µl in vitro translated iASPP (625-828 of SEQ ID NO: 2)-V5 mutants in NP40 buffer. After 4 washes, the interaction between them was determined by co-immunoprecipitation using anti-GST and anti-V5 antibodies. D. N-terminal iASPP prevents nuclear translocation of C-terminal iASPP in vitro. Purified iASPP (625-828 of SEQ ID NO: 2) was labeled with FITC and incubated with digitonin treated H1299 cells in presence of 0-1 mg/ml iASPP (1-240 of SEQ ID NO: 2). Nuclear iASPP (625-828 of SEQ ID NO: 2)-FITC was determined by direct FITC fluorescence. iASPP(1-240)S84D/S113D and ASPP2(905-1128 of SEQ ID NO: 2) were used as control. Parallel experiments were done for all protein samples, and representative images were shown. Bar=20 µm. Lower bar graph shows the percentage of FITC positive nucleus after treatment from 3 experiments. >100 cells were counted. E. iASPP S84D/S113D shows stronger nuclear staining than wild type iASPP in iASPP(−/−) MEFs. iASPP-V5 mutants were stably expressed in iASPP(−/−) MEFs; cellular localization was determined by V5 antibody. Bar=20 µm.

FIG. 10. Ser84/Ser113-phosphorylated nuclear iASPP is enriched in wild type p53 expressing metastatic tumor. In FIG. 10C, the arrow head shows the position of the slow-migrating iASPP isoform while the arrow shows the fast-migrating isoform.

FIG. 11.

FIG. 12. Restoring the tumour suppressive function of p53 and inhibiting BRAFV600E causes synthetic suppression of melanoma cells.

FIG. 13.

FIG. 18. S84/S113 phosphorylated nuclear iASPP is enriched in wild type p53 expressing melanoma cells.

FIG. 19. Restoring p53 by inhibiting mdm2 and iASPP suppresses melanoma growth in vitro and in vivo. FIG. 19A. Upper left panel: H1299 cells were treated with control (Ctr) or cyclin B1 RNAi to knock down cyclin B1 in the presence (+) or absence (−) of 10 μM nocodazole. Upper right panel: double immunofluorescence staining shows colocalization of nuclear cyclin B1/ASPP, but not cdk1/iASPP. H1299 cells expressing transfected cyclinB1 or cdk1 are labeled by white arrows. Bar=20 μm. Lower left panel: H1299 cells were co-treated with 10 μM nocodazole and various mitosis related kinase inhibitors overnight. Lower right panel: WM278 cells were treated with DMSO, 0.4 μM JNJ-7706621 (an inhibitor of cyclin B1/CDK1, also referred to herein as "JNJ"), or 10 μM nocodazole overnight, and were lysated and incubated with (+) or without (−) calf intestinal phosphatase (CIP) for 1 hour, followed by p53 co-immunoprecipitation. Arrows and arrow heads mark the positions of the fast or slow-migrating iASPP isoforms respectively. FIG. 19B. WM278 cells were pre-treated with 0.4 μM JNJ for 48 hours to block iASPP modification. Cells were then treated with 0.4 μM JNJ, 20 μM Nutlin3 or a combination as indicated for another 72 hours in the presence or absence of control, iASPP, and p53 RNAi as indicated. The left bar graph shows the percentage of Annexin V positive cells and the right bar graph shows the percentage of treated cells that formed colonies. Bars (from left to right) in both bar graphs correspond to cells treated with DMSO, JNJ, Nut and JNJ+Nut, respectively. The number of colonies formed in DMSO treated cells were set as 100%. The bar graphs (mean±SD) were derived from three independent experiments. *p<0.05. FIG. 19C. In vitro treatment of JNJ+Nutlin3, as described herein above, suppresses B16 melanoma cell growth in vitro (left panel, colony assay) and in vivo (right panel, xenograft model). Bar graphs are shown as mean±SD (*p<0.05, n=4 for each group). Lower panel shows representative dishes and isolated tumors, respectively.

FIG. 20. Restoring p53 by inhibiting mdm2 and iASPP suppresses melanoma growth in vitro and in vivo. FIG. 20A. H1299 cells were treated with DMSO or 10 μM nocodazole in the presence or absence of 2 or 10 μM of mitosis-related kinase inhibitors as indicated. Table 2 within FIG. 20A shows the efficacy of mitotic kinase inhibitors to reduce iASPP modification, which ranged from very effective (+++), to effective (++), and to weakly effective (+). Those which failed to affect iASPP mobility shift are labeled as negative (−).

FIG. 22. Restoring the apoptotic function of p53 cooperates with BRAFV600E inhibition to suppress human melanoma cell growth.

DETAILED DESCRIPTION

Figure 1A:
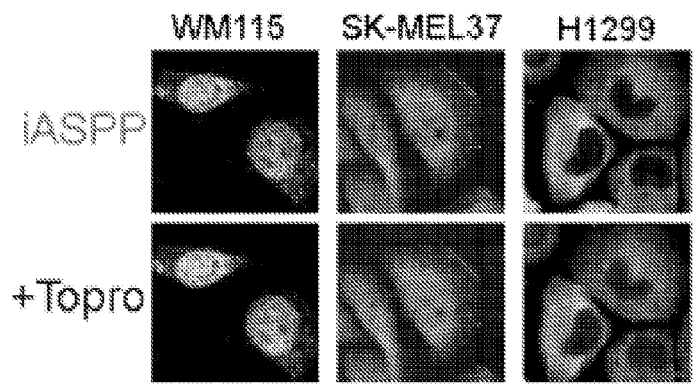
FIG. 1. Nuclear iASPP is associated with the appearance of a slow-migrating iASPP isoform that preferentially binds p53 in vivo. A. iASPP staining and nucleus specific marker staining (Topro) in melanoma and H1299 cells shows distinct cytoplasmic and nuclear localization. Melanoma (WM115 and SRK-MEL37) and H1299 cells were seeded on cover slides and immunofluorescence stained by iASPP antibody LX49.3. Bar=20 μm. B. iASPP expression pattern in a panel of melanoma cell lines. Total cell lysate was prepared in UREA buffer, and iASPP patterns were determined by iASPP antibody LX49.3. C. p53 prefers to bind to the slow-migrating iASPP isoform in melanoma. Melanoma cell lysate was prepared in NP40 buffer, and p53 antibody (Do-1) was applied to co-immunoprecipitate iASPP (if any) bound to p53, followed by iASPP determination by antibody LX49.3.

The ASPP family (Apoptotic-Stimulating Proteins of p53) is newly identified as a family of p53 interacting proteins which includes members that may contribute to site selectivity by enhancing the activation of apoptotic rather than growth arrest target genes. This finding indicates that the ASPP family cooperates with p53, and plays an important role in controlling the decision between life and death.

Three members, ASPP1, ASPP2 and iASPP have been identified in the family (Bergamaschi et al., 2004; Bergamaschi et al., 2003). All members contain ankyrin repeats, an SH3 domain and a proline-rich domain in their carboxyl terminus. This conserved C-terminus sequence involves the most important binding sites with the partners identified so far (Trigiante and Lu, 2006). The N terminus of iASPP has no homology with ASPP1 and ASPP2. The sequence similarities among the ASPP family members indicate that ASPP1 and ASPP2 probably have similar biological functions that differ from that of iASPP. Indeed, existing studies have demonstrated that ASPP1 and ASPP2 are specific pro-apoptotic regulators of p53 (Samuels-Lev et al., 2001); while iASPP is an inhibitor and antagonizes ASPP1 and ASPP2 function (Bergamaschi et al., 2003). Importantly, iASPP is the only member existing in *C. elegans*, which indicates that iASPP is an evolutionarily conserved inhibitor of p53.

It was recently reported that iASPP inhibits cellular senescence in vitro and epithelium stratification in vivo (Notari et al., 2011). iASPP is predominantly expressed as nuclear protein in basal epithelium that also co-expresses p63, a proliferative compartment of epidermis. iASPP migrates to the cytoplasm in differentiated epithelial cells, and cellular location of iASPP must therefore play a crucial role in controlling its function upon epithelium differentiation. Since many of the proteins with which iASPP interacts are transcription factors, including p53, p63 and p65Nfkb, it is likely that nuclear iASPP is more active than cytoplasmic iASPP in regulating transcription.

Previous studies have shown that the C-termini of ASPP2 and iASPP have intrinsic nuclear localization properties (Slee et al., 2004). It has also been postulated in the past that ankyrin repeat domains (ARDs) may represent a unique type of nuclear localization signal similar as that shown for IκBα (Sachdev et al., 1998).

The present application is based, in part, on the discovery that phosphorylation of iASPP at one or more serine residues in the human iASPP amino acid sequence and/or intracellular localization of iASPP in a cancer cell correlates with, and is believed to have an effect on the metastatic potential of a cancer cell. Identifying that iASPP is regulated by serine phosphorylation and the associated downstream event is not only valuable for understanding iASPP regulated p53-dependent or -independent cellular signaling pathways but also is useful to select more effective treatment regimens and/or develop new strategies of cancer treatment as described herein.

I. Diagnostic Methods

In one aspect, described herein is a method of evaluating metastatic potential of a cancer comprising measuring phosphorylation state and/or intracellular localization of iASPP in a cancer cell from a mammalian subject and diagnosing metastatic potential of the cancer based on the phosphorylation state and/or intracellular localization of iASPP in the cancer cell measured according to the measuring step. Such classification of tumors is useful for treating human subjects in a clinical setting. Such classification also is useful for laboratory research involving experimental animals, e.g., genetically engineered mouse models of cancer. Such methods also could be described as methods of stratifying or grading tumors into, e.g., two, three, four, five or more categories based on this measurement.

The invention is contemplated to be useful with respect to any cancer type. Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In some embodiments, the cancer cell is from a cancer selected from the group consisting of melanoma, prostate cancer, head cancer and neck cancer. In some embodiments, the cancer cell is from a primary tumor from the subject.

In some embodiments, the method further comprises screening the cancer cell for at least one parameter selected from the group consisting of: a p53 mutation that reduces a tumor suppressive function of p53, an elevated measurement of mdm2 protein or mRNA, and a B-RafV600E mutation; and diagnosing metastatic potential of the cancer based on the phosphorylation state and/or intracellular localization of iASPP in the cancer cell and from the presence or absence of the at least one parameter. The at least one parameter optionally comprises the p53 mutation that reduces a tumor suppressive function of p53. More than 26,000 somatic mutation data of p53 has been collected and appear in the international agency for research on cancer (IARC) TP53 database version R14 (www-p53.iarc.fr/). The absence of such a p53 mutation can be characterized as the presence of a wild type functioning p53.

In some variations, to provide a basis for the identification of cancers at risk for metastasis, phosphorylated iASPP measurements (or intracellular localization measurements) from multiple human subjects are obtained, both in healthy tissues and cancer tissue, to establish a data set of phosphorylated iASPP expression. With an established data set, a variety of standard statistical analyses can be performed to identify when a measurement of phosphorylated iASPP is elevated, e.g., in a statistically significant manner relative to a healthy control. The data set can be used to stratify cancers into two, three, four, five or more categories. For example, in some embodiments, the determination that 0%-20% of the iASPP in the sample is phosphorylation is indicative that the cells in the sample are not cancerous. A determination that about 20% to about 50% of the iASPP in the sample is phosphorylated is indicative that the cells in the sample are from a primary tumor (i.e., a tumor that has not yet metastasized). A determination that about 50% to about 80% of the iASPP in the sample is phosphorylated is indicative that the cells in the sample are from a primary tumor in transition to metastasis. A determination that about 80% to about 100% of the iASPP in the sample is phosphorylated is indicative that the cells in the sample are from a metastasized tumor.

To assess the relative level of phosphorylated iASPP expression, the level of phosphorylated iASPP expression in a cancer tissue sample is subjected to one or more of various comparisons. In general, it can be compared to: (a) phosphorylated iASPP expression level(s) in normal tissue from the organ in which the cancer originated; (b) phosphorylated iASPP expression level(s) in a collection of comparable cancer tissue samples; (c) phosphorylated iASPP expression level(s) in a collection of normal tissue samples; or (d) phosphorylated iASPP expression level(s) in an arbitrary standard. In some embodiments, a phosphorylated iASPP measurement of at least 1.0, 1.5, 2.0, 2.5 or at least 3.0 standard deviation(s) greater than a median phosphorylated iASPP measurement in corresponding healthy tissue is scored as elevated phosphorylated iASPP expression. In other embodiments, a phosphorylated iASPP measurement that is statistically significantly greater than phosphorylated iASPP measurements in corresponding healthy tissue, with a p-value less than 0.1, or less than 0.05, or less than 0.01, or less than 0.005, or less than 0.001 is scored as elevated phosphorylated iASPP expression. As a data set enlarges, the comparison can be refined by stratifying the data for additional variables, such as the age, sex, ethnicity, body mass, smoking habits or other factors that differentiate subjects.

In some embodiments, the screening methods described herein comprise comparing a measurement of phosphorylated iASPP (or iASPP localization) in the cancer tissue sample with phosphorylated iASPP (ir iASPP localization) measurement in healthy tissue of the same type as the tumor or increased nuclear localization, wherein elevated phosphorylated iASPP expression in the tumor compared to the healthy tissue, identifies the cancer as being at greater risk for metastasis.

In some embodiments, the measuring comprises measuring the phosphorylation state and/or intracellular localization of iASPP in a plurality of cancer cells from the mammalian subject and diagnosing metastatic potential of the cancer based on an average measurement from the plurality of the cells, or from a percentage of the cells that exceed a cut-off or reference measurement.

The diagnosing, in some embodiments, is made from the percentage of total iASPP that is phosphorylated or the percentage of total iASPP that is localized in the nucleus of the cell.

The level of phosphorylated iASPP in a sample, in some embodiments, can be compared to a predetermined "cut-off" concentration of phosphorylated iASPP that has been determined from observations to represent an elevated measure of phosphorylated iASPP that (when equaled or exceeded) is predictive of metastatic potential of a cancer. Determination of a suitable cut-off is made using, e.g., statistical analysis of phosphorylated iASPP concentration data collected from multiple healthy and/or cancer patients. If a "cut-off" value is employed, the cut-off concentration preferably is statistically determined to have optimal discriminating value to identify those cancers with elevated metastatic potential It will be appreciated that statistical analysis of a dataset will permit clinicians to make informed decisions based on concentrations other than the optimal discriminating concentration (e.g., above or below the optimal discriminating concentration). For example, using receiver-operating-characteristic curves, or using other statistical summaries of phosphorylated iASPP concentration and observed metastases according to the invention, the practitioner is capable of selecting a cut-off phosphorylated iASPP concentration having a desired level of sensitivity or specificity for predicting metastatic potential of a cancer. Considerations regarding the probability of success of targeted therapy based on the phosphorylated iASPP concentration, versus the probability of success of alternative therapies based on any available clinical data, can guide the selection of an appropriate cut-off concentration of phosphorylated iASPP for making a treatment decision.

In some embodiments, the cut-off is determined by measuring total iASPP in the sample, and determining an amount of phosphorylated iASPP in the total iASPP, wherein the determination that at least about 50% (or at least about 60%, or at least about 70%, or at least about 80%, or at least about 90% or at least about 95%) or more of the total iASPP in the sample is phosphorylated at one or both of Ser84 and Ser113 indicates that the cancer has an increased risk for metastasis.

The cut-off could also be determined by identifying a ratio of phosphorylated iASPP to total iASPP within a cell, wherein an increased amount of phosphorylated iASPP compared to the amount of total iASPP in the cell indicates that the cancer has a increased risk for metastasis.

As described elsewhere herein, the screening methods described herein may optionally comprise the step of prescribing for or administering to the subject identified as having elevated phosphorylated iASPP expression in the biological sample a composition comprising a molecule that suppresses expression or activity of cdk1, a molecule that inhibits iASPP phosphorylation, an inhibitor of mdm2-induced degradation of p53 and/or an inhibitor of B-RafV600E. By "prescribing" is meant providing an order or authorization for the therapy, which may be dispensed to the subject for self-administration and/or administered by a medical professional that is different from the prescribing professional.

A. Methods of Measuring iASPP Phosphorylation in a Sample

The terms evaluation of measurement of "phosphorylation state of iASPP" and "iASPP phosphorylation" as used herein refer to iASPP phosphorylated at one or more serine residues at the amino terminus of the polypeptide. For example, in some embodiments, the iASPP polypeptide comprises a phosphorylated serine residue selected from the group consisting of Ser84 and Ser113 of human iASPP (SEQ ID NO: 2). In some embodiments, Ser84 of human iASPP is phosphorylated. In other embodiments, See 113 of human iASPP is phosphorylated. In still other embodiments, both Ser84 and S113 of human iASPP are phosphorylated. For the purposes of this aspect of the invention, phosphorylation of iASPP at other residues such as a tyrosine, and phosphorylation of residues outside of the amino-terminus, are not considered in the measurement or evaluation of the "phosphorylation state."

Some methods for measuring phosphorylated iASPP employ an agent that binds a phosphorylated form of iASPP with great specificity and binding affinity. Other methods employ an agent that selectively binds iASPP that is unphosphorylated at Ser84 and/or Ser113. Although exemplified with antibodies, other suitable binding partners exist and can be used to practice the invention.

In some embodiments, an antibody that binds iASPP and preferentially binds a phosphorylated form of iASPP is used to measure the amount of phosphorylated iASPP in a sample. To determine a measurement of phosphorylated iASPP, a biological sample from a mammalian subject is contacted with an iASPP antibody that preferentially binds phosphorylated iASPP under conditions and for a time sufficient to allow immunocomplexes to form. Immunocomplexes formed between the iASPP antibody and phosphorylated iASPP in the sample are then detected. The amount of phosphorylated iASPP in the biological sample is quantitated by measuring the amount of the immunocomplex formed between the antibody and the phosphorylated iASPP. For example, the capture antibody can be quantitatively measured if it has a detectable label, or a secondary antibody can be used to quantify the immunocomplex.

In some embodiments, the biological sample comprises cancerous tissue. Cancerous tissue from a solid tumor (e.g., a carcinoma, sarcoma, glioma or lymphoma) can be obtained by using conventional tumor biopsy instruments and procedures. Endoscopic biopsy, excisional biopsy, incisional biopsy, fine needle biopsy, punch biopsy, shave biopsy and skin biopsy are examples of recognized medical procedures that can be used by those of skill in the art to obtain tumor samples for use in practicing the methods described herein. Samples of cancerous lesions may be obtained by resection, bronchoscopy, fine needle aspiration, bronchial brushings, or from sputum, pleural fluid or blood. In some variations, a tumor or tumor biopsy is obtained from a subject and fluid from the tumor is removed, e.g., by centrifugation, and the tumor fluid is used as the sample for measuring phosphorylated iASPP.

In one aspect, measuring the phosphorylation state of iASPP in a cancer cell comprises an analytical technique selected from the group consisting of (a) an analytical technique that provides an absolute measure of phosphorylated iASPP, (b) an analytical technique that provides a relative measure of phosphorylated iASPP to total iASPP in the cell and (c) an analytical technique that provides a relative measure of phosphorylated iASPP to unphosphorylated iASPP in the cell.

An exemplary method for determining the absolute measure of phosphorylated iASPP in the cancer cell comprises contacting the cancer cell, or iASPP isolated from the cancer cell, with binding partner that specifically binds the phosphorylated iASPP, and measuring the amount of phosphorylated iASPP from the amount of complex formed between the iASPP and binding partner. Optionally, the second binding partner comprises a detectable label and measuring the amount of phosphorylated iASPP is achieved by measuring the amount of the binding partner-iASPP complex formed.

In some embodiments, the method comprises measuring total iASPP in the cell and measuring unphorylated iASPP in the cell, wherein a difference between total iASPP and unphosphorylated iASPP provides an indication of the amount of phosphorylated iASPP in the cell.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats can readily be adapted to employ the antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The tests of the present invention include cells, protein extracts of cells, or biological fluids such as, blood, serum, and plasma. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In addition, such assays may be useful in evaluating the efficacy of a particular therapeutic treatment regime in animal studies, in clinical trials, or in monitoring the treatment of an individual patient.

In some embodiments, the iASPP polypeptide or the binding partner is attached to a solid support, and binding is detected by detecting a complex between the polypeptide and the binding partner on the solid support. The binding partner optionally comprises a detectable label and binding is detected by detecting the label in the polypeptide-binding partner complex.

A relative measure of phosphorylated iASPP to total iASPP in the cancer cell can be determined by contacting the cancer cell, or iASPP isolated from the cancer cell, with a first binding partner and a second binding partner, wherein the first binding partner binds iASPP and the second binding partner specifically binds the phosphorylated iASPP. A relative measure of phosphorylation is obtained by comparing the amount of complex formed between iASPP and the first and second binding partners. Optionally, the first binding partner comprises a first detectable label and the second binding partner comprises a second detectable label, to facilitate measuring the phosphorylation state of iASPP by measuring the amount of the second binding partner-iASPP complex formed and measuring total iASPP by measuring the amount of first binding partner-iASPP complex formed. In some embodiments, the phosphorylated iASPP recognized by the second binding partner comprises one or more phosphorylated serine residues selected from the group consisting of Ser84 and Ser113.

The method comprises, in some embodiments, contacting the cancer cell, or protein isolated from the cancer cell, with a binding partner that preferentially binds iASPP in which one or more serine residues selected from serine 84 (Ser84, SEQ ID NO: 2) and serine 113 (Ser113, SEQ ID NO: 2) is not phosphorylated (to permit evaluation of the relative amount of total iASPP that is unphosphorylated, as an indirect measure of the amount that is phosphorylated).

The measuring steps described herein optionally comprise isolating iASPP from the cancer cell, and measuring one or more phosphorylated serine residues in the isolated iASPP. In some variations, the iASPP is cleaved, and phosphorylation is measured in one or more of the cleaved peptides. The cleaved peptides may be separated by electrophoresis based upon size (e.g., by SDS-PAGE or sizing gel). Other separation techniques may include aqueous two-phase partitioning and non-denaturing agarose gel electrophoresis separation. In other embodiments, separation employs denaturing system such as an isoelectric focusing (IEF) gel, capillary electrophoresis, or isotachyphoresis. Alternatively or additionally, two-dimensional electrophoretic analysis may be used (e.g., Wilkins et al., Proteome Research: New Frontiers in Functional Genomics, Springer-Verlag, Berlin, 1997). Proteins can be visualized on such gels using any of various stains known in the art (e.g., Trypan Blue or Sypro-Ruby dye). In some embodiments, the method comprises measuring an absolute or relative amount of each iASPP band as a measure of iASPP phosphorylation state. Mass spectrometry technique can be used to quantify phosphorylated and unphosphorylated peptides to provide a measure of iASPP phosphorylation.

A relative measure of phosphorylated iASPP to unphosphorylated iASPP in the cancer cell can be determined by, for example, separating phosphorylated and unphosphorylated iASPP in the cancer cell, and measuring the amounts of separated phosphorylated and unphosphorylated iASPP relative to each other. For example, in some embodiments, the separating step comprises contacting the cancer cell, or iASPP isolated from the cancer cell, with a binding partner that binds unphosphorylated iASPP and the second binding partner specifically binds the phosphorylated iASPP, and isolating formed phosphorylated iASPP-binding partner complex.

The separation step can be accomplished in a variety of ways. For example, at least one of the components can be immobilized on a solid substrate, from which the unbound components may be easily separated. The solid substrate can be made of a wide variety of materials and in a wide variety of shapes, such as a microtiter plate, a microbead, a dipstick, or a resin particle. Ideally, the substrate provides maximum signal to noise ratios, to minimize background binding.

In one example, separation is achieved by removing a bead or dipstick from a reservoir, emptying or diluting a reservoir such as a microtiter plate well, rinsing a bead, particle, chromatographic column or filter with a wash solution or solvent. The separation step can include multiple rinses or washes. For example, when the solid substrate is a microtiter plate, the wells can be washed several times with a washing solution, which typically includes those components of the incubation mixture that do not participate in specific bindings such as salts, buffer, detergent, non-specific protein. Where the solid substrate is a magnetic bead, the beads can be washed one or more times with a washing solution and isolated using a magnet.

Detection of the presence or absence of a polypeptide comprising an iASPP-binding partner complex can be achieved using any method known in the art. For example, the transcript resulting from a reporter gene transcription assay of an iASPP polypeptide interacting with a target molecule (e.g., binding partner) typically encodes a directly or indirectly detectable product (such as β-galactosidase activity, luciferase activity, and the like). For cell free binding assays, one of the components usually includes, or is coupled to, a detectable label. A wide variety of labels can be used, such as those that provide direct detection (such as radioactivity, luminescence, optical or electron density) or indirect detection (such as epitope tag such as the FLAG epitope, enzyme tag such as horseradish peroxidase). The label can be bound to an iASPP binding partner, or incorporated into the structure of the binding partner.

A variety of methods can be used to detect the label, depending on the nature of the label and other assay components. For example, the label can be detected while bound to the solid substrate or subsequent to separation from the solid substrate. Labels can be directly detected through optical or electron density, radioactive emissions, nonradiative energy transfers or indirectly detected with antibody conjugates, or strepavidin-biotin conjugates. Methods for detecting the labels are well known in the art.

As described herein, the phosphorylation state of iASPP in the cancer cell is useful to diagnose metastatic potential of a cancer. In some embodiments, the diagnosing comprises comparing the amount of phosphorylated iASPP in the cancer cell with a measurement of phosphorylated iASPP from healthy cells of the same type as the cancer cell, wherein increased iASPP phosphorylation in the cancer cell relative to the healthy cell indicates that the cancer is at increased risk for metastases. In other embodiments, the diagnosing comprises comparing the percentage of iASPP that is phosphorylated in the cancer cell with a calculation of the percentage of iASPP that is phosphorylated in a healthy cell of the same type as the cancer cell, wherein increased percentage of phosphorylated iASPP in the cancer cell indicates that the cancer is at increased risk for metastases.

In any of the methods described herein, the binding partner preferentially binds iASPP in which one or more serine residues selected from serine 84 (Ser84 of SEQ ID NO: 2) and serine 113 (Ser113 of SEQ ID NO: 2) is phosphorylated, and measuring the phosphorylation state by measuring the amount of protein-binding partner complex formed to provide a measure of iASPP that is phosphorylated at one or more of the serine residues.

In some variations, the complete iASPP polypeptide is employed in the assay. However, evidence, including that described below, indicates that cyclinB1/cdk1 phosphorylates serine at an amino-terminal portion of iASPP, and that it is unnecessary to use the complete iASPP for assays to measure phosphorylation. The term "iASPP amino-terminal domain" ("N-iASPP") refers to a portion of iASPP that is sufficient to exhibit the activity (e.g., interaction with the kinase to receive phosphorylation of a serine). It is possible to determine a minimum effective iASPP amino-terminal domain by screening deletion fragments of iASPP according to kinase assay procedures described herein. The iASPP amino-terminal domain can be fused to other sequences to make fusion proteins, and/or contain additional moieties such as labels and tags. Similarly, it is possible to use an iASPP substrate to screen for fragments of the kinase that is effective to phosphorylate iASPP for practicing methods of the invention.

The phosphorylation state of iASPP can be determined in a full length iASPP amino acid sequence or in fragments of the iASPP amino acid sequence that include Ser84 and/or SER113. In one aspect, the iASPP polypeptide comprises an amino-terminal domain fragment of SEQ ID NO: 2, wherein the amino-terminal amino acid of the fragment is selected from the group consisting of residues 1-83 of SEQ ID NO: 2, and wherein the carboxy terminal amino acid of the fragment is selected from the group consisting of residues 113-500 of SEQ ID NO: 2. In some embodiments, the iASPP polypeptide comprises amino acids 1-240 of SEQ ID NO: 2 or amino acids 1-828 of SEQ ID NO: 2. In other aspects, the polypeptide comprising an iASPP amino-terminal domain comprises amino acids 81-130 of SEQ ID NO: 2. In another aspect, the polypeptide comprising an iASPP amino-terminal domain comprises amino acids 1-478 of SEQ ID NO: 2.

In various embodiments, the iASPP amino terminal domain optionally includes at least one phosphorylated serine between residues 84 and 113 (inclusive) of SEQ ID NO: 2. For example, in some embodiments, the iASPP amino terminal domain comprises amino acids 81-130 of SEQ ID NO: 2, wherein the serines at positions 84 and 113 of SEQ ID NO: 2 are phosphorylated. In other embodiments, the iASPP amino terminal domain comprises amino acids 81-130 of SEQ ID NO: 2, wherein the serine at position 84 of SEQ ID NO: 2 is phosphorylated. In still other embodiments, the iASPP amino terminal domain comprises amino acids 81-130 of SEQ ID NO: 2, wherein the serine at position 113 of SEQ ID NO: 2 is phosphorylated.

Phosphorylated serine levels can be measured in situ or in cells isolated from biological samples by standard in vitro techniques well known in the art, such as enzyme-linked immunosorbant assay (ELISA), radio immunoassay (RIA), Western blot, or immunofluorescence-based assays. iASPP activity can also be measured in biological samples using fluorescent microscopy with fluorescently labeled anti-iASPP and anti-phosphoserine antibodies. The detection is correlated, for example, by a brighter staining signal in a fluorescent microscopy assay, the presence of more staining in a fluorescent microscopy assay, or by decreased fluid levels of phosphorylated iASPP as detected by Western blot, ELISA, RIA or other immunofluorescence-based assays, such as fluorescence resonance electron transfer (FRET). As described herein, it is possible to measure phosphorylated iASPP using antibodies that specifically recognize iASPP and differentiate between a phosphorylated versus unphosphorylated form. Alternatively, it may be possible to measure phosphorylation of iASPP by isolating/measuring total iASPP (e.g., with an antibody that recognizes an epitope unaffected by phosphorylation and using a phosphoserine antibody or other tool that permits quantification of phosphorylation.

High-content screens (HCS) provide for analysis of multiple parameters in a single screening assay. For example, phosphorylation of a polypeptide comprising an iASPP amino-terminal domain may be measured using phosphoserine-specific antibodies fluorescing in a particular excitation channel (e.g., Alexa Fluor 488 excites at 488 nm).

An anti-phosphoserine antibody or anti-phosphorylated iASPP antibody suitable for use in the method of the invention may comprise a label, such as a radioisotope, a fluorophore, a fluorescing protein (e.g., natural or synthetic green fluorescent proteins), a dye, an enzyme, a substrate, or the like. The label is a compound or moiety known in the art to be useful as a label, including biotin molecules, alkaline phosphatase, fluorophores (e.g., fluoroisothiocyanate, phycoerythrin, Texas red, Alexa Fluor stains, and other fluorescent dyes well known in the art), radioisotopes (e.g., 3H, Europium3+, 32P), genetically engineered peptide tags such as a histidine (His6) tag linked to the aggregating polypeptide, a myc-tag, a Hemagluttinin tag, and the like. Biotin, fluorophores, and other contemplated small molecules comprising a label can be linked to the polypeptide of the invention by means well-known in the art such as a commercially produced Biotinylation kit (Sigma Chem. Co., St. Louis, Mo.), or alternative methods commonly used in organic chemistry to attach a small molecule to a peptide or protein (see e.g., Current Protocols in Protein Chemistry, John Wiley & Sons, 2001). Genetically engineered tags, e.g., His6 and myc-tags, are operably linked to the polypeptide of the invention using standard recombinant DNA methods well known in the art (see e.g., Current Protocols in Molecular Biology, supra), or using conventional peptide synthesis techniques. Such labels facilitate quantitative detection with standard laboratory machinery and techniques.

B. Intracellular localization of iASPP

As described herein, intracellular localization of iASPP in a cancer cell is indicative of whether the cancer cell is at an increased risk for metastasis. The term "intracellular localization" as used herein refers to the location of iASPP within the cell. In some cells, iASPP is located within the cytoplasm of the cell. In other cells, the iASPP is located within the nucleus of the cell or is divided between the cytoplasm and nucleus. As shown herein, increased nuclear localization of iASPP is associated with increased risk of metastasis. Without intended to be limited to any particular theory, the nuclear iASPP is believed to inhibit tumor suppressive activity of p53. Intracellular localization can be measured by methods known in the art, such as immunohistochemical analysis.

In some embodiments, the amount of iASPP within the cytoplasm is measured. In some embodiments, the amount of iASPP within the nucleus is measured.

In some embodiments, intracellular localization is measured by an analytical technique selected from the group consisting of an analytical technique that provides an absolute measure of iASPP in the nucleus of the cancer cell, analytical technique that provides a relative measure of iASPP in the nucleus to total iASPP in the cell, and an analytical technique that provides a relative measure of iASPP in the nucleus to iASPP in the cytoplasm in the cell. In some embodiments, the measuring comprises immunohistochemical staining of the cancer cell with an antibody that specifically binds iASPP.

Intracellular localization is measured, in some embodiments, by comparing the measure of iASPP in the nucleus of the cancer cell with a measure of iASPP in a healthy cell of the same type as the cancer cell, wherein increased iASPP in the nucleus of the cancer cell compared to the healthy cell indicates an increased metastatic potential for the cancer.

Methods of measuring intracellular localization as described herein optionally comprise contacting the cancer cell with a nuclear-specific marker. Nuclear-specific markers are known in the art and include, but are not limited to, Hoechst 33258, Hoechst 33342, 4',6-Diamidino-2-phenylindole (DAPI); 4',6-diacarboxyamide-2-phenylindole (DCI); 7-Aminoactinomycin D (7-AAD); Ethidium bromide; Ethidium homodimer; Propidium iodide (PI); Antraquinone dye (DRAQ5); TO-PRO-1; TO-PRO-3; TOTO-1; TOTO-3; YO-PRO-1; YOYO-1; SYTOX Green; Acridine orange (AO) and Pyronin Y. See, for example, Haughland, R. (1998) Handbook of fluorescent probes and research chemicals, 6 Ed., Molecular Probes, Inc., the disclosure of which is incorporated by reference in its entirety.

In some embodiments, intracellular localization of iASPP is measured in a section of a tumor tissue sample using procedures described in, for example, Van Impe et al., (2008). A new role for nuclear transport factor 2 and Ran: nuclear import of CapG. Traffic (Copenhagen, Denmark) 9, 695-707, the disclosure of which is incorporated herein by reference in its entirety. For example, in some embodiments, the method comprises contacting a tissue sample with an antibody that binds iASPP and labeled with a nuclear specific marker and counting the number of cells in which co-localization of the iASPP antibody with the nuclear specific marker is detected. In another embodiment, the method comprises containing a tissue sample with an antibody that specifically binds iASPP, wherein the antibody comprises a detectable marker, and contacting the tissue sample with a nuclear specific marker, identifying iASPP within the nucleus of cells in the tissue sample by detecting the presence of an iASPP-antibody complex within the nucleus of the cells and counting the number of cells in which the iASPP-antibody complex is identified in the nucleus of the cells.

The methods described herein optionally comprise measuring the mitotic index of the cancer using methods known in the art, such as those described in Example 3.

II. Binding Partners

Binding partners (e.g., antibodies) that bind to phosphorylated forms of iASPP are also contemplated. In one aspect, described herein is an iASPP binding partner selected from the group consisting of (a) an antibody that specifically binds iASPP polypeptide and preferentially binds to iASPP having a phosphorylated serine compared to binding to iASPP without the phosphorylated serine, wherein said serine residue corresponds to a serine selected from the group consisting of Ser84 and Ser113 of the human iASPP amino acid sequence of SEQ ID NO: 2; (b) a fragment of (a) that specifically binds iASPP polypeptide and preferentially binds to iASPP having the phosphorylated serine; and (c) a polypeptide that comprises (b) and that specifically binds iASPP polypeptide and preferentially binds to iASPP having the phosphorylated serine.

In some embodiments, the antibody binds to an epitope of the phosphorylated peptide comprising a portion of the amino acid sequence SRGpSPRKAATDGADTPFGRDE-SAPTLHPYSPLpSPKGRPSSPRTPLYLQPD (amino acids 81-130 of SEQ ID NO: 2), where pS is a phosphorylated serine. In some embodiments, the antibody binds to an epitope of the phosphorylated peptide that comprises at least 4 (or at least 5, at least 6, at least 7, at least 8, at least 9, at least 10, at least 11, at least 12, at least 13, at least 14, at least 15, at least 16, at least 17, at least 18, at least 19, at least 20, at least 25, at least 30 or more) of amino acids 81-130 of SEQ ID NO: 2. For example, in some variations, the antibody binds to an epitope of the phosphorylated iASPP peptide that comprises amino acids 81-86 of SEQ ID NO: 2, or amino acids 81-90 of SEQ ID NO: 2, or amino acids 81-95 of SEQ ID NO: 2, or amino acids 81-100 of SEQ ID NO: 2, or amino acids 83-89 of SEQ ID NO: 2, or amino acids 83-94 of SEQ ID NO: 2, or amino acids 83-100 of SEQ ID NO: 2, or amino acids or amino acids 110-115 of SEQ ID NO: 2, or all or some of amino acids 107-118 of SEQ ID NO: 2, or amino acids 110-120 of SEQ ID NO: 2, or amino acids 110-125 of SEQ ID NO: 2 or amino acids 111-122 of SEQ ID NO: 2. In one variation, the antibody binds to a phosphorylated iASPP peptide that comprises a conformational epitope. In such variations, for example, the antibody binds to multiple epitopes within amino acids 81-130 of SEQ ID NO: 2.

In another aspect, described herein is an iASPP binding partner selected from the group consisting of (a) an antibody that specifically binds iASPP polypeptide and preferentially binds iASPP in which one or more serine residues selected from serine 84 (Ser84, SEQ ID NO: 2) and serine 113 (Ser113, SEQ ID NO: 2) is not phosphorylated. compared to binding to iASPP having the phosphorylated serine, (b) a fragment of (a) that specifically binds iASPP polypeptide and preferentially binds to iASPP having the phosphorylated serine; and (c) a polypeptide that comprises (b) and that specifically binds iASPP polypeptide and preferentially binds to iASPP without the phosphorylated serine. In some embodiments, the antibody is LX128.5 (i.e., an antibody that binds to an epitope comprising all or some of amino acids 111-122 of SEQ ID NO: 2, including serine 113).

In some embodiments, the antibody is selected from the group of antibodies consisting of LX49.3, LX128.1, LX128.2, LX128.3, LX128.4, LX128.5, LX128.6, LX128.7, LX128.9 and LC128.10. In one embodiments, the antibody is LX128.5.

An antibody or antibody fragment that specifically binds to a phosphorylated form of iASPP can be identified, for example, by immunoassays, BIAcore, or other techniques known to those of skill in the art. An antibody or antibody fragment binds specifically to phosphorylated iASPP when it binds to the phosphorylated iASPP with higher affinity than to any cross-reactive protein (especially unphosphorylated iASPP) as determined using experimental techniques, such as RIAs and ELISAs. Typically, a specific or selective reaction will be at least twice the background signal or noise and more typically more than 10 times background. In one embodiment, the antibody specifically binds to an epitope that includes one or more phosphorylated serine residues (Ser84 or Ser113) of iASPP. In another certain embodiment, the antibody specifically binds to an epitope that includes only one phosphorylated serine residue of iASPP.

Antibodies useful for detecting peptides comprising phosphorylated serine residues are generated using techniques well known in the art. In some variations, phosphorylated iASPP or phosphorylated iASPP fragments are used as an antigen to immunize an animal, or to select antibodies from a library. The antibodies so selected are then screened against unphosphorylated iASPP, to identify antibodies that selectively bind the phosphorylated, but not the unphosphorylated, form. An analogous process, starting with unphosphorylated iASPP, is used to select antibodies specific for the unphosphorylated form.

The invention contemplates use of antibodies (e.g., monoclonal and polyclonal antibodies, single chain antibodies, chimeric antibodies, bifunctional/bispecific antibodies, humanized antibodies, human antibodies, and complementarity determining region (CDR)-grafted antibodies, including compounds that include CDR sequences specifically recognizing a polypeptide of the invention and specific for polypeptides of interest to the invention, especially phosphorylated serine on the iASPP polypeptide). Antibodies can be human antibodies which are produced and identified according to methods described in WO 93/11236, which is incorporated herein by reference in its entirety. Antibody fragments, including Fab, Fab', F(ab')$_2$, and Fv, and single-chain antibodies are also provided by the invention. The term "specific for," when used to describe antibodies of the invention, indicates that the variable regions of the antibodies of the invention recognize and bind the polypeptide of interest with a detectable preference (i.e., able to distinguish the polypeptide of interest from other known polypeptides of the same family, by virtue of measurable differences in binding affinity, despite the possible existence of localized sequence identity, homology, or similarity between family members). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies of the invention can be produced using any method well known in the art.

Various procedures known in the art may be used for the production of polyclonal antibodies to peptides comprising phosphorylated serine. For the production of antibodies, various host animals (including but not limited to rabbits, mice, rats, hamsters, and the like) are immunized by injection with a phosphorylated iASPP protein or peptide. Various adjuvants may be used to increase the immunological response, depending on the host species, including but not limited to Freund's (complete and incomplete) adjuvant, mineral gels such as aluminium hydroxide, surface active substances such as lysolecithin, pluronic polyols, polyanions, oil emulsions, keyhole limpet hemocyanins, dinitrophenol, and potentially useful human adjuvants such as BCG (*Bacillus* Calmette-Guerin) and *Corynebacterium parvum*.

A monoclonal antibody to a phosphorylated epitope of iASPP may be prepared by using any technique which provides for the production of antibody molecules by continuous cell lines in culture. These include but are not limited to the hybridoma technique originally described by Köhler et al., Nature, 256: 495-497 (1975), and the more recent human B-cell hybridoma technique [Kosbor et al., Immunology Today, 4: 72 (1983)] and the EBV-hybridoma technique [Cole et al., Monoclonal Antibodies and Cancer Therapy, Alan R Liss, Inc., pp. 77-96 (1985), all specifically incorporated herein by reference]. Antibodies against phosphorylated iASPP also may be produced in bacteria from cloned immunoglobulin cDNAs. With the use of the recombinant phage antibody system it may be possible to quickly produce and select antibodies in bacterial cultures and to genetically manipulate their structure.

When the hybridoma technique is employed, myeloma cell lines may be used. Such cell lines suited for use in hybridoma-producing fusion procedures preferably are non-antibody-producing, have high fusion efficiency, and exhibit enzyme deficiencies that render them incapable of growing in certain selective media which support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions. It should be noted that the hybridomas and cell lines produced by such techniques for producing the monoclonal antibodies are contemplated compositions of the present invention.

In addition to the production of monoclonal antibodies, techniques developed for the production of "chimeric antibodies," the splicing of mouse antibody genes to human antibody genes to obtain a molecule with appropriate antigen specificity and biological activity can be used [Morrison et al., Proc. Natl. Acad. Sci. 81:6851-6855 (1984); Neuberger et al., Nature 312:604-608 (1984); Takeda et al., Nature 314:452-454 (1985)]. Alternatively, techniques described for the production of single-chain antibodies (U.S. Pat. No. 4,946,778) can be adapted to produce phosphorylated-iASPP peptide-specific single chain antibodies.

Antibody fragments which contain the idiotype of the molecule may be generated by known techniques. For example, such fragments include, but are not limited to, the F(ab')$_2$ fragment which may be produced by pepsin digestion of the antibody molecule; the Fab' fragments which may be generated by reducing the disulfide bridges of the F(ab')$_2$ fragment, and the two Fab fragments which may be generated by treating the antibody molecule with papain and a reducing agent.

Rapid, large scale recombinant methods for generating antibodies may be employed, such as phage display [Hoogenboom et al., J. Mol. Biol. 227: 381, (1991); Marks et al., J. Mol. Biol. 222: 581, (1991)] or ribosome display methods, optionally followed by affinity maturation [see, e.g., Ouwehand et al., Vox Sang 74(Suppl 2):223 232 (1998); Rader et al., Proc. Natl. Acad. Sci. USA 95:8910 8915 (1998); Dall'Acqua et al., Curr. Opin. Struct. Biol. 8:443 450, (1998)]. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach.

"Antibody fragments" comprise a portion of an intact immunoglobulin, e.g., an antigen binding or variable region of the intact antibody, and include multispecific (bispecific, trispecific, etc.) antibodies formed from antibody fragments. Fragments of immunoglobulins may be produced by recombinant DNA techniques or by enzymatic or chemical cleavage of intact antibodies.

Nonlimiting examples of antibody fragments include Fab, Fab', F(ab')$_2$, Fv (variable region), domain antibodies (dAb, containing a $V_H$ domain) (Ward et al., Nature 341:544-546, 1989), complementarity determining region (CDR) fragments, single-chain antibodies (scFv, containing $V_H$ and $V_L$ domains on a single polypeptide chain) (Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)), single chain antibody fragments, diabodies ($V_H$ and $V_L$ domains on a single polypeptide chain that pair with complementary $V_L$ and $V_H$ domains of another chain) (EP 404,097; WO 93/11161; and Hollinger et al., Proc. Natl. Acad. Sci. USA, 90:6444-6448 (1993)), triabodies, tetrabodies, minibodies (scFv fused to CH3 via a peptide linker (hingeless) or via an IgG hinge) (Olafsen, et al., Protein Eng Des Sel. 2004 April; 17(4):315-23), maxibodies (bivalent scFvs covalently attached to the Fc region of an immunoglobulin; Fredericks et al, Protein Engineering, Design & Selection, 17:95-106 (2004) and Powers et al., Journal of Immunological Methods, 251:123-135 (2001)); linear antibodies (tandem Fd segments ($V_H$-$C_{H1}$-$V_H$-$C_{H1}$) (Zapata et al., Protein Eng., 8(10):1057-1062 (1995)); chelating recombinant antibodies (crAb, which can bind to two adjacent epitopes on the sane antigen) (Neri et al., J Mol Biol. 246:367-73, 1995), bibodies (bispecific Fab-scFv) or tribodies (trispecific Fab-(scFv)(2)) (Schoonjans et al., J Immunol. 165:7050-57, 2000; Willems et al., J Chromatogr B Analyt Technol Biomed Life Sci. 786:161-76, 2003), intrabodies (Biocca, et al., EMBO J. 9:101-108, 1990; Colby et al., Proc Natl Acad Sci USA. 101:17616-21, 2004) which may also comprise cell signal sequences which retain or direct the antibody intracellularly (Mhashilkar et al, EMBO J 14:1542-51, 1995; Wheeler et al., FASEB J. 17:1733-5, 2003), transbodies (cell-permeable antibodies containing a protein transduction domain (PTD) fused to scFv (Heng et al., Med Hypotheses. 64:1105-8, 2005), nanobodies (approximately 15 kDa variable domain of the heavy chain) (Cortez-Retamozo et al., Cancer Research 64:2853-57, 2004), small modular immunopharmaceuticals (SMIPs) (WO03/041600, U.S. Patent publication 20030133939 and US Patent Publication 20030118592), an antigen-binding-domain immunoglobulin fusion protein, a camelized antibody (in which VH recombines with a constant region that contains hinge, $C_{H1}$, $C_{H2}$ and $C_{H3}$ domains) (Desmyter et al., J. Biol. Chem. 276: 26285-90, 2001; Ewert et al., Biochemistry 41:3628-36, 2002; U.S. Patent Publication Nos. 20050136049 and 20050037421), a $V_{HH}$ containing antibody, heavy chain antibodies (HCAbs, homodimers of two heavy chains having the structure $H_2L_2$), or variants or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

III. Inhibitor Peptides

Another aspect of the invention includes peptides that inhibit iASPP phosphorylation. When such a peptide is introduced into a system that contains iASPP and a kinase capable of phosphorylating iASPP, the peptide inhibits the kinase from phosphorylating iASPP. Such inhibition can be measured by, e.g., a slowing of the rate at which the iASPP is phosphorylated; or by a reduced amount of phosphorylated iASPP in an equilibrium state. In some embodiments, the kinase is a serine kinase such as cyclinB1/cdk1.

In some variations, the peptide has a structure that mimics that portion of iASPP that is a kinase substrate, but does not function in downstream signaling pathways of phosphorylated iASPP. For example, the peptide may have a structure that binds cyclinB1/cdk1 and is itself phosphorylated, but lacks structure such as the C-terminal iASPP domain involved in downstream signaling. In some variations, the peptide irreversibly or reversibly binds the kinase to prevent the kinase from binding and phosphorylating endogenous iASPP. In some embodiments, the peptide has a structure that permits kinase binding, but lacks a structure to receive phosphorylation, e.g., serine deletion variants of iASPP/iASPP fragments. It will be appreciated that these variations are not mutually exclusive from each other.

In one aspect, described herein is an isolated peptide comprising an amino acid sequence selected from the group consisting of (a) a fragment of the iASPP amino acid sequence set forth in SEQ ID NO: 2, wherein the fragment binds to a kinase that phosphorylates iASPP at a serine residue selected from the group consisting of Ser84 and Ser113 of SEQ ID NO: 2; (b) an analog of (a) wherein from 1-10 amino acids have been deleted, inserted, or replaced with different amino acids, wherein said analog binds to the kinase that phosphorylates iASPP at a serine residue selected from the group consisting of Ser84 and Ser113 of SEQ ID NO: 2; (c) a cyclized version of (a) or (b) that binds to the kinase that phosphorylates iASPP at a serine residue selected from the group consisting of Ser84 and Ser113 of SEQ ID NO: 2; wherein the peptide binds to a kinase that phosphorylates iASPP at a serine residue selected from the group consisting of Ser84 and Ser113 of SEQ ID NO: 2, and wherein the peptide inhibits the kinase from phosphorylating iASPP.

In one variation, the peptide comprises an amino acid sequence at least 85% (or at least 90%, at least 91%, at least 92%, at least 93%, at least 94%, at least 95%, at least 96%, at least 97%, at least 99%) or more identical to a fragment of SEQ ID NO: 2, wherein the amino-terminal amino acid of the fragment is selected from the group consisting of residues 1-83 of SEQ ID NO: 2, and wherein the carboxy terminal amino acid of the fragment is selected from the group consisting of residues 113-500 of SEQ ID NO: 2. In other embodiments, the peptide comprises an amino acid sequence at least 85% (or at least 90%, at least 91%, at least 92%, at least 93%, at least 94%, at least 95%, at least 96%, at least 97%, at least 99%) or more identical to amino acids 1-240 of SEQ ID NO: 2 or amino acids 81-130 of SEQ ID NO: 2 or amino acids 107-118 of SEQ ID NO: 2.

In another variation, the iASPP inhibitor peptides described herein comprises a fragment of SEQ ID NO: 2 comprising at least 10, at least 15, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100 or more amino acids of SEQ ID NO: 2, wherein said fragment binds to a kinase that phosphorylates wild type iASPP at a serine residue selected from the group consisting of Ser84 and Ser113 of SEQ ID NO: 2.

Another aspect of the invention includes peptides that inhibit translocation of iASPP into the nucleus of a cancer cell, or a cancer cell line in which iASPP has been shown to localize to the nucleus. Without intending to be limited to any particular theory, the peptide is believed to operate in this manner by mimicking the self-interaction of an amino terminal region of iASPP with a carboxy terminal region of iASPP. In one variation, the peptide comprises an amino acid sequence at least 85% (or at least 90%, at least 91%, at least 92%, at least 93%, at least 94%, at least 95%, at least 96%, at least 97%, at least 99%) or more identical to amino acids 1-240 of SEQ ID NO: 2 with the proviso that the serine at residues 84 and 113 of SEQ ID NO: 2 are not phosphorylated, or a fragment thereof that mimics the self-interaction of an amino terminal fragment of iASPP with a carboxy terminal fragment of iASPP. In some embodiments, the peptide does not include S84D or S113D mutations. Data presented herein shows that iASPP with these mutations mimics phosphorylated wildtype iASPP.

Variant iASPP inhibitor peptides are also contemplated. Variant peptides may differ in amino acid sequence by one or more substitutions, additions, deletions, truncations which may be present in any combination. In one aspect, the modification is a conservative substitution. Such substitutions are those that substitute a given amino acid by another amino acid of like side chain characteristics, such as being acidic, basic, polar, nonpolar, aliphatic, aromatic, etc. The following non-limiting list of amino acids are considered conservative replacements (similar): a) alanine, serine, and threonine; b) glutamic acid and asparatic acid; c) asparagine and glutamine d) arginine and lysine; e) isoleucine, leucine, methionine and valine and f) phenylalanine, tyrosine and tryptophan.

The present disclosure includes iASPP inhibitor peptides, as well as synthetic examples of the proteins described herein. In addition, analogs (non-peptide organic molecules), derivatives (chemically functionalized peptide molecules obtained starting with the disclosed peptide sequences) and variants (homologs) of these proteins can be utilized in the methods described herein. For example, iASPP inhibitor peptides that include modifications, but retain the ability to interfere with the binding of wild type iASPP to an iASPP binding partner or the phosphorylation of iASPP are also contemplated. The peptides disclosed herein include a sequence of amino acids, which can be either L- or D-amino acids, naturally-occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula NR1R2 wherein R1 and R2 are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability. For example, a carboxyl-terminal or amino-terminal cysteine residue can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this disclosure having measurable or enhanced ability to bind an antibody. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165 174 and Principles of Pharmacology Munson (ed.) 1995, Ch. 102, for descriptions of techniques used in CADD. Also included within the scope of the disclosure are mimetics prepared using such techniques.

Nucleic acids encoding the inhibitor peptides are another aspect of the invention.

Vectors also are useful for "gene therapy" treatment regimens, wherein a polynucleotide that encodes a polypeptide of the invention is introduced into a subject in need of treatment involving the modulation (decreased level or inhibition) of iASPP phosphorylation, in a form that causes cells in the subject to express the polypeptide of the invention in vivo. Gene therapy aspects that are described in WO 2007/006573, the disclosure of which is incorporated herein by reference, is also applicable herein.

IV. Therapeutic Methods

Also described herein are methods of treatment comprising obtaining a tumor or tumor biopsy from a mammalian subject, measuring the phosphorylation state of iASPP in the tumor sample and prescribing for or administering to the subject with elevated iASPP phosphorylation a composition comprising a molecule that suppresses expression or signaling activity of cdk1, a molecule that inhibits phosphorylation of iASPP, an inhibitor of B-RafV600E, and/or an inhibitor of mdm2-induced degradation of p53. In some variations, the invention is simply the treatment steps without first determining the phosphorylation state of iASPP in a cancer cell of a mammalian subject.

In some embodiments, described herein are methods of treating a subject identified as having elevated iASPP phosphorylation comprising administering to the subject at least one therapeutic selected from the group consisting of a molecule that suppresses expression or signaling activity of cdk1, a molecule that inhibits phosphorylation of iASPP, an inhibitor of B-RafV600E, and an inhibitor of mdm2-induced degradation of p53. In some embodiments, the method comprises administering at least two therapeutics selected from the group consisting of a molecule that suppresses expression or signaling activity of cdk1, a molecule that inhibits phosphorylation of iASPP, an inhibitor of B-RafV600E, and an inhibitor of mdm2-induced degradation of p53.

In one aspect, a method of treating a mammalian subject with cancer is provided, wherein the method comprises administering to the subject an inhibitor of cyclinB1/cdk1-induced phosphorylation of iASPP; an inhibitor of mdm2-induced degradation of p53; and an inhibitor of B-RafV600E. In some variations, the compounds are in admixture and administered together. In some variations, the inhibitors are packaged together, and at least two of the inhibitors are not in admixture. The inhibitors are preferably administered in amounts effective to induce death of cancer cells in the mammalian subject.

Another aspect is a therapeutic regimen for treating cancer in a mammalian subject. For example, in some embodiments, the therapeutic regimen comprises measuring phosphorylation state and/or intracellular localization of iASPP in a cancer cell from a mammalian subject, screening the cancer cell for at least one parameter selected from the group consisting of a p53 mutation that reduces a tumor suppressive function of p53, an elevated measurement of mdm2 protein or mRNA, and a B-RafV600E mutation, and prescribing and/or administering a therapeutic regimen that includes an inhibitor of iASPP phosphorylation for a subject with a cancer characterized by elevated iASPP phosphorylation and/or iASPP nuclear localization.

The prescribing and/or administering optionally comprises a therapeutic regiment that includes an inhibitor of iASPP phosphorylation and a molecule that suppresses expression or signaling activity of cdk1.

The prescribing and/or administering optionally comprises a therapeutic regiment that includes an inhibitor of iASPP phosphorylation and an inhibitor of mdm2-induced degradation of p53, for a subject with a cancer characterized by elevated iASPP phosphorylation and/or iASPP nuclear localization and the absence of a p53 mutation that reduces the tumor suppressive function of p53.

In some embodiments, the prescribing and/or administering comprises a therapeutic regimen that includes an inhibitor of iASPP phosphorylation and an inhibitor of B-RafV600E, for a subject with a cancer characterized by elevated iASPP phosphorylation and/or iASPP nuclear localization and the presence of the B-Raf-V600E mutation.

P53 mutations that reduce tumor suppressive function of p53 in a plurality of cancer are well known in the art. For review, see Suzuki et al., J. Biomed. Biotechnol., 2011: 978312, 2001, the disclosure of which is incorporated here by reference in its entirety. More than 26,000 somatic mutation data of p53 appear in the international agency for research on cancer (IARC) TP53 database version R14 (www-p53.iarc.fr/).

In some embodiments, molecules that inhibit iASPP phosphorylation include molecules that suppress expression or signaling activity of cdk1 (i.e., a cdk1 inhibitor). Exemplary cdk1 inhibitors include, but are not limited to an antibody that binds cdk1 and inhibits ligand-mediated stimulation of cdk1; an antisense or interfering nucleic acid (e.g., antisense oligonucleotide; micro-RNA, short interfering RNA) that inhibits cdk1 expression; an antibody that binds cdk1; an antisense or interfering nucleic acid (e.g., antisense oligonucleotide; micro-RNA, short interfering RNA) that inhibits expression of cdk1, a small molecule that inhibits cdk1 expression or signaling; a small molecule that inhibits cdk1 expression or signaling; and a molecule that inhibits cyclinB1 from binding to cdk1.

In some embodiments, the cdk1 inhibitor is an antibody (e.g., an antibody that binds to cdk1 and inhibits formation of the cyclinB1/cdk1 complex). Such antibodies include, but are not limited to, polyclonal, monoclonal, chimeric, single chain, Fab fragments and fragments produced by a Fab expression library, bifunctional/bispecific antibodies, humanized antibodies, CDR grafted antibodies, human antibodies and antibodies which include portions of CDR sequences specific for cdk1.

Neutralizing antibodies, i.e., those which may inhibit formation of the cyclinB1/cdk1 complex or inhibit binding of the complex to iASPP, are especially preferred. In a preferred embodiment, the antibody is a monoclonal antibody. In some embodiments, the antibody is a human or a humanized antibody. Techniques described elsewhere herein are useful for the preparation of antibodies for both detection and therapeutic purposes.

Various small molecule cdk1 inhibitors are currently undergoing clinical trials. See Malumbres et al., Nat. Rev. Canc. 9:153-166, 2009, Table 2 in particular. In some embodiments, the molecule that suppresses expression or signaling activity of cdk1 includes, but is not limited to AT-7519, P276-00, R547, Flavopiridol, UCN-01, BMS-387032, K00616A and CDKi277.

In some embodiments, the cdk1 inhibitor is an inhibitor provided below in Table 1.

TABLE 1

| Drug Name (CD, GN, BN) | Chemical Name/Description | Molecular Mechanism | Therapeutic Group | Mechanism of Action |
|---|---|---|---|---|
| Scytonemin | 3,3'-Bis(4-hydroxyphenylmethylene)-(1,1'-bicyclopent[b]indole)-2,2'-(3H,3'H)-dione | CDK1/Cyclin B1 Inhibitors | Oncolytic Drugs; Ultraviolet Light Absorbers | Antiinflammatory Drugs; Antimitotic Drugs; CDK1/Cyclin B1 Inhibitors; Checkpoint Kinase 1 (Chk1) Inhibitors; Inhibitors of Signal Transduction Pathways; Myt1 Kinase Inhibitors; Polo-like Kinase Inhibitors; Protein Kinase PKC beta 2 Inhibitors |
| | | Checkpoint Kinase 1 (Chk1) Inhibitors Myt1 Kinase Inhibitors Polo-like Kinase Inhibitors Protein Kinase PKC beta 2 Inhibitors | | |
| | N-[2-[2-[4-(N,N-Dimethylsulfamoyl)phenylamino]-5-ethylpyrimidin-4-ylamino]ethyl]acetamide hydrochloride | CDK1/Cyclin B1 Inhibitors | Oncolytic Drugs | CDK1/Cyclin B1 Inhibitors; Inhibitors of Signal Transduction Pathways |
| AZD-5438 | 4-(1-Isopropyl-2-methyl-1H-imidazol-5-yl)-N-[4-(methylsulfonyl)phenyl]pyrimidin-2-amine | CDK1/Cyclin B1 Inhibitors | Solid Tumors Therapy | CDK1/Cyclin B1 Inhibitors; CDK2/Cyclin A Inhibitors; CDK2/Cyclin E Inhibitors |
| | | CDK2/Cyclin A Inhibitors CDK2/Cyclin E Inhibitors | | |
| | 4-Butoxy-5-(phenylsulfinyl)-1H-pyrazolo[3,4-b]pyridine | CDK1/Cyclin B1 Inhibitors | Oncolytic Drugs | CDK1/Cyclin B1 Inhibitors; CDK2/Cyclin E Inhibitors; CDK4/Cyclin D1 Inhibitors; Inhibitors of Signal Transduction Pathways |
| | | CDK2/Cyclin E Inhibitors CDK4/Cyclin D1 Inhibitors | | |
| | 4-Butoxy-5-(phenylsulfonyl)-1H-pyrazolo[3,4-b]pyridine | CDK1/Cyclin B1 Inhibitors | Oncolytic Drugs | CDK1/Cyclin B1 Inhibitors; CDK2/Cyclin E Inhibitors; CDK4/Cyclin D1 Inhibitors; Inhibitors of Signal Transduction Pathways |
| | | CDK2/Cyclin E Inhibitors CDK4/Cyclin D1 Inhibitors | | |
| | 2-[4-[5-[2,6-Dimethoxy-4-[5-(3,4,5-trimethoxyphenyl)-4,5-dihydroisooxazol-3-yl]phenoxy]pentyloxy]-3-methoxyphenyl]-1,2,3,4-tetrahydroquinazolin-4-one | CDK1/Cyclin B1 Inhibitors | Oncolytic Drugs | Antimitotic Drugs; CDK1/Cyclin B1 Inhibitors; Tubulin polymerization inhibitors |
| | | Tubulin polymerization inhibitors | | |

TABLE 1-continued

| Drug Name (CD, GN, BN) | Organization | Condition | Related Basic Patent |
|---|---|---|---|
| | GlaxoSmithKline; University of California, Santa Barbara; | Cancer; Photosensitivity | US 2002022589; WO 2001062900 U.S. Pat. No. 6,495,586; Issued Dec. 17, 2002, Expired on Jan. 17, 2007; U.S. Pat. No. 6,495,588, Issued Dec. 17, 2002, Expired Jan. 17, 2007 |
| | Boehringer Ingelheim (Originator); | Cancer | WO 2003032997 |
| AZD-5438 | AstraZeneca (Originator); | Cancer, solid tumor | |
| | Bristol-Myers Squibb (Originator); | Cancer | WO 2001081348 |
| | Bristol-Myers Squibb (Originator); | Cancer | WO 2001081348 |
| | CSIR (IN) (Originator); | Cancer | WO 2010058417 |

In some embodiments, the therapeutic regimen comprises prescribing and/or administering an inhibitor of mdm2-induced degradation of p53 to the subject. Such inhibitors include, but are not limited to, Nutlin3, Nutlin3a, HL198C, benzodiazepines, spiro-oxindoles, quillinois and RITA. Various inhibitors of the p53-mdm2 interaction are known in the art and are described in Chene, Molec. Canc. Res., 2:20-28, 2004 and Vassilev et al., Trends Molec. Med., 13:23-31, 2006, the disclosure of which are incorporated herein by reference in their entireties. Such inhibitors include chalcone derivative (compound B-1, Stoll et al., Biochem., 2:336-344, 2001), polycyclic compound (compound cyc-2, Zhao et al., Cancer Lett., 2:69-77, 2002), chlorofusin (Duncan et al., J. Am. Chem., 2:554-560, 2001), and various peptide inhibitors (Ac-Gln-Glu-Thr-Phe-Ser-Asp-Leu-Trp-Lys-Lru-Leu-Pro-NH$_2$-SEQ ID NO: 7; Ac-Met-Pro-Arg-Phe-Met-Asp-Tyr-Trp-Glu-Gly-Leu-Asn-NH$_2$-SEQ ID NO: 8; Ac-Phe-Met-Asp-Tyr-Trp-Glu-Gly-Leu-Asn-NH$_2$-SEQ ID NO: 9; Ac-Glu-Thr-Phe-Aib-Asp-Aib-Trp-Lys-Aib-Leu-Aib-Glu NH$_2$-SEQ ID NO: 10; Ac-Phe-Met-Aib-Tyr-Trp-Glu-Ac3c-Leu-Asn-NH$_2$-SEQ ID NO: 11; Ac-Phe-Met-Aib-Pmp-Trp-Glu-Ac3c-Leu-Asn-NH$_2$-SEQ ID NO: 12; and Ac-Phe-Met-Aib-Pmp-6ClTrp-Glu-Ac3c-Leu-Asn-NH$_2$-SEQ ID NO: 13)

The therapeutic regimen optionally comprises prescribing and/or administering an inhibitor of B-RafV600E to the subject. Exemplary inhibitors are described in Wenglowsky et al, ACS Med. Chem., 2:342-347, 2011 and James et al., Mol. Cancer Ther., epub Feb. 7, 2012, the disclosure of which are incorporated herein by reference in their entireties and include, but are not limited to, Vemurafenib (also known as PLX-4032, RG7204 or RO5185426, marketed as Zelboraf™) and CEP-32496.

In some embodiments, the therapeutic regimen comprises prescribing a standard of care therapy to a mammalian subject in whom elevated iASPP phosphorylation and/or elevated iASPP nuclear localization is absent from the cancer cell.

V. Combination Therapy

Therapeutic compositions can be administered in therapeutically effective dosages alone or in combination with adjunct cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer. Cytostatic and cytotoxic agents that target the cancer cells are specifically contemplated for combination therapy. Likewise, agents that target angiogenesis or lymphangiogenesis are specifically contemplated for combination therapy.

As used herein, a "chemotherapeutic agent" is a chemical compound useful in the treatment of cancer. Examples of chemotherapeutic agents include: alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; antibiotics such as the enediyne antibiotics (e.g., calicheamicin, especially calicheamicin gammall and calicheamicin omegall;

L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASL® exemestane, formestane, fadrozole, RIVISOR® vorozole, FEMARA® letrozole, and ARTMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF-A expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rJL-2; LURTOTECAN® topoisomerase 1 inhibitor; ABARELLX® rmRH; and pharmaceutically acceptable salts, acids or derivatives of any of the above.

A "growth inhibitory agent" as used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Cytokines that are effective in inhibiting tumor metastasis are also contemplated for use in the combination therapy. Such cytokines, lymphokines, or other hematopoietic factors include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin.

The treatment methods described herein optionally include monitoring the effect of the therapeutic composition on the tumor. For example, the size of the tumor can be determined, as can the presence of metastases. These compositions would be provided in a combined amount effective to kill or inhibit proliferation of the cancer by killing and/or inhibiting the proliferation of the cancer cells. This process may involve contacting the cells with a agent that inhibits phosphorylation of iASPP and a further agent(s) at the same time. This may be achieved by contacting the cell with a single composition or pharmacological formulation that includes both agents, or by contacting the cell with two distinct compositions or formulations, at the same time, wherein one composition includes an agent that inhibits phosphorylation of iASPP or an iASPP inhibitor peptide and the other includes a second agent.

Combination therapy with an agent described herein may be achieved by administering to a subject a single composition or pharmacological formulation that includes the cdk1 inhibitor or inhibitor peptides and the one or more additional agents, or by administering to the subject two (or more) distinct compositions or formulations, at the same time, wherein one composition includes a cdk1 inhibitor or inhibitor peptides and the other includes a second agent.

Alternatively, the combination therapy employing a cdk1 inhibitor described herein may precede or follow the second agent treatment by intervals ranging from minutes to weeks.

In embodiments where the second agent and the cdk1 inhibitor are administered separately, one would generally ensure that a significant period of time did not expire between the times of each delivery, such that the agent and the cdk1 inhibitor would still be able to exert an advantageously combined effect. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. Repeated treatments with one or both agents is specifically contemplated.

VI. Pharmaceutical Compositions and Routes of Administration

Purified protein, antibodies, antagonists, or inhibitors may all be used as pharmaceutical compositions. Delivery of specific molecules for therapeutic purposes in this invention is further described below.

The active compositions of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramuscular, intramammary, intraperitoneal, intrathecal, intraocular, retrobulbar, intrapulmonary (e.g., term release); by oral, sublingual, nasal, anal, vaginal, or transdermal delivery, or by surgical implantation at a particular site, e.g., embedded under the splenic capsule, brain, or in the cornea. The treatment may consist of a single dose or a plurality of doses over a period of time.

For all protein-based therapeutics described herein (e.g., antibodies) administration by the delivery of gene expression constructs are contemplated as one embodiment. Any suitable vector may be used to introduce a polynucleotide that encodes a protein-based therapeutic described herein, into the host. Exemplary vectors that have been described in the literature include replication deficient retroviral vectors, including but not limited to lentivirus vectors [Kim et al., J. Virol., 72(1): 811-816 (1998); Kingsman & Johnson, Scrip Magazine, October, 1998, pp. 43 46.]; adeno-associated viral (AAV) vectors [U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479; Gnatenko et al., J. Invest. Med., 45: 87 98 (1997)]; adenoviral (AV) vectors [See, e.g., U.S. Pat. No. 5,792,453; U.S. Pat. No. 5,824,544; U.S. Pat. No. 5,707,618; U.S. Pat. No. 5,693,509; U.S. Pat. No. 5,670,488; U.S. Pat. No. 5,585,362; Quantin et al., Proc. Natl. Acad. Sci. USA, 89: 2581 2584 (1992); Stratford Perricadet et al., J. Clin. Invest., 90: 626 630 (1992); and Rosenfeld et al., Cell, 68: 143 155 (1992)]; an adenoviral adenoassociated viral chimeric (see for example, U.S. Pat. No. 5,856,152) or a vaccinia viral or a herpesviral (see for example, U.S. Pat. No. 5,879,934; U.S. Pat. No. 5,849,571; U.S. Pat. No. 5,830,727; U.S. Pat. No. 5,661,033; U.S. Pat. No. 5,328,688; Lipofectin mediated gene transfer (BRL); liposomal vectors [See, e.g., U.S. Pat. No. 5,631,237 (Liposomes comprising Sendai virus proteins)]; and combinations thereof. All of the foregoing documents are incorporated herein by reference in their entirety. Replication deficient adenoviral vectors constitute a preferred embodiment.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the active compositions may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions described herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

In the clinical setting an "effective amount" is an amount sufficient to effect beneficial or desired clinical results. An effective amount can be administered in one or more doses. In terms of treatment, an "effective amount" of a therapeutic agent described herein is an amount that results in amelioration of symptoms or a prolongation of survival in a subject. The effective amount is generally determined by the physician on a case-by-case basis and is within the skill of one in the art. Several factors are typically taken into account when determining, an appropriate dosage. These factors include age, sex and weight of the patient, the condition being treated, the severity of the condition. Determination of the effective amounts is well within the capability of those skilled in the art, especially in light of the detailed disclosure provided herein. For any therapeutic agent used in a method described herein, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the C-proteinase activity). Such information can be used to more accurately determine useful doses in humans.

Toxicity and therapeutic efficacy of such compounds can be determined by standard pharmaceutical procedures in cell cultures or experimental animals, e.g., for determining the $LD_{50}$ (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics," Ch. 1 p. 1. Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50-90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration. Refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials. As studies are conducted, further information will emerge regarding appropriate dosage levels and duration of treatment for specific diseases and conditions.

In a preferred embodiment, the present invention is directed at treatment of a cancer selected from the group consisting of melanoma, prostate cancer, head cancer and neck cancer, wherein the cancer expresses an elevated level of phosphorylated iASPP. A variety of different routes of administration are contemplated. For example, in the case of a tumor, the discrete tumor mass may be injected with a therapeutic agent described herein. The injections may be single or multiple; where multiple, injections are made at about 1 cm spacings across the accessible surface of the tumor. Further, systemic injection may be preferred.

The pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

VII. Kits

In another embodiment, kits are provided which contain the necessary reagents to carry out the assays or therapies of the present invention. In some variations, reagents are packaged together but not in admixture. In one embodiment, the invention provides a compartment kit to receive, in close confinement, one or more containers which comprises: (a) a first container comprising an antibody that specifically binds iASPP polypeptide and preferentially binds to iASPP having a phosphorylated serine residue compared to binding without the phosphorylated serine, wherein the serine residue corresponds to a serine selected from the group consisting of Ser84 and Ser113 of SEQ ID NO: 2; optionally (b) a second container comprising an antibody that specifically binds iASPP polypeptide, but does not bind to iASPP having the phosphorylated serine residue; and (c) one or more other containers comprising one or more of the following: wash reagents, reagents capable of detecting presence of a bound antibody.

In another embodiments, the invention provides a compartment kit to receive, in close confinement, one or more containers which comprises (a) a first container comprising an antibody that specifically binds iASPP; optionally (b) a second container comprising an antibody that specifically binds to iASPP having a phosphorylated serine residue compared to binding without the phosphorylated serine, wherein the serine residue corresponds to a serine selected from the group consisting of Ser84 and Ser113 of SEQ ID NO: 2; and (c) one or more other containers comprising one or more of the following: wash reagents, reagents capable of detecting presence of a bound antibody.

In further embodiments, the invention provides a compartment kit to receive, in close confinement, one or more containers which comprises (a) a first container comprising an antibody that specifically binds iASPP; optionally (b) a second container comprising an antibody that specifically binds iASPP polypeptide, but does not bind to iASPP having the phosphorylated serine residue and (c) one or more other containers comprising one or more of the following: wash reagents, reagents capable of detecting presence of a bound antibody.

The invention also provides, in some embodiments, a compartment kit to receive, in close confinement, one or more containers which comprises (a) a first container comprising an antibody that specifically binds iASPP; (b) a second container comprising an antibody that specifically binds to iASPP having a phosphorylated serine residue compared to binding without the phosphorylated serine, wherein the serine residue corresponds to a serine selected from the group consisting of Ser84 and Ser113 of SEQ ID NO: 2; and optionally (c) a third container comprising an antibody that specifically binds iASPP polypeptide, but does not bind to iASPP having the phosphorylated serine residue and (d) one or more other containers comprising one or more of the following: wash reagents, reagents capable of detecting presence of a bound antibody.

In some embodiments, described herein is a compartment kit to receive, in close confinement (such as a single box or package, one or more containers which comprises (a) a first container comprising a first antibody that binds an iASPP polypeptide, (b) a second container comprising a second antibody that binds a region of iASPP that includes Ser84 or Ser113 of iASPP (SEQ ID NO: 2) and selectively binds iASPP when said serine in said epitope is unphosphorylated, and wherein the second binding partner optionally comprises a detectable label; (c) one or more other containers comprising one or more of the following: wash reagents, reagents capable of detecting presence of a bound antibody; and optionally (d) a third container comprising a nucleus specific marker.

In another embodiment, the invention provides a compartment kit to receive, in close confinement, one or more containers which comprises (a) a first container comprising an antibody that specifically binds iASPP; optionally (b) a second container comprising an antibody that specifically binds to iASPP having a phosphorylated serine residue compared to binding without the phosphorylated serine, wherein the second antibody comprises a detectable label; (c) one or more other containers comprising one or more of the following: wash reagents, reagents capable of detecting presence of a bound antibody; and optionally (d) a third container comprising a nucleus specific marker.

In detail, a compartment kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibody or antibodies used in the assay, containers which contain wash reagents (such as phosphate-buffered saline, Tris buffers, and the like), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed antibodies of the present invention can be readily incorporated into one of the established kit formats which are well known in the art.

In further detail, kits for use in measuring phosphorylated iASPP in a sample can include a first antibody or functional fragment thereof which binds to iASPP (both phosphorylated and unphosphorylated forms) or portion of this iASPP, a second antibody or functional fragment thereof that specifically binds phosphorylated iASPP or a portion of the phosphorylated iASPP as well as one or more ancillary reagents suitable for detecting the presence of a complex between the antibodies (or fragment) and iASPP or portion thereof. The antibody compositions can be provided in lyophilized form, either alone or in combination with additional antibodies specific for other epitopes. The antibodies, which can be labeled or unlabeled, can be included in the kits with adjunct ingredients. For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

In some embodiments, the kits described herein are packaged with nuclear marker reagents.

VI. Diagnostic Systems

Another aspect of the invention is a system that is capable of carrying out a part or all of a method of the invention, or carrying out a variation of a method of the invention as described herein in greater detail. Exemplary systems include, as one or more components, computing systems, environments, and/or configurations that may be suitable for use with the methods and include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like. In some variations, a system of the invention includes one or more machines used for analysis of biological material (e.g., genetic material), as described herein. In some variations, this analysis of the biological material involves a chemical analysis and/or a nucleic acid amplification.

Figure 15:
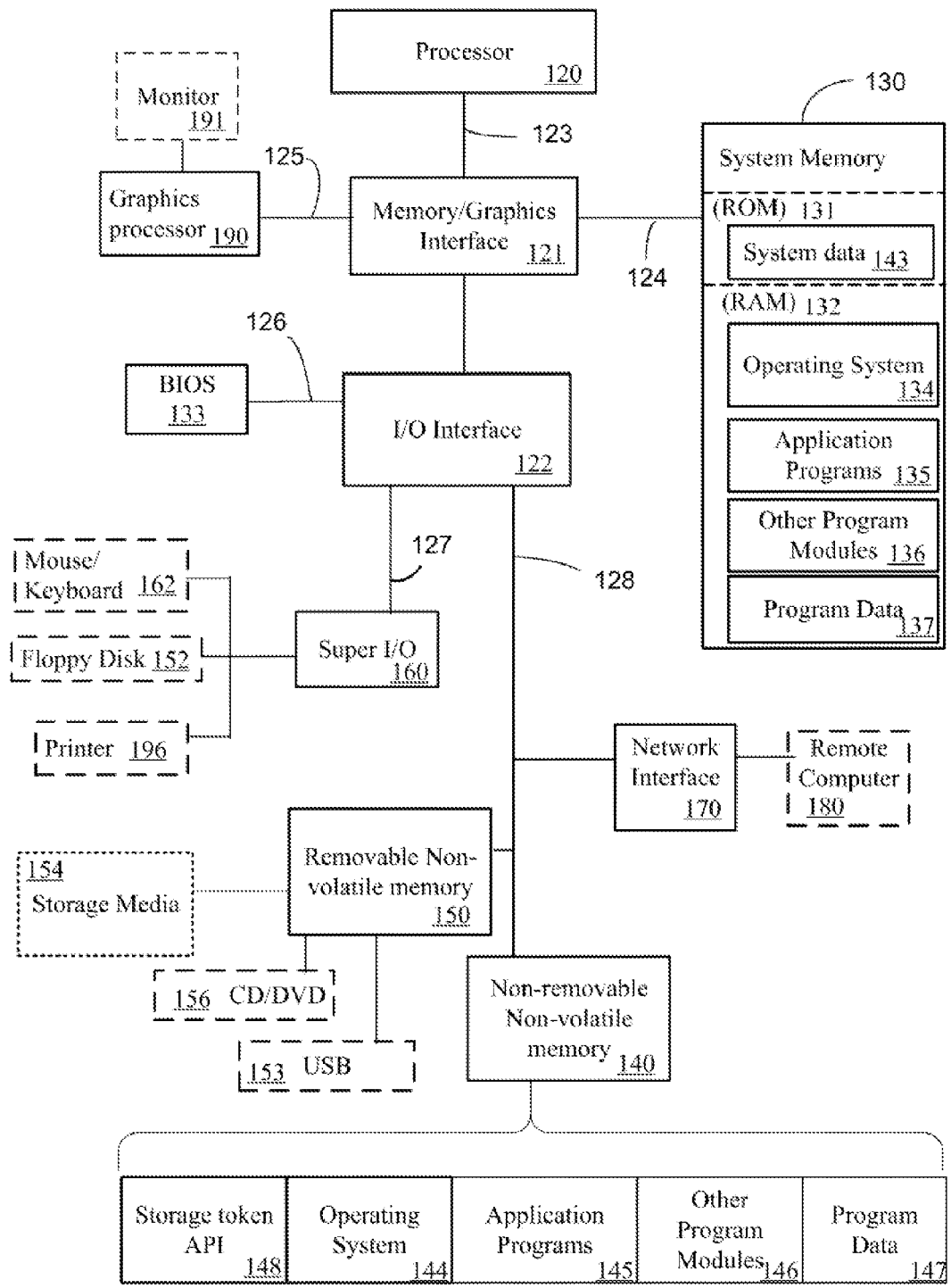
FIG. 15 is an exemplary system comprising exemplary computer components.

With reference to FIG. 15, an exemplary system of the invention, which may be used to implement one or more steps of methods of the invention, includes a computing device in the form of a computer 110. Components shown in dashed outline are not technically part of the computer 110, but are used to illustrate the exemplary embodiment of FIG. 15. Components of computer 110 may include, but are not limited to, a processor 120, a system memory 130, a memory/graphics interface 121, also known as a Northbridge chip, and an I/O interface 122, also known as a Southbridge chip. The system memory 130 and a graphics processor 190 may be coupled to the memory/graphics interface 121. A monitor 191 or other graphic output device may be coupled to the graphics processor 190.

A series of system busses may couple various system components including a high speed system bus 123 between the processor 120, the memory/graphics interface 121 and the I/O interface 122, a front-side bus 124 between the memory/graphics interface 121 and the system memory 130, and an advanced graphics processing (AGP) bus 125 between the memory/graphics interface 121 and the graphics processor 190. The system bus 123 may be any of several types of bus structures including, by way of example, and not limitation, such architectures include Industry Standard Architecture (ISA) bus, Micro Channel Architecture (MCA) bus and Enhanced ISA (EISA) bus. As system architectures evolve, other bus architectures and chip sets may be used but often generally follow this pattern. For example, companies such as Intel and AMD support the Intel Hub Architecture (IHA) and the Hypertransport™ architecture, respectively.

The computer 110 typically includes a variety of computer-readable media. Computer-readable media can be any available media that can be accessed by computer 110 and includes both volatile and nonvolatile media, removable and non-removable media. By way of example, and not limitation, computer readable media may comprise computer storage media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other physical medium which can be used to store the desired information and which can accessed by computer 110.

The system memory 130 includes computer storage media in the form of volatile and/or nonvolatile memory such as read only memory (ROM) 131 and random access memory (RAM) 132. The system ROM 131 may contain permanent system data 143, such as identifying and manufacturing information. In some embodiments, a basic input/output system (BIOS) may also be stored in system ROM 131. RAM 132 typically contains data and/or program modules that are immediately accessible to and/or presently being operated on by processor 120. By way of example, and not limitation, FIG. 15 illustrates operating system 134, application programs 135, other program modules 136, and program data 137.

The I/O interface 122 may couple the system bus 123 with a number of other busses 126, 127 and 128 that couple a variety of internal and external devices to the computer 110. A serial peripheral interface (SPI) bus 126 may connect to a basic input/output system (BIOS) memory 133 containing the basic routines that help to transfer information between elements within computer 110, such as during start-up.

A super input/output chip 160 may be used to connect to a number of 'legacy' peripherals, such as floppy disk 152, keyboard/mouse 162, and printer 196, as examples. The super I/O chip 160 may be connected to the I/O interface 122 with a bus 127, such as a low pin count (LPC) bus, in some embodiments. Various embodiments of the super I/O chip 160 are widely available in the commercial marketplace.

In one embodiment, bus 128 may be a Peripheral Component Interconnect (PCI) bus, or a variation thereof, may be used to connect higher speed peripherals to the I/O interface 122. A PCI bus may also be known as a Mezzanine bus. Variations of the PCI bus include the Peripheral Component Interconnect-Express (PCI-E) and the Peripheral Component Interconnect-Extended (PCI-X) busses, the former having a serial interface and the latter being a backward compatible parallel interface. In other embodiments, bus 128 may be an advanced technology attachment (ATA) bus, in the form of a serial ATA bus (SATA) or parallel ATA (PATA).

The computer 110 may also include other removable/non-removable, volatile/nonvolatile computer storage media. By way of example only, FIG. 15 illustrates a hard disk drive 140 that reads from or writes to non-removable, nonvolatile magnetic media. The hard disk drive 140 may be a conventional hard disk drive.

Removable media, such as a universal serial bus (USB) memory 153, firewire (IEEE 1394), or CD/DVD drive 156 may be connected to the PCI bus 128 directly or through an interface 150. A storage media 154 may coupled through interface 150. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like.

The drives and their associated computer storage media discussed above and illustrated in FIG. 15, provide storage of computer readable instructions, data structures, program modules and other data for the computer 110. In FIG. 15, for example, hard disk drive 140 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a mouse/keyboard 162 or other input device combination. Other input devices (not shown) may include a microphone, joystick, game pad, satellite dish, scanner, or the like. These and other input devices are often connected to the processor 120 through one of the I/O interface busses, such as the SPI 126, the LPC 127, or the PCI 128, but other busses may be used. In some embodiments, other devices may be coupled to parallel ports, infrared interfaces, game ports, and the like (not depicted), via the super I/O chip 160.

The computer 110 may operate in a networked environment using logical connections to one or more remote computers, such as a remote computer 180 via a network interface controller (NIC) 170. The remote computer 180 may be a personal computer, a server, a router, a network PC, a peer device or other common network node, and typically includes many or all of the elements described above relative to the computer 110. The logical connection between the NIC 170 and the remote computer 180 depicted in FIG. 15 may include a local area network (LAN), a wide area network (WAN), or both, but may also include other networks. Such networking environments are commonplace in offices, enterprise-wide computer networks, intranets, and the Internet. The remote computer 180 may also represent a web server supporting interactive sessions with the computer 110, or in the specific case of location-based applications may be a location server or an application server.

In some embodiments, the network interface may use a modem (not depicted) when a broadband connection is not available or is not used. It will be appreciated that the network connection shown is exemplary and other means of establishing a communications link between the computers may be used.

In some variations, the invention is a system for identifying susceptibility to a cancer in a human subject. For example, in one variation, the system includes tools for performing at least one step, preferably two or more steps, and in some aspects all steps of a method of the invention, where the tools are operably linked to each other. Operable linkage describes a linkage through which components can function with each other to perform their purpose.

In some variations, a system of the invention is a system for identifying metastatic potential of a cancer in a human subject, the system comprising:

(a) at least one processor;
(b) at least one computer-readable medium;
(c) a database operatively coupled to a computer-readable medium of the system and containing population information correlating the phosphorylation state of iASPP in cancer and metastasis data in a population of humans;
(d) a measurement tool that receives an input about the human subject and generates information from the input about the iASPP phosphorylation in a cancer cell from the human subject; and
(e) an analysis tool or routine that:
(i) is operatively coupled to the database and the measurement tool,
(ii) is stored on a computer-readable medium of the system,
(iii) is adapted to be executed on a processor of the system, to compare the information about the human subject with the population information in the susceptibility database and generate a conclusion with respect to susceptibility to metastatic potential of the cancer in the human subject.

Exemplary processors (processing units) include all variety of microprocessors and other processing units used in computing devices. Exemplary computer-readable media are described above. When two or more components of the system involve a processor or a computer-readable medium, the system generally can be created where a single processor and/or computer readable medium is dedicated to a single component of the system; or where two or more functions share a single processor and/or share a single computer readable medium, such that the system contains as few as one processor and/or one computer readable medium. In some variations, it is advantageous to use multiple processors or media, for example, where it is convenient to have components of the system at different locations. For instance, some components of a system may be located at a testing laboratory dedicated to laboratory or data analysis, whereas other components, including components (optional) for supplying input information or obtaining an output communication, may be located at a medical treatment or counseling facility (e.g., doctor's office, health clinic, HMO, pharmacist, geneticist, hospital) and/or at the home or business of the human subject (patient) for whom the testing service is performed.

Figure 16:
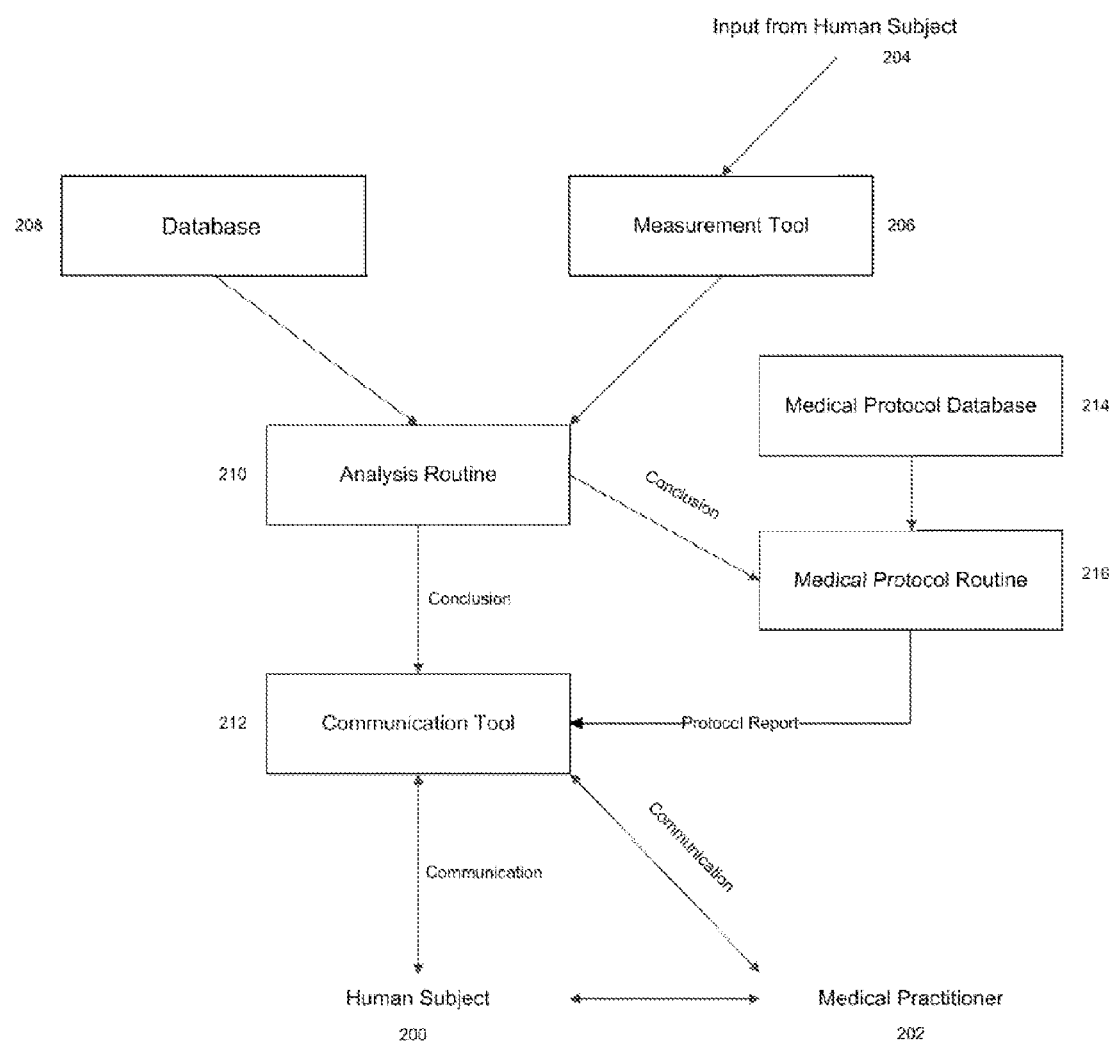
FIG. 16 is a flow chart depicting system components and operation.

Referring to FIG. 16 an exemplary system includes a database 208 that is operatively coupled to a computer-readable medium of the system and that contains population information correlating the phosphorylation state of iASPP and metastatic potential of a cancer in a population of humans. For example, for a statistically meaningful number of cancer subjects, information is collected as to whether the cancer was metastatic and as to whether (or what percentage) of the cells have iASPP that was phosphorylated or localized to the nucleus.

In a simple variation, the database contains 208 data relating to the level of phosphorylated iASPP observed in cancer cells of a population of humans with the cancer and information about the metastatic behavior of the cancer. Such data provides an indication as to the potential of developing metastatic cancer for a human subject that is identified as expressing phosphorylated iASPP. In another variation, the database optionally includes similar data with respect to a level of iASPP within the nucleus of a cancer cell compared to a level of iASPP in the cytoplasm of the cancer cell. In still another variation, the database includes additional quantitative personal, medical, or genetic information about the individuals in the database with non-metastatic, metastatic, or aggressively metastatic cancer (or control individuals free of the cancer). As the database becomes more populated with patient data, it become a more powerful statistical tool for comparing an input with respect to a subject and making a prediction as to metastatic potential. Such information includes, but is not limited to, information about parameters such as age, sex, ethnicity, race, medical history, weight, diabetes status, blood pressure, family history of the cancer, smoking history, and alcohol use in humans and impact of the at least one parameter on metastatic potential of the cancer. These more robust databases can be used by an analysis routine 210 to calculate a combined score with respect to potential for a cancer to metastasize.

In addition to the database 208, the system further includes a measurement tool 206 programmed to receive an input 204 from or about the human subject and generate an output that contains information about the phosphorylation state of iASPP. (The input 204 is not part of the system per se but is illustrated in the schematic FIG. 16.) Thus, the input 204 will contain a specimen or contain data from which a level of phosphorylated iASPP in a cancer cell (or a level of iASPP within the nucleus of a cancer cell) can be directly read, or analytically determined.

In another variation, the input 204 from the human subject contains data that is unannotated or insufficiently annotated with respect to iASPP, requiring analysis by the measurement tool 206. For example, the input can be raw data measurements from experiments designed to evaluate phosphorylation or localization of iASPP. In such variations, the measurement tool 206 comprises a tool, preferably stored on a computer-readable medium of the system and adapted to be executed on a processor of the system, to receive a data input about a subject and determine information about the iASPP phosphorylation state from the data. For example, the measurement tool 206 contains instructions, preferably executable on a processor of the system, for analyzing the unannotated input data and determining the level of iASPP phosphorylation of interest in the human subject.

In yet another variation, the input 204 from the human subject comprises a biological sample, such as a fluid (e.g., blood) or tissue sample, that contains one or more cancer cells or iASPP protein that can be analyzed to determine the iASPP phosphorylation state. In this variation, an exemplary measurement tool 206 includes laboratory equipment for processing and analyzing the sample to determine the iASPP phosphorylation state in cancer cells of the human subject.

In some variations the measurement tool 206 includes: immunoassay reagents for measuring iASPP and measuring iASPP phosphorylation from cells in the biological sample; and an analysis tool stored on a computer-readable medium of the system and adapted to be executed on a processor of the system, to determine the level of phosphorylated iASPP based on the immunoassay data.

In some variations, the measurement tool 206 further includes additional equipment and/or chemical reagents for processing the biological sample to purify iASPP from cells in a sample for further analysis using immunoassays, size separation tools, or other analytical equipment.

The exemplary system further includes an analysis tool or routine 210 that: is operatively coupled to the database 208 and operatively coupled to the measurement tool 206, is stored on a computer-readable medium of the system, is adapted to be executed on a processor of the system to compare the information about the human subject with the population information in the database 208 and generate a conclusion with respect to metastatic potential of cancer in the human subject. In simple terms, the analysis tool 210 looks at the level of phosphorylated iASPP identified by the measurement tool 206 for the human subject, and compares this information to the database 208, to determine metastatic potential of a cancer in the subject. The susceptibility can be based on the single parameter (the level of phosphorylated iASPP), or can involve a calculation based on other genetic and non-genetic data, as described above, that is collected and included as part of the input 204 from the human subject, and that also is stored in the database 208 with respect to a population of other humans. Generally speaking, each parameter of interest is weighted to provide a conclusion with respect to metastatic potential of the cancer. Such a conclusion is expressed in the conclusion in any statistically useful form, for example, as an odds ratio or a probability that the subject's cancer is a metastatic form of the cancer (or has high potential for metastasis).

In some variations, the system as just described further includes a communication tool 212. For example, the communication tool is operatively connected to the analysis routine 210 and comprises a routine stored on a computer-readable medium of the system and adapted to be executed on a processor of the system, to: generate a communication containing the conclusion; and to transmit the communication to the human subject 200 or the medical practitioner 202, and/or enable the subject or medical practitioner to access the communication. (The subject and medical practitioner are depicted in the schematic FIG. 17, but are not part of the system per se, though they may be considered users of the system. The communication tool 212 provides an interface for communicating to the subject, or to a medical practitioner for the subject (e.g., doctor, nurse, genetic counselor), the conclusion generated by the analysis tool 210 with respect to metastatic potential of a cancer in the subject. Usually, if the communication is obtained by or delivered to the medical practitioner 202, the medical practitioner will share the communication with the human subject 200 and/or counsel the human subject about the medical significance of the communication. In some variations, the communication is provided in a tangible form, such as a printed report or report stored on a computer readable medium such as a flash drive or optical disk. In some variations, the communication is provided electronically with an output that is visible on a video display or audio output (e.g., speaker). In some variations, the communication is transmitted to the subject or the medical practitioner, e.g., electronically or through the mail. In some variations, the system is designed to permit the subject or medical practitioner to access the communication, e.g., by telephone or computer. For instance, the system may include software residing on a memory and executed by a processor of a computer used by the human subject or the medical practitioner, with which the subject or practitioner can access the communication, preferably securely, over the internet or other network connection. In some variations of the system, this computer will be located remotely from other components of the system, e.g., at a location of the human subject's or medical practitioner's choosing.

In some variations, the system as described (including embodiments with or without the communication tool) further includes components that add a treatment or prophylaxis utility to the system. For instance, value is added to a determination of metastatic potential of a cancer when a medical practitioner can prescribe or administer a standard of care that can reduce the metastatis potential of the cancer; and/or delay onset of the metastasis to facilitate early treatment and is most curable. Exemplary medicinal and surgical intervention protocols include administration of pharmaceutical agents for prophylaxis; and surgery, including in extreme cases surgery to remove a tissue or organ before the cancer within the organ metastasizes. Exemplary diagnostic protocols include non-invasive and invasive imaging; monitoring metabolic biomarkers; and biopsy screening.

For example, in some variations, the system further includes a medical protocol database 214 operatively connected to a computer-readable medium of the system and containing information correlating the iASPP phosphorylation state and medical protocols for human subjects with the cancer. Such medical protocols include any variety of medicines, lifestyle changes, diagnostic tests, increased frequencies of diagnostic tests, and the like that are designed to achieve effective therapy sith minimum side effects. The information correlating the iASPP phosphorylation state with protocols could include, for example, information about the success with which the metastatic cancer is avoided or delayed, if a subject has a level of phosphorylated iASPP and follows a protocol.

By way of example, in some variations, a system that analyzes inputs of iASPP phosphorylation (or iASPP intracellular localization) and at least one parameter selected from the group consisting of: a p53 mutation that reduces a tumor suppressive function of p53, an elevated measurement of mdm2 protein or mRNA, and a B-RafV600E mutation, or assessing the metastatic potential of the cancer could generate a variety of treatment protocols, including:

for a subject with a cancer characterized by elevated iASPP phosphorylation and/or iASPP nuclear localization, prescribing and/or administering a therapeutic regimen that includes an inhibitor of iASPP phosphorylation;

a therapeutic regimen that includes an inhibitor of iASPP phosphorylation and an inhibitor of mdm2-induced degradation of p53, for a subject with a cancer characterized by elevated iASPP phosphorylation and/or iASPP nuclear localization and the absence of a p53 mutation that reduces the tumor suppressive function of p53;

a therapeutic regimen that includes an inhibitor of iASPP phosphorylation and an inhibitor B-RafV600E, for a subject with a cancer characterized by elevated iASPP phosphorylation and/or iASPP nuclear localization and the presence of the B-Raf-V600E mutation;

a therapeutic regimen that includes all three of the foregoing agents, for a subject with a cancer that characterized by elevated iASPP phosphorylation and/or iASPP nuclear localization, the absence of a p53 mutation that reduces the tumor suppressive function of p53, and the presence of the B-Raf-V600E mutation.

The system of this embodiment further includes a medical protocol tool or routine 216, operatively connected to the medical protocol database 214 and to the analysis tool or routine 210. The medical protocol tool or routine 216 preferably is stored on a computer-readable medium of the system, and adapted to be executed on a processor of the system, to: (i) compare (or correlate) the conclusion that is obtained from the analysis routine 210 (with respect to metastatic potential of the cancer in the subject) and the medical protocol database 214, and (ii) generate a protocol report with respect to the probability that one or more medical protocols in the medical protocol database will achieve one or more of the goals of eliminating the cancer, slowing cancer growth or metastasis, and minimizing deleterious side effects of cancer treatment.

Some variations of the system just described include the communication tool 212. In some examples, the communication tool generates a communication that includes the protocol report in addition to, or instead of, the conclusion with respect to metastatic potential.

Information about the phosphorylation state of iASPP not only can provide useful information about identifying or quantifying potential for metastasis; it can also provide useful information about possible causative factors for a human subject identified with a cancer, and useful information about therapies for the cancer patient. In some variations, systems of the invention are useful for these purposes.

For instance, in some variations the invention is a system for assessing or selecting a treatment protocol for a subject diagnosed with a cancer. An exemplary system, schematically depicted in FIG. 17, comprises:

(a) at least one processor;
(b) at least one computer-readable medium;
(c) a medical treatment database 308 operatively connected to a computer-readable medium of the system and containing information correlating the phosphorylation state of iASPP and metastatic potential of the cancer;

(d) a measurement tool 306 to receive an input (304, depicted in FIG. 17 but not part of the system per se) about the human subject and generate information from the input 304 about the phosphorylation state of iASPP indicative of metastatic potential in a human subject diagnosed with the cancer; and (e) a medical protocol routine or tool 310 operatively coupled to the medical treatment database 308 and the measurement tool 306, stored on a computer-readable medium of the system, and adapted to be executed on a processor of the system, to compare the information with respect to the iASPP phosphorylation state in a cancer cell of the subject and the medical treatment database, and generate a conclusion with respect to at least one of:

(i) the probability that one or more medical treatments will be efficacious for treatment of the cancer for the patient; and (ii) which of two or more medical treatments for the cancer will be more efficacious for the patient.

Figure 17:
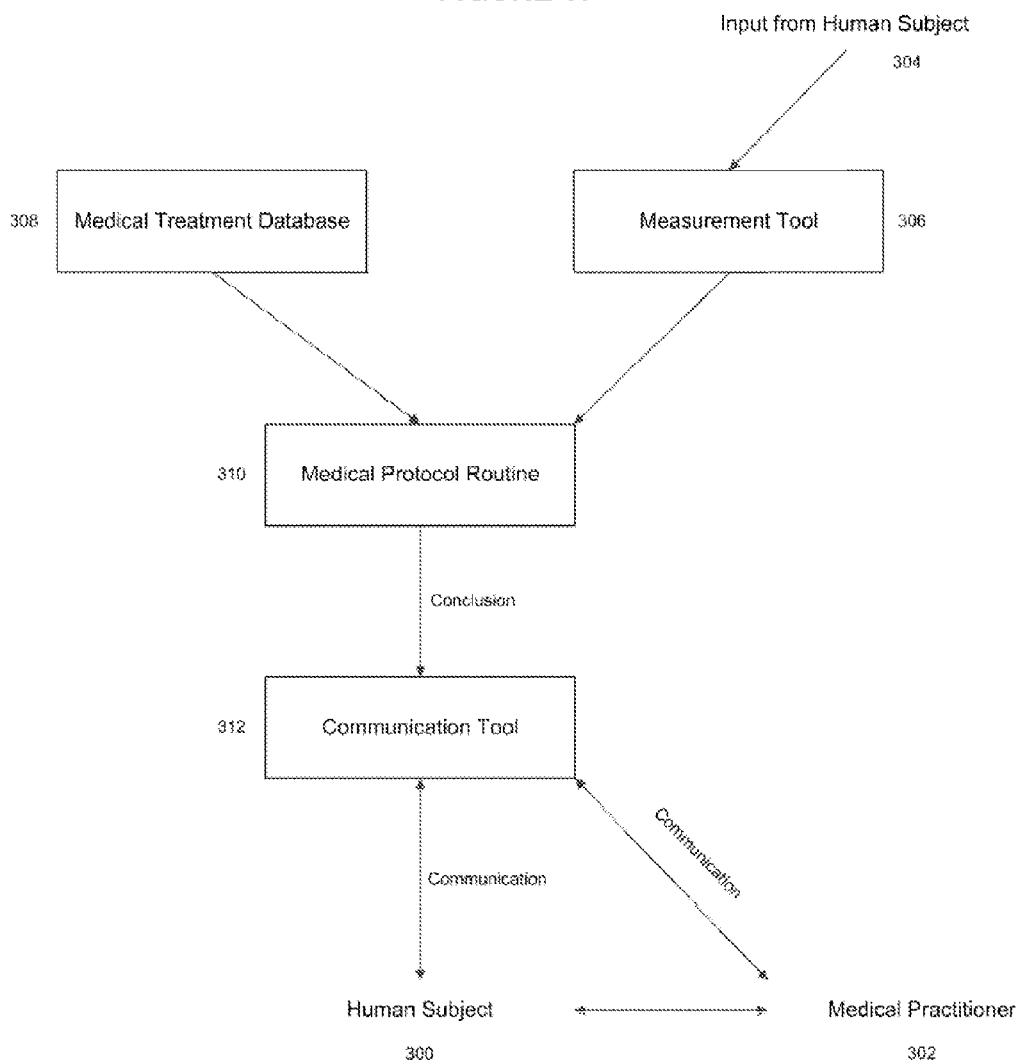
FIG. 17 is another flow chart depicting system components and operation.

Preferably, such a system further includes a communication tool 312 operatively connected to the medical protocol tool or routine 310 for communicating the conclusion to the subject 300, or to a medical practitioner for the subject 302 (both depicted in the schematic of FIG. 17, but not part of the system per se). An exemplary communication tool comprises a routine stored on a computer-readable medium of the system and adapted to be executed on a processor of the system, to generate a communication containing the conclusion; and transmit the communication to the subject or the medical practitioner, or enable the subject or medical practitioner to access the communication.

As described herein, information regarding iASPP phosphorylation state can be advantageously combined with other biological information about a cancer to improve evaluation of metastatic potential, and to improve selection of treatment regimen. Such information includes, for example, whether the cancer contains wild type p53 or a p53 mutation that reduces a tumor suppressive function of p53; whether the cancer expresses elevated amounts of mdm2, and whether the cancer contains a V600E mutation in B-Raf.

Accordingly, in some variations, the system of the invention has a measurement tool that receives an input about the human subject and generates information from the input about the presence or absence of one or more parameters selected from: a p53 mutation that reduces a tumor suppressive function of p53, an elevated measurement of mdm2 protein or mRNA, and a B-RafV600E mutation; the system has a database that contains population information correlating these parameters to metastasis data and/or treatment data; the system has an analysis tool or routine that compares the information about the human subject relating to iASPP phosphorylation and the one or more additional parameters; and the system generates a conclusion with respect to metastatic potential of the cancer and/or a treatment regimen for the cancer, using each of the two or more types of information collected by the system.

All publications and patents mentioned herein are hereby incorporated by reference in their entirety as if each individual publication or patent was specifically and individually indicated to be incorporated by reference. In case of conflict, the present application, including any definitions herein, will control.

The invention may be more readily understood by reference to the following examples, which are given to illustrate the invention and not in any way to limit its scope.

EXAMPLES

Example 1—Materials and Methods

Plasmids, Antibodies, and Cell Lines.

For protein purification pET22 plasmids encoding C-terminus of iASPP (625-828) and ASPP2 (905-1128) with His tag were kind gift from Ross Alexander Robinson (University of Oxford). cDNA encoding N-terminus of iASPP (1-240 aa and 249-482 aa) with GST tag were cloned in to pGEX between BamHI and EcoRI sites. These constructions were expressed in bacteria and purified by nickle beads or glutathione beads according to general protocols. Purified cylinB1/cdk1 complex and histone H1 were kindly given by Jane Endicott (University of Oxford). For transfected plasmids, fragments of iASPP and ASPP2 were cloned into construction using pcDNA3.1N5-His TOPO TA Expression Kit (Invitrogen). Primary antibodies are from: Self-made (LX-series antibodies), Santa Cruz (His (sc-803), p53 (sc-126), p63 (BC4A4)), Serotec (V5 (MCA1360)), and Cell signaling (cleaved PARP (9541), total PARP(9532), cleaved Caspase-3 (9661S), total Caspase-3 (9662)).

Most of cell lines were available in our lab store. IGR37 and IGR39 were kindly given by prof. Colin (University of Oxford). Prostate cancer cell lines were collected by Dr Richard (University of Oxford). iASPP knock out MEFs were prepared from embryonic day 13.5 embryos derived from iASPP knock out mice (Notari et al., 2011), and immortalized by Ras/E1A transforming.

Western Blotting (WB) and Immunoprecipitation:

For WB, cells were lysed in buffer containing 8 M urea, 1 M thiourea, 0.5% CHAPS, 50 mM DTT, and 24 mM spermine. A total of 40 µg of protein extract was loaded per lane into SDS-polyacrylamide gels. Gels were transferred onto nitrocellulose membrane (Protran) and the resulting blots incubated first with primary antibody overnight at 4° C. and then with the appropriate secondary horseradish peroxidize-conjugated antibody (Dako). The results were visualized by enhanced chemiluminescent detection (Amersham Biosciences) using X-ray film (Fujifilm). For cell lysate immunoprecipitation, cells were dissolved in NP40 buffer (50 mM Tris-HCl pH 8.0, 150 mM NaCl, 1% NP-40) with protease inhibitor cocktail mix (Roche Diagnostics). Cells were further thoroughly broken by ultrasonication, followed by spinning for 1 hour. Achieved suspension was adjusted to 1-2 mg/ml using NP40 buffer and incubated with 20 µl nickel beads, glutathione beads, or protein A beads (with 2 µg required antibody) for 2 h at room temperature. The beads were washed for four times with NP40 buffer, boiled for 5 min in Laemmli sample buffer, and applied for Western blotting. For pure protein immunoprecipitation, 5-10 µg purified proteins were mixed in NP40 buffer with 1 mg/ml BSA for 2 h at room temperature.

p53 Sequencing:

Total mRNA was extracted from melanoma cell pellets using Qiagen RNeasy Mini-Kit (Cat No 74104). cDNA was then amplified according to protocol for Invitrogen SuperScriptIII Reverse Transcriptase (Cat No 18080). Full length p53 were amplified from 5 µl cDNA using primers p53-1F (5'-CGGGGACACTTTGCGTTC-3' SEQ ID NO: 3) and p53-1R (5'-TTCTGACGCACACCTATTGC-3' SEQ ID NO: 4). The PCR product was sequenced using primers p53-2F (5'-GCTTTCCACGACGGTGAG-3' SEQ ID NO: 5) and p53-2R (5'-CAAGGGTTCAAAGACCCAAA-3' SEQ ID NO: 6).

In Vitro Cyclin B1/Cdk1 Assay:

5 µg iASPP fragment was incubated with 100 ng cyclin B1/cdk1 complex and 1 µCi [γ-32P]-ATP in kinase assay buffer for 10 min at room temperature. Reaction was stopped by SDS running buffer and subjected for SDS-PAGE gel. After electrophoresis, gels were fixed, dried and subjected to autoradiography.

FITC Protein Labeling and In Vitro Nuclear Import Assay:

Purified proteins were labeled with FITC according to protocol from protein label kit (F-6434, Invitrogen). Permeabilization and in vitro import assay were mainly carried out as described (Van Impe et al., 2008): digitonin treated semi-permeable cells (pre-seed on coverslides) were incubated in NIB buffer with 0.02 mg/ml FITC labelled substrate and 10 mg/ml H1299 cytoplasm factors at RT for 40 min. The cellular localization of the substrate was determined by direct fluorescence observation under confocol microscope. NIB buffer: (20 mM HEPES, pH 7.3, 110 mM potassium acetate, 5 mM sodium acetate, 2 mM magnesium acetate, 2 mM DTT, 0.5 mM EGTA and protease inhibitors). For iASPP(1-240) pretreated experiment, 0.02 mg/ml FITC labeled substrates were incubated with 0-1 mg/ml iASPP(1-240) at room temperature for 2 hours, followed by nuclear import assay.

Tissue Section Staining and Cell Immunofluorescence Staining:

As described in Notari et al., 2011, the disclosure of which is incorporated by reference in its entirety. Briefly, Tissue sections were dewaxed, rehydrated and incubated with 3% hydrogen peroxide in methanol to block endogenous peroxidase activity (10 mins). Prior to this incubation, antigen retrieval was carried out in microwaved sodium citrate buffer (pH 6.0) for 10 mins for cyclin B1 staining only. Sections were then blocked with normal goat serum (NGS), incubated overnight at 4° C. with the primary antibody, followed by the biotinylated secondary antibody for 40 minutes at room temperature. The Avidin-Biotin immunoperoxidase-Complex Vectastain Elite Reagent was used to amplify the signal and the peroxidase substrate Vector VIP was used to visualize the complexes. The sections were then counterstained with Methyl Green, dehydrated, permanently mounted and photographed. The expression of iASPP in the nucleus was scored as the product of staining intensity (0—none, 1—weak, 2—moderate, 3—strong) and the proportion of cells exhibiting this stain (0-100% in 5-10% increments) used to generate an Overall Expression score (0-300). All tumor cells showed cyclin B1 expression so expression levels were compared using an intensity score only (1-weak, 2-moderate, 3-strong).

Statistical analysis was undertaken in SPSS. Differences between groups were analysed by the Mann-Whitney test (U) where the effect size is denoted by $r=z/\sqrt{n}$ ($>0.3$=medium effect, $>0.5$=large effect). The relationship between nuclear iASPP, dichotomized around the upper quartile, in primary and metastatic tumors was evaluated using a Chi-squared test where the effect size is determined by the odds ratio. For survival analysis, a multivariate Cox proportional hazards model was used, controlling for known prognostic factors (age, gender, site, thickness, ulceration).

Mass Spectrometry Assay.

Isolated gel bands were subjected to trypsin digestion as described previously (Batycka et al., 2006). For the analysis of digested protein material, liquid chromatography was performed using an Ultimate 3000 nano-HPLC system (Dionex). Samples were concentrated on a trapping column (LC Packings, 300 µm ID, 0.1 cm) at a flow rate of 25 µl/min. For the separation with a C18 Pepmap column (75 μm ID, 15 cm, LC Packings), a flow rate of 300 nl/min was used as generated by a cap-flow splitter cartridge (1/300). Peptides were eluted by the application of a 30 min linear gradient: solvent A (95% H2O, 5% acetonitrile, 0.1% formic acid), 0-45% solvent B (95% acetonitrile, 5% water, 0.1% formic acid). LC was interfaced directly with a 3D high capacity ion trap mass spectrometer (HCTultra, Bruker Daltonics) utilizing 10 μm ID distal coated SilicaTips (New Objective) and nano-ESI mode. MS/MS analysis was initiated on a contact closure signal triggered by HyStar™ software. Up to 4 precursor ions were selected per cycle with active exclusion (0.5 min.). Raw LC-MS/MS data were processed and Mascot compatible files created using DataAnalysis 3.4 software (Bruker Daltonics). The MS/MS data representing phophorylated peptides was inspected manually and was performed according to published guidelines (Kamath et al., 2011).

Generation and Epitope Mapping of Mouse Monoclonal Anti-iASPP Antibody.

The immunogen used to generate iASPP mouse monoclonal antibodies LX49.3 and LX128.1-10 were human iASPP (439-639)-His fragment and human iASPP (1-240)-GST fragment, respectively. To map their epitopes, iASPP peptides were coated in 96-well plate and probed with above antibodies. The peptides recognized by LX 49.3, LX128.1, LX128.5, LX128.6, LX128.7, LX128.8, and LX128.9 were as follows: iASPP (501-510), iASPP (111-120), iASPP (111-122), iASPP (36-45), iASPP (36-45), iASPP (96-105), and iASPP (96-105), respectively.

Figure 23A:
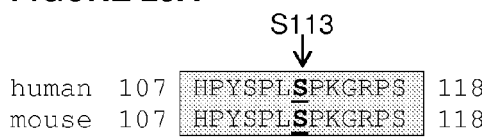
FIG. 23A provides the sequence of the iASPP peptide (amino acids 107-118 of SEQ ID NO: 2) used to generate the anti-iASPP phosphoserine 113 antibody as described in Example 1.

Generation of and Assays Determining Activity of iASPP-Ser 113 Phospho-Specific Antibodies:

iASPP-Ser 113 phospho-specific antibodies were generated by immunizing rabbits with an iASPP-Ser-113 phospho-specific peptide ($NH_2$—HPYSPL[phospho-S]PK-GRPSC-$CONH_2$ (SEQ ID NO: 14, which corresponds to amino acids 107-118 of SEQ ID NO: 2 (FIG. 23A) with a C-terminal cysteine added to allow conjugation to KLH). The sequence selected for immunization is conserved between human and mouse iASPP. Generated antibodies were individually purified against both phospho-modified and non-modified peptide.

Figure 23B:
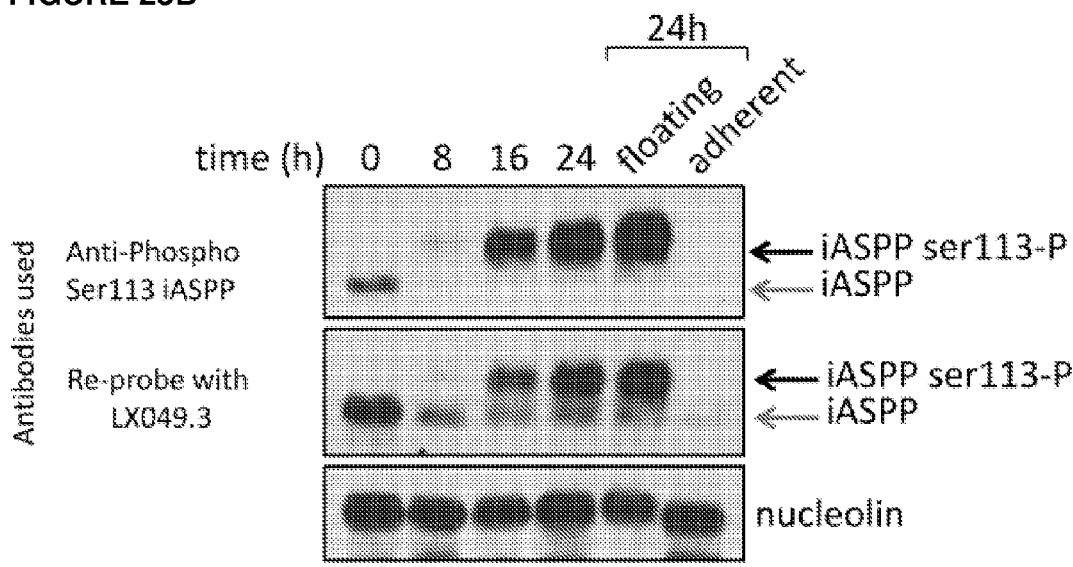
FIG. 23B is a gel showing that antibody binds phosphor-specific ser113 iASPP.

The phosphor-specific ser 113 anti-iASPP antibody (from rabbit 42310) was tested for binding activity by evaluating nocodazole (1 μM)-induced cell cycle arrested human U2OS cells (FIG. 23B). Human U2OS cells were treated with nocodazole (1 μM) at the time points indicated (FIG. 23B), all cells in the culture dish were harvested and lysate prepared by incubating for 30 minutes at room temperature in 8M urea, 1M thiourea, 0.5% CHAPS, 50 mM DTT and 24 mM spermine, followed by centrifugation at 20 000 g for 20 min. For the floating and adherent cells, the rounded (mitotic rich) cells were separated from the adherent cells after 24 hours treatment with nocodazole. Lysates were separated on a 6% SDS PAGE gel and proteins analysed by conventional western blotting. iASPP phosphor-ser113 was detected using the antibody from rabbit 42310 as described in FIG. 23A, and total iASPP was detected by re-probing the blot with antibody LX049.3. Nucleolin was used as a loading control. Binding of phosphor-specific ser 113 anti-iASPP antibody (42310) was demonstrated by evaluating the accumulation of phosphorylated iASPP over time in nocodazole arrested mitotic cells (FIG. 23B). Consistent with enhanced iASPP phosphorylation in nocodazole arrested mitotic cells, enhanced iASPP phosphorylation on ser 113 was also observed in the floating cells, which are mostly mitotic cells, and not in adherent cells (FIG. 23B). Total iASPP was detected by re-probing the blot with antibody LX049.3.

Figure 23C:
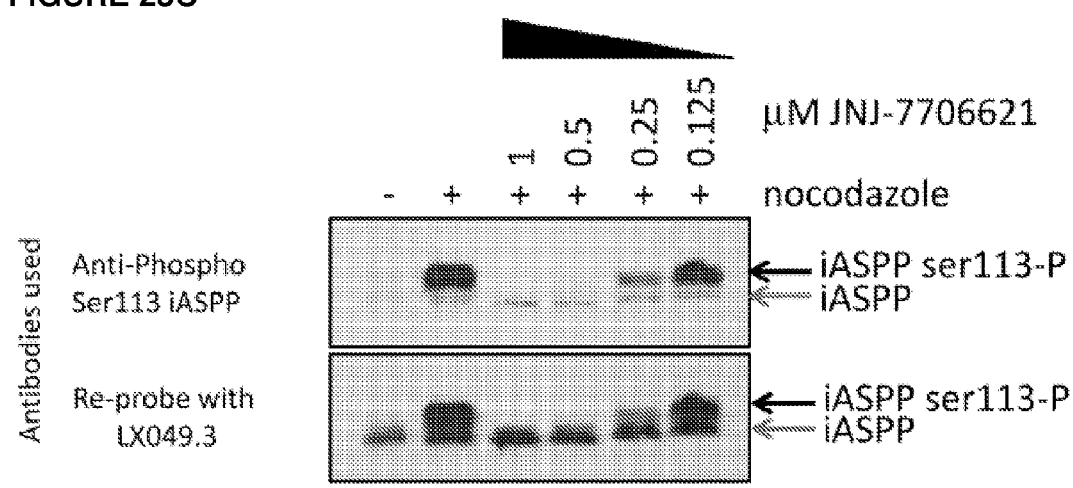
FIG. 23C is a graph showing the specific binding the anti-iASPP ser113 phosphospecific antibody to phosphorylated iASPP.

Additionally, the specific binding of iASPP antibody (42310) to phosphorylated ser 113 were evaluated by determining the failure of iASPP antibody (42310) to bind when the protein is not phosphorylated at ser 113. Since CDK kinase phosphorylates iASPP at ser 113, CDK inhibitor JNJ-7706621 was used to treat human U2OS cells. Binding was compared between untreated or JNJ-7706621 treated cells that were incubated for 16 hours with nocodazole (1 μM). Western blotting was carried out as described in FIG. 23B using an 8% SDS PAGE gel. When compared to untreated cells, binding of phosphor-ser 113 specific anti-iASPP antibody was not observed in the presence 0.5 μM JNJ-7706621 (FIG. 23C). Total iASPP was detected by re-probing the blot with antibody LX049.3. This experiment demonstrated the requirement for phosphorylation on serine 113 on iASPP in order for the antibody to bind. The western blot showed a decreased in binding of phosphor-specific ser 113 anti-iASPP antibody (42310) in the presence of CDK inhibitor JNJ-7706621 (FIG. 23C).

Generation of iASPP-Ser 84 Phospho-Specific Antibodies:

iASPP-Ser 84 phospho-specific antibodies will be generated by immunizing rabbits with an iASPP-Ser 84 phospho-specific peptide ($NH_2$—PEPFGSRG[phospho-S]PR-KAATC-$CONH_2$, (SEQ ID NO 15, which corresponds to amino acids 76-90 of SEQ ID NO: 2 with a C-terminal cysteine added to allow conjugation to KLH). Generated antibodies will be purified against both phospho-modified and non-modified peptide.

p53 and iASPP Knock Down.

P53 siRNA (MU-003329-03-0002, Dharmacon), or iASPP siRNA (MU-003815-01-0002) was wet reverse transfected into cells using DharmaFECT 1 Transfection Reagent kit (T-2001-02) during cell seeding. Protein levels were determined by WB.

Cell Cycle Analysis by Flow Cytometry.

Cells were harvested, washed and fixed in ice-cold 70% EtOH. Cells were washed and resuspended in PBS containing 0.05 mg/ml RNase A and 0.05 mg/ml propidium iodide (P4864, Sigma). After 30 min RT incubation cells were analyzed by flow cytometry.

Colony Assay.

After drugs treatment, cells were digested, counted, and seed in 6-well plates (100, 1 000, 10 000 cells/well). Cells were then grown for 10-14 days and stained by Giemsa (GS-500, Sigma).

Example 2—P53 Selectively Binds Slow-Migrating Nuclear iASPP

Figure 1B:
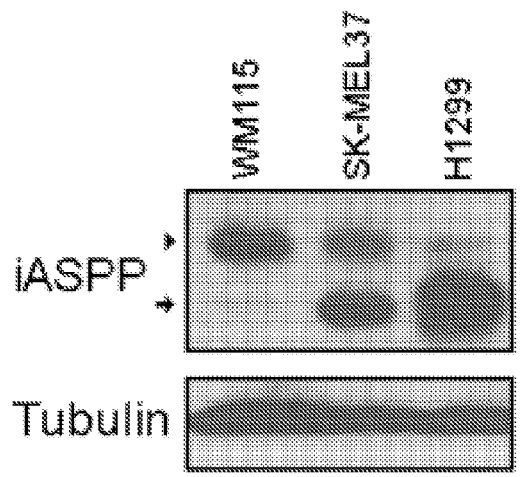
Figure 2A:
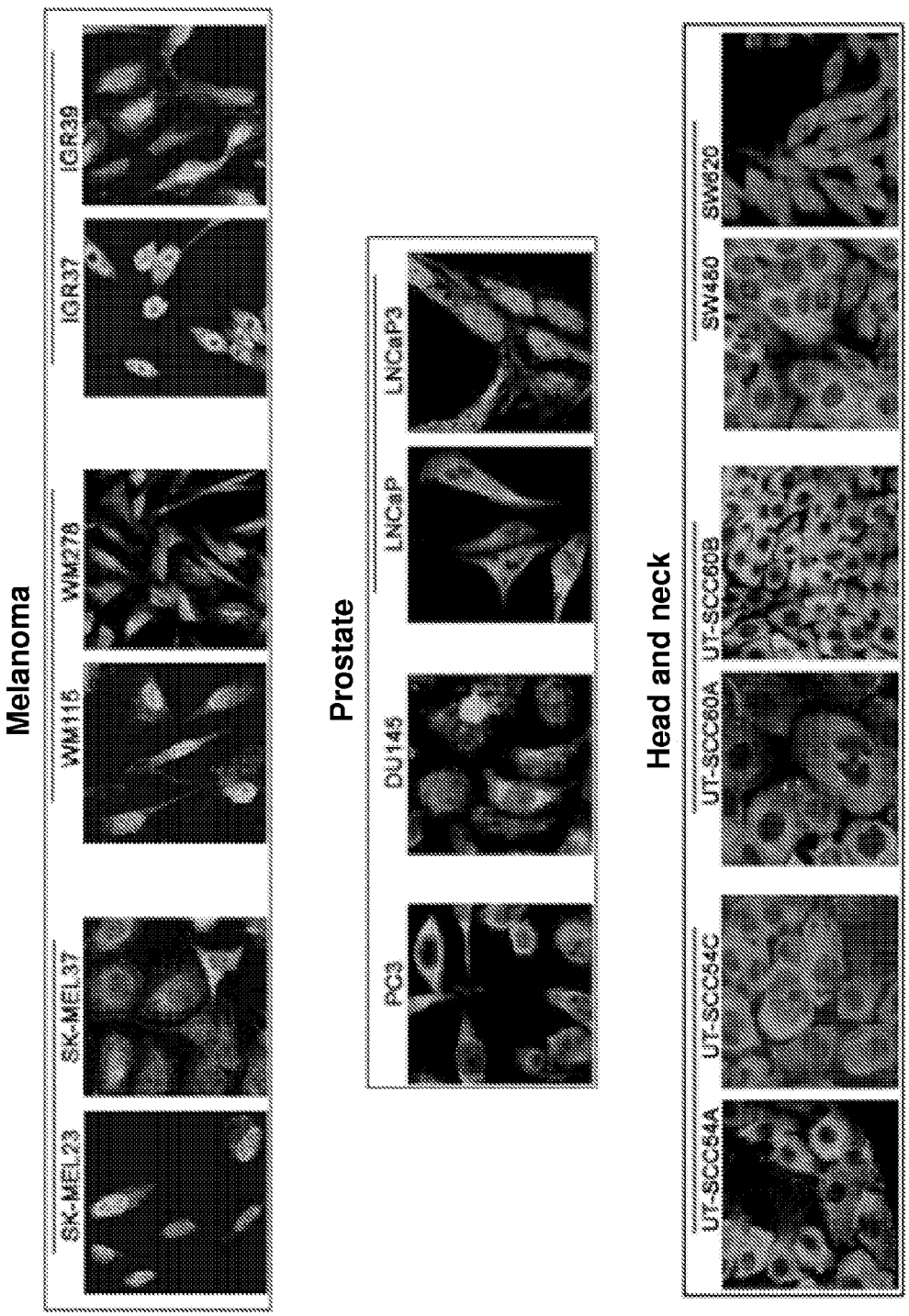
FIG. 2. iASPP cellular localization and expression pattern in various cell lines were determined by immunoassay with antibody LX49.3. Bar=20 μm. The tumor cell lines examined are indicated. Table 1 within
Figure 2A:
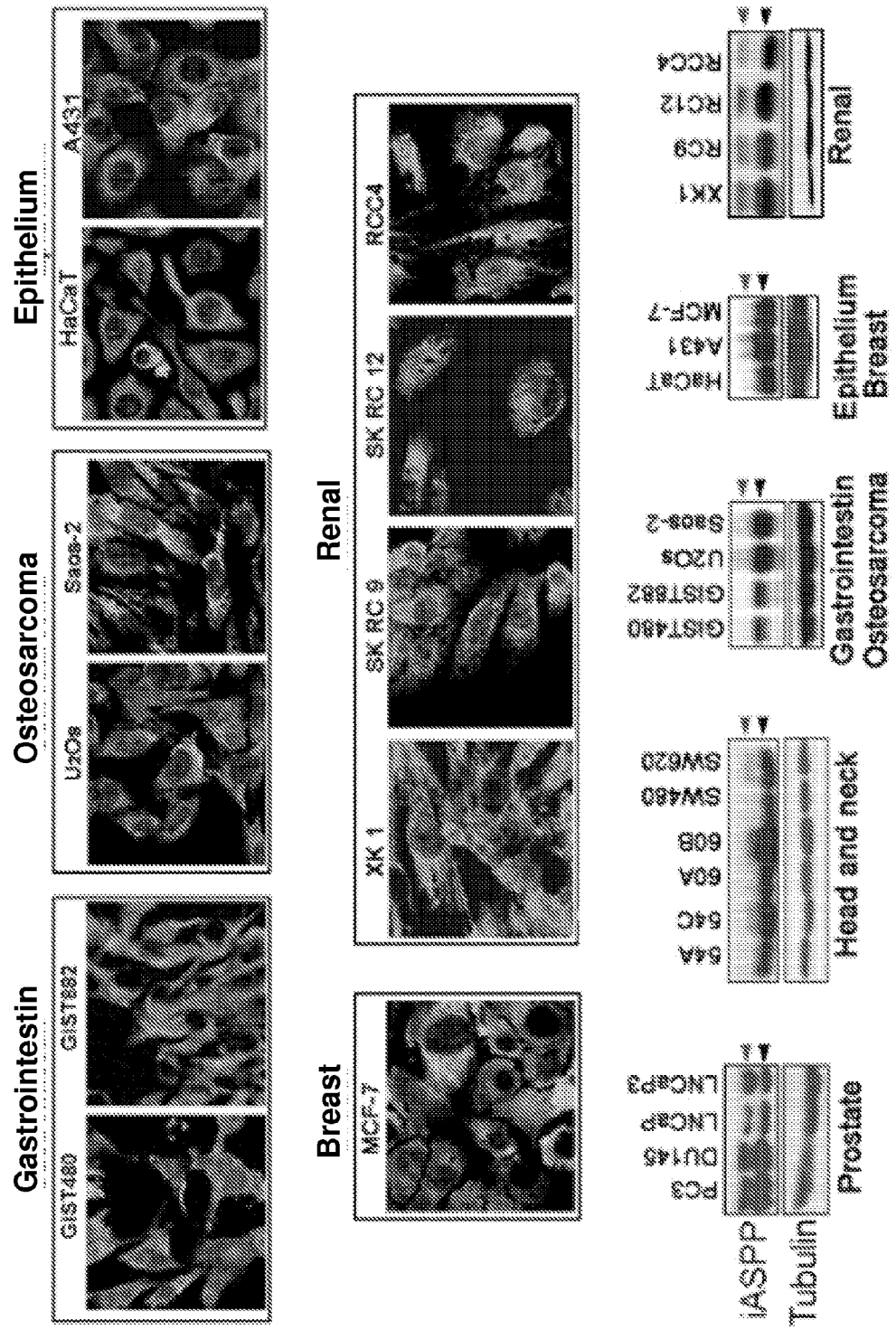

An inverse correlation between nuclear iASPP and epithelium differentiation in vivo illustrates the importance of iASPP localization in regulating its function (Notari et al., 2011). To understand the regulation of iASPP functions in vivo, it is critical to identify experimental systems in which iASPP localization is regulated. To achieve this, a panel of human tumor cell lines was examined for their iASPP expression patterns. In osteosarcoma, epithelium, breast, and renal cancer cell lines, iASPP is predominantly expressed as cytoplasmic protein (FIG. 2). Interestingly, however, a large number of melanoma cell lines express nuclear iASPP (FIGS. 1A and 1B). While SK-MEL37, WM278, and IGR39 show more cytoplasmic staining, SK-MEL23, WM115, and IGR37 (metastatic cell line derived from the same patient as that derived for IGR39) show predominantly nuclear staining. iASPP nuclear staining pattern is also found in LNCaP3, a cell lines derived from LNCaP after 3 rounds of ex-vivo selection of metastasis (Pettaway et al., 1996). To identify the underlying reason for the observed difference in iASPP cellular localization, iASPP proteins were analyzed by immunoblotting. Interestingly iASPP migrated as two bands in many melanoma cell lines tested and a slow-migrating iASPP isoform was tightly associated with the appearance of nuclear iASPP (FIG. 1B). While SK-MEL37, WM278, and IGR39 express more fast migrating iASPP isoform (black arrows), SK-MEL23, WM115, and IGR39 express predominantly slow-migrating iASPP (red arrowheads), so does LNCaP3. This is in contrast to the single iASPP band (fast migrating band) detected in all other cell panels that predominantly express cytoplasmic iASPP (FIG. 2, Table 1 of FIG. 2B and other data not shown).

Figure 1C:

Knowing that iASPP is able to bind and inhibit the apoptotic function of p53 and that p53 is predominantly a nuclear protein, the binding preference of p53 to different iASPP isoforms was evaluated. p53 was immunoprecipitated in a panel of melanoma cells that expressed various amount of nuclear iASPP with different migration ability. The results show that p53 was able to selectively co-immunoprecipitate the slow-migrating iASPP isoform in these melanoma cells (FIG. 1C). Under the same conditions p53 failed to co-immunoprecipitate the fast migrating iASPP. The failure of p53 to co-immunoprecipitate fast migrating iASPP is not linked to the level of iASPP isoform nor to the amount of precipitated p53 (FIG. 1C). These data suggest that p53 preferentially binds slow-migrating iASPP that is localized in the nucleus.

Example 3—Mitotic Arrests Induces Slow-Migrating Nuclear iASPP

Figure 3A:
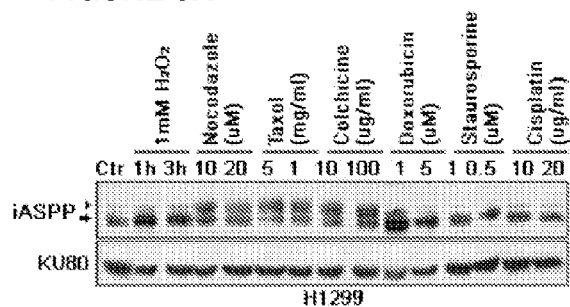
FIG. 3. Mitotic arrests induces slow-migrating nuclear iASPP. A. Mitosis-arresting (i.e., apoptosis-inducing) chemotherapeutic drugs induce slow-migrating iASPP. H1299 cells were treated overnight with the indicated concentrations of mitosis-arrest drugs nocodazole, colchicine and taxol, DNA damaging drugs, or oxidative stress inducers (1-3 h). Total lysate was prepared in UREA buffer, and iASPP expression patterns were determined using antibody LX49.3. B. Slow-migrating iASPP exclusively exists in mitotic cells after drug induction. Mitotic-arrest drugs were applied to H1299 cells to induce iASPP mobility shift. Floating and adherent cells were collected, and iASPP expression pattern was determined by western blotting (WB). C. Slow-migrating iASPP exists in natural mitotic cells and localized in nucleus (as determining by staining with the nuclear specific marker Topro). Left panel, cells in mitosis (floating) and interphase (adherent) were collected by mitotic shake-off, and iASPP expression pattern was determined by WB. Right panel, H1299 cells after Taxol treatment, or mitotic shake-off were immunofluorescence stained using antibody LX49.3. In mitotic shake-off experiment, mitotic shake-off cells were cytospun to slides; the remaining adherent cells after shaking were scraped off and used as interphase control. D. Mitotic-arrest drugs induce slow-migrating iASPP in melanomas. Melanoma cells were treated with nocodazole overnight and iASPP expression patterns from total cell lysate was determined by WB.
Figure 3B:
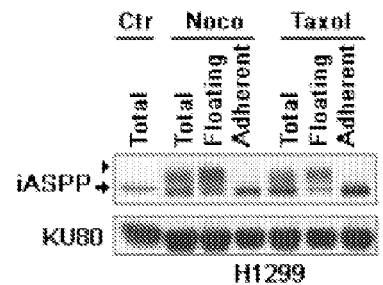

To better understand the signals that induce slow-migrating nuclear iASPP, a p53-null cell line H1299 was first used to study iASPP expression in response to various chemotherapeutic agents Like the majority of tumor cell lines studied, H1299 predominantly expresses cytoplasmic iASPP that migrates as a single band (FIG. 3A). Interestingly, the slow-migrating iASPP was induced only on treatment with mitotic arresting reagents such as Nocodazole, Taxol and Colchicine. In contrast, treatment with other chemotherapeutic agents that do not induce mitosis, such as Doxorubicin, Staurosporine, Cisplatin and hydrogen peroxide, did not result in increased slow-migrating iASPP isoform expression. As mitotic cells often detach from the tissue culture dish, floating cells were separated from adherent cells after the treatment of Nocodozole, Taxol and Colchicine. FIG. 3B shows the enrichment of slow-migrating iASPP in the floating mitotic cell population whereas iASPP is expressed as a single band in the adherent cells even after drug treatment.

Figure 3C:
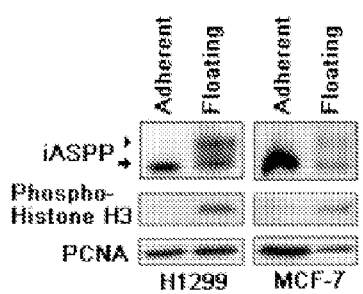
Figure 3C:
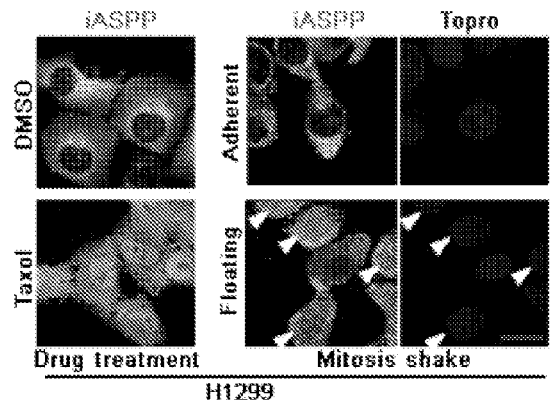

To provide further evidence that slow-migrating iASPP was induced by mitosis and is not limited to H1299 cells, mitotic H1299 and MCF7 cells were generated by mitotic shake, and enrichment of G2/M phase was confirmed by FACS analysis. Again, slower migrating iASPP was only detected in the collected mitotic cells, whereas in adherent cells iASPP is predominantly expressed as a single band (FIG. 3C). Importantly when the cellular localization of iASPP was examined in these two cell populations, it was observed that mitotic cells predominantly express nuclear iASPP whereas adherent cells predominantly express cytoplasmic iASPP (FIG. 3C).

Figure 3D:
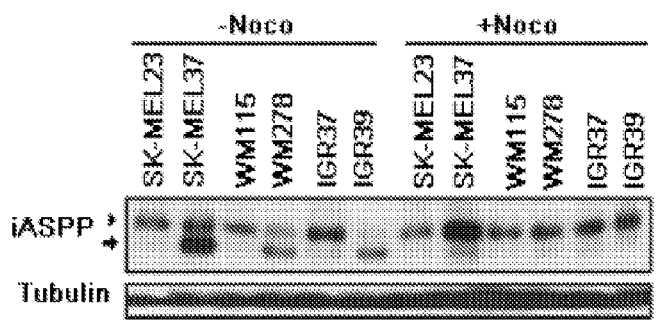
Figure 4A:
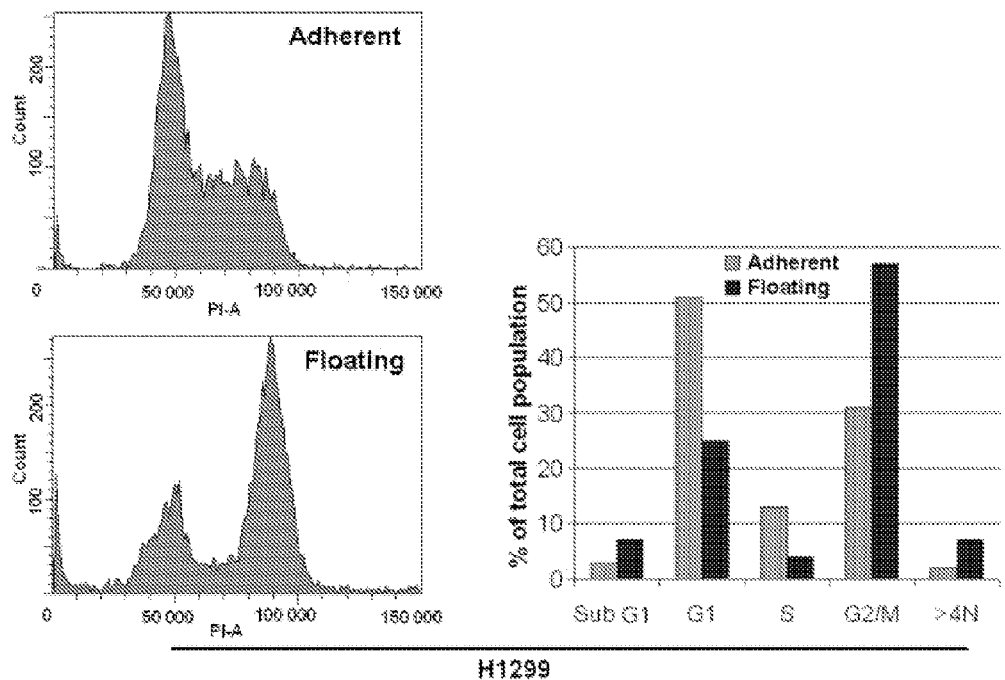
FIG. 4. A. Floating and adherent H1299 cells separately collected by mitotic shake-off (FIG. 3C) were stained with propidium iodide (PI), followed by FACS analysis. Left panel shows the representative cell cycle profile of floating and adherent H1299 cells, right panel show the calculated cell population in various cell cycle phase as indicated. B. H1299 cells were subjected to treatment of 10 μM nocodazole for 24 hours (Nocodazole), on ice for 30 minutes (Cold shock), or 4 mM EDTA for 1 hour (EDTA). Left panel: iASPP expression pattern was analysed by immunoblotting. Right panel: phase contrast images were taken before collection of the cells for WB analysis. Bar=20 μm.
Figure 4B:
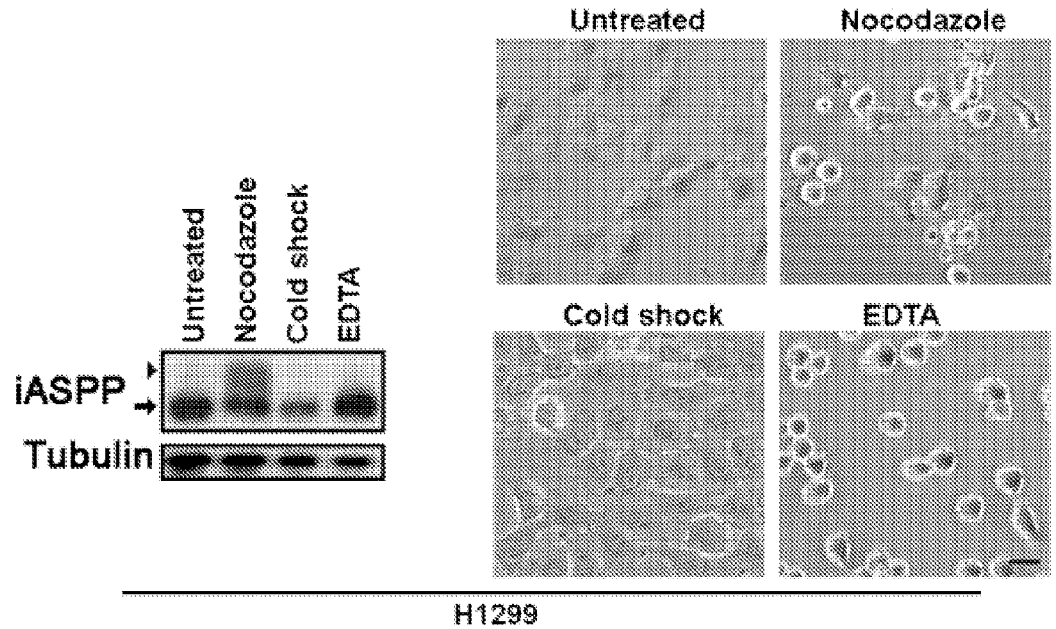

Finally, to confirm that the slow-migrating iASPP observed in melanoma cell lines was induced by the same signals, a panel of melanoma cell lines that expressed both slow and fast migrating iASPP isoforms were treated with Nocodazole to induce mitosis. Again, Nocodazole induced the conversion of faster migrating iASPP into the slower migrating iASPP isoform (FIG. 3D), suggesting that the slow-migrating nuclear iASPP is the same as that induced by mitosis. To provide further evidence that slow-migrating iASPP is specifically induced by mitotic arrest H1299 cells were generated by mitotic shake, and enrichment of G2/M phase was confirmed by FACS analysis (FIG. 4A). To eliminate the possibility that slow migrating iASPP is induced by cell detachment, H1299 cells were treated with stimuli such as EDTA or cold shock that induce cell detachment but not mitosis. Consistent with our findings above, both EDTA and cold shock failed to affect iASPP mobility, even though under the same conditions nocodazole induced slow migrating iASPP (FIG. 4B).

Example 4—Phosphorylation of iASPP at Ser84/Ser113 by Cyclin B1/Cdk1 Contributes to iASPP Slow Migration To identify the regions of iASPP that are responsible for mitosis induced slow migration, two V5 tagged iASPP truncation mutants; iASPP (1-478)-V5 and iASPP (482-828)-V5 were transfected into H1299 cells. The transfected cells were treated with Nocodazole or Taxol to induce mitosis. The mobility shifts of the transfected iASPP mutants were detected using anti-V5 antibody. The results shown in FIG. 3A illustrate that slow-migrating iASPP(1-478)-V5 was specifically induced in Nocodazole or Taxol treated cells. However, under the same conditions, iASPP (482-828)-V5 appeared predominantly as a single band, indicating that modifications on the N-terminal half of iASPP are responsible for the mitosis-induced slow migration of iASPP.

Figure 5A:
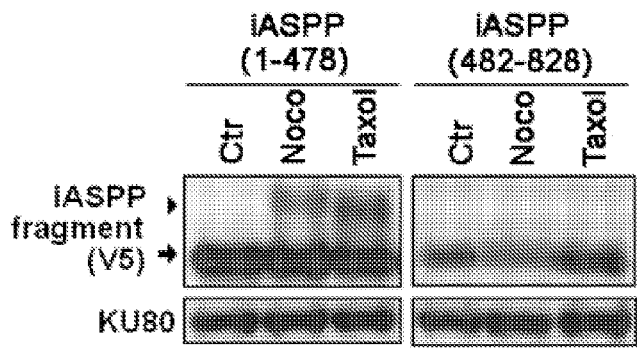
FIG. 5. CyclinB/cdk1 phosphorylation of iASPP at Ser84/Ser113 that contributes to iASPP slow migration. A. modification of iASPP is localized on N-terminus (1-478 aa). H1299 cells stably expressing V5 tagged iASPP fragments 1-478 and 482-828 were treated with nocodazole. Expression pattern of the iASPP fragments was determined using anti-V5 antibody. B. N-terminal iASPP (1-240) is a substrate of cyclinB/cdk1 in vitro. Beads pre-bound with 5 μg purified iASPP (1-240) (1-240, GST tag), or iASPP (249-482) (249-482, GST tag) were incubated with 0.2 μg/ml cyclin B1/ckd1 complex in NP40 buffer (containing 1 mg/ml BSA) for 2 hours. After 4 washes, bound cyclin B1/ckd1 complex was determined by WB. In lower panel, iASPP (1-240) and iASPP (249-482) was mixed with cyclin B1/cdk1 complex and [γ-32P]-ATP under standard kinase assay conditions, bound [γ-32P] was then determined in SDS-PAGE. For input experiments, the duplicated protein samples were stained by coomassie blue directly. C. iASPP-S84AS113A cannot be phosphorylated by cyclinB1/cdk1 in vitro. 5 µg iASPP (1-240) point mutants or double mutants on S84, S113, and S120 were subjected to cyclin B1/cdk1 in vitro assay. The average [γ-32P] signal was quantified from 3 separate experiments. D. Stably expressed iASPP-S84AS113A in IGR37 shows reduced mobility shift. IGR37 and IGR39 cells stably expressing iASPP mutants (tagged V5) were dissolved in UREA buffer and iASPP expression pattern was determined by WB.
Figure 5B:
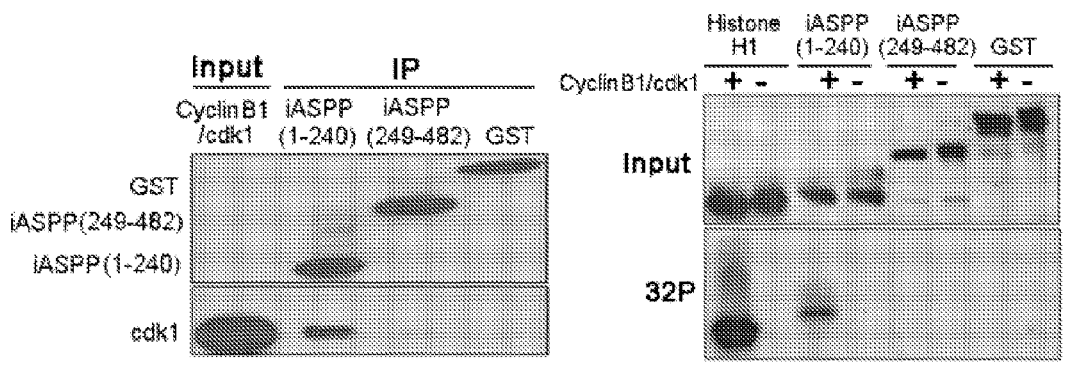
Figure 5C:
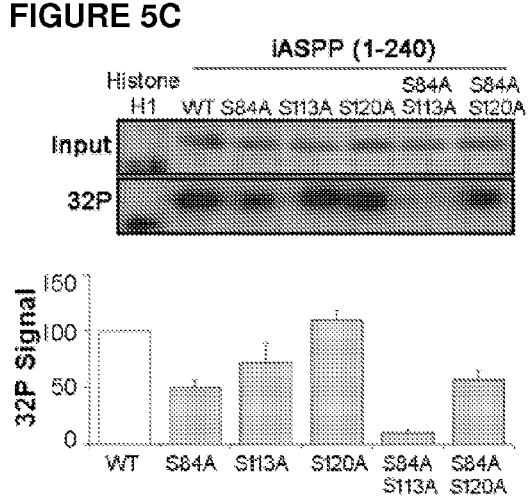

Phosphorylation is one of the best known modifications that can induce protein mobility shifts, and cyclin B1/cdk1 is one of the most active kinases in mitosis. We therefore tested whether iASPP is a substrate of cyclinB1/cdk1 and whether this phosphorylation may affect iASPP migration. Recombinant N-terminal iASPP fragments; iASPP (1-240) and iASPP (249-482) were tested in an in vitro kinase assay using purified cyclin B1/cdk1. iASPP (1-240) but not iASPP (249-482) bound and was phosphorylated by cyclinB1/cdk1 in vitro (FIG. 5B). The amino acid sequence that covers the N-terminal of amino acids 1-240 of iASPP was analyzed by Motifscan and identified S84, S113, and S120 of iASPP as potential cyclinB1/cdk1 phosphorylation sites. Thus Ser84, Ser113 and Ser120 were singly or doubly mutated to Alanine. The resulting iASPP (1-240) mutants (S84A, S113A; S120A; S84A/S113A; S113A/120A) were used in the cyclinB1/cdk1 kinase assay in vitro. Results shows that cyclinB1/cdk1 failed to phosphorylate iASPP (1-240) S84A/S113A whereas all other phosphorylation mutants of iASPP can be phosphorylated by cyclinB1/cdk1 in vitro.

Figure 5D:
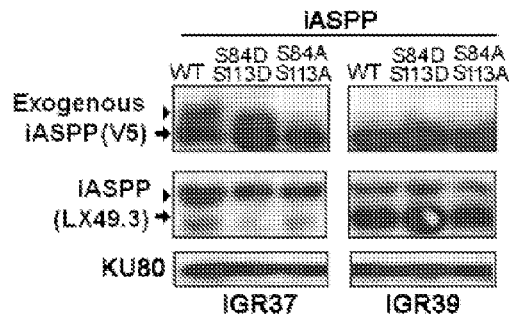

The two iASPP phosphorylation mutants; iASPP(S84A/113A)-V5 and iASPP(S84D/113D)-V5 were also transfected into melanoma cell lines IGR37 and IGR39. As expected, slow-migrating iASPP-V5 (wild type) was detected in IGR37 (without treatment of Nocodazole), but not in IGR39 cells. Interestingly, iASPP(S84D/113D) produced some slow-migrating iASPP in IGR37 cells, but not in IGR39 cells. In both iGR37 and IGR39 cells, iASPP (S84A/113A) remained as a single band (FIG. 5D).

Figure 6:
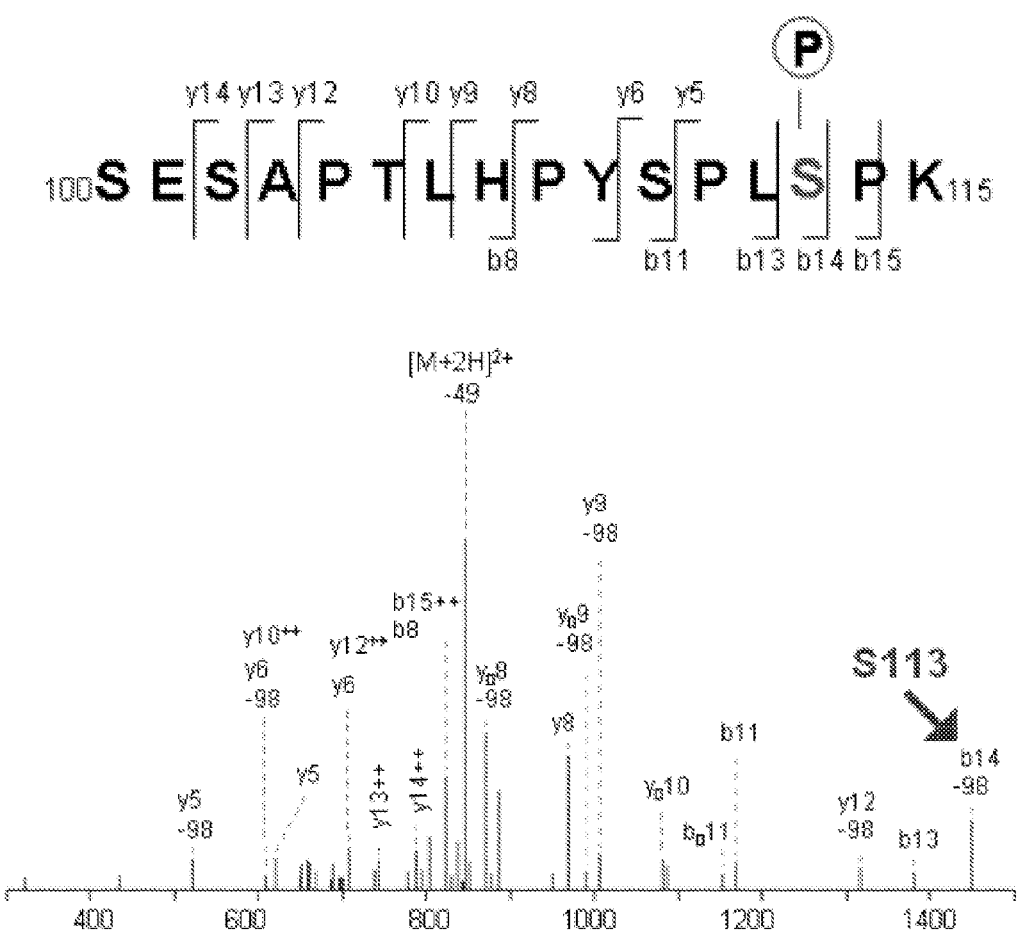
FIG. 6. Phosphorylation of iASPP on S113 during mitosis by mass spectrometry. H1299 cells were treated with or without 10 µM nocodazole for 24 h. iASPP was immunoprecipitated (from 40 mg protein lysate) using cross-linked antibody LX49.3. Proteins were separated by SDS-PAGE and the gel was stained with coomassie and silvernitrate. Protein bands that are corresponding to the molecular weights of iASPP were excised, digested with trypsin and analysed by tandem mass spectrometry. MS/MS spectrum of the iASPP derived tryptic peptide 100-115 of SEQ ID NO: 2 is shown, in which b and y fragment ions are indicated. Phosphorylation is mapped to Ser113; -98 Da: loss of phosphoric acid; ++ doubly charged ion; o:—NH2. Ser84 in derived tryptic peptide is also determined to be phosphorylated in nocodazole treated sample; however, its status in untreated sample remains unknown as it was not covered in generated tryptic peptide in current assay.

Finally, mass spectrometry analysis confirmed that endogenous iASPP from H1299 cells was phosphorylated at S113, but not during interphase (FIG. 6). Taken together, these findings demonstrate that iASPP is phosphorylated by cyclinB1/cdk1 at Ser84 and Ser113 and that phosphorylation retards iASPP migration.

Discussion:

CyclinB1/cdk is involved in iASPP modification during mitosis and in melanomas. According to whole genome based arrays examining the genes aberrantly expressing in melanoma cell lines in vitro, cyclin B1 was of the most upregulated genes (fold change: +18.17) (Avery-Kiejda et al., 2011). In vivo, cyclin B1 had dramatically increased protein expression in metastases tissue sections comparing with primary melanomas (Georgieva et al., 2001). In esophageal squamous cell carcinoma, cyclin B1 has been implicated in metastasis by promoting an epithelial-mesenchymal transition (Song et al., 2008). It seems these overexpressed cyclin B1 play some other roles (such as dominate phosphorylation pattern over unphosphorylation pattern for its substrates) besides functioning as mitosis regulator as the melanoma cells universally show normal cell cycle profile. Supporting the proposed role of cyclin B1/cdk1 in vitro, levels of modified iASPP showed significant positive correlation with cyclinB1 level (activator of cdk1 kinase), but not cdk1 level, in 18 melanomas, 7 prostate cancer cells, and in mitotic H1299 cells (FIGS. 10 and 11). Supporting cdk1 's role in iASPP phosphorylation, phosphorylation kinase inhibitor screening result shows that cdk and clk (cdk like kinase) inhibitors can indeed prevent iASPP modification, while other kinase inhibitors (Aurora, Plk1, or Pim 1) cannot (FIG. 12). Herein, a cdk1 inhibitor, k00616a was highlighted as its high efficiency in blocking iASPP modification. It has been reported to be able to inhibit melanomas in vivo in a human tumour xenograft model in mice (Emanuel et al., 2005).

Figure 10A:
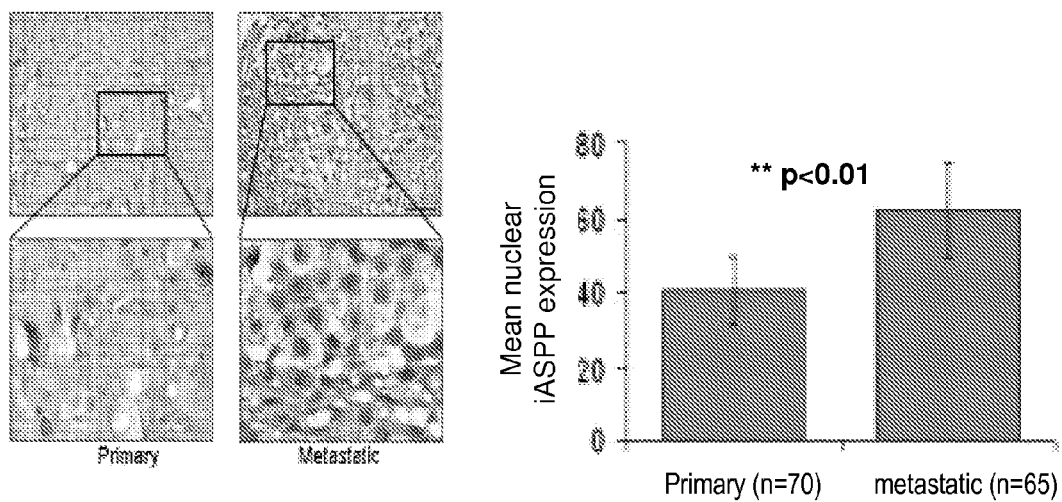
FIG. 10A. Nuclear iASPP shows association with metastasis in melanoma tissue. Left panel: representative iASPP staining pattern in primary tumours (Mdn40.0) and lymph node metastases (Mdn70.0) in melanoma tissue microarray cores. Bar=50 µm. Tumor tissues were stained with LX49.3. Right panel: the overall nuclear iASPP level is significantly higher in lymph node metastases compared to primary tumours in 135 melanoma tissue microarray cores (U=1740.000, r=−0.21, p<0.01). iASPP expression level=Intensity of staining (0-none, 1-weak, 2-moderate, 3-strong)×Proportion of cells exhibiting staining (0-100% in 5-10% increments). Results were analysed using the Mann-Whitney test (U). The effect size is denoted by r=z/√n(>0.3=medium effect, >0.5=large effect). ** p<0.01.
Figure 10B:
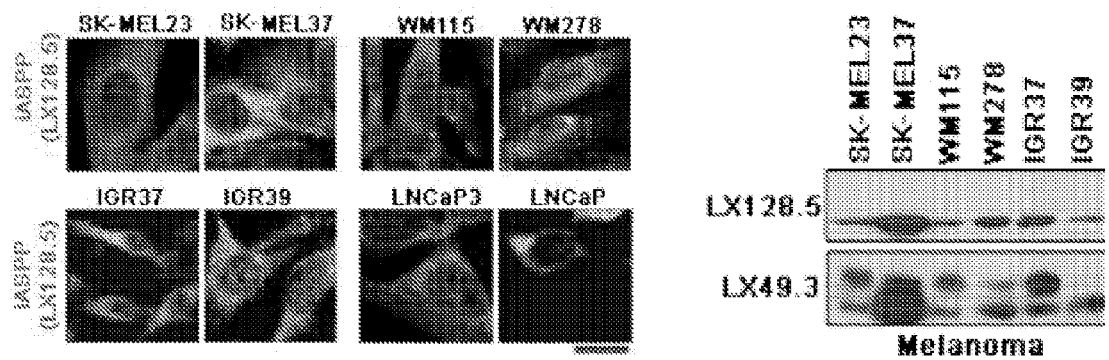
FIG. 10B. Slow-migrating nuclear iASPP lost epitope of LX128.5. The iASPP immunostaining pattern in a panel of melanoma cells were determined by LX128.5 antibody (immunostaining pattern for LX49.3 was shown in FIG. 10A). Bar=10 µm. The iASPP expressing pattern in melanoma cells (total cell lysate in urea buffer) was determined by LX128.5 and LX49.3 antibody, respectively.
Figure 10C:
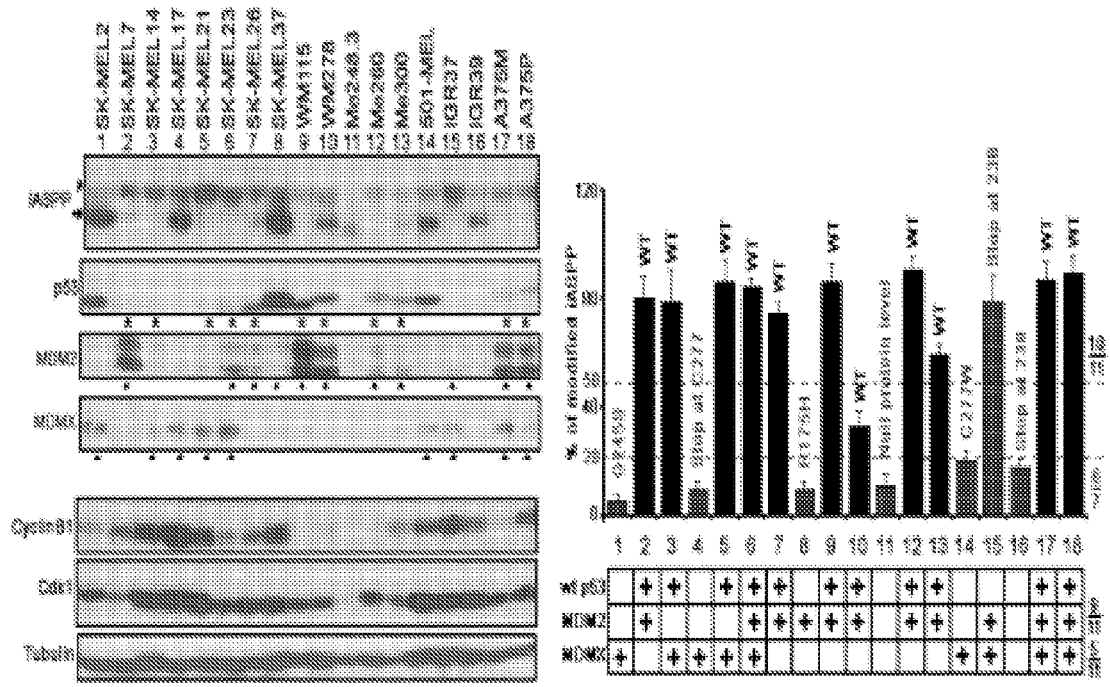
FIG. 10C. p53 wild type melanomas show high ratio of slow-migrating iASPP, and slow-migrating iASPP level shows positive correlation with cyclin B1 level. Left panel: cell lysate from 18 melanoma cell lines was prepared in urea buffer and indicated proteins were determined by WB. Samples with wild type p53 and overexpressed MDM2/MDMX are labelled with stars and triangles, respectively. Right panel: bar graph shows the iASPP modified ratio and p53 status (indicated on the bar). Lower table: wild type p53, overexpression of MDM2, and overexpression of MDMX are shown in melanomas.

Besides cyclinB1 and cdk1, the expression pattern of other 24 key proteins involved in tumorgenesis of melanomas were screened. Among these 24 proteins, the interested ASPP2, MDM2 family members, melanoma-associated antigens, familial melanomas candidate p16ink4a, Braf-Brn2-MITF-TBX2 pathway components, mitosis related cdks and cyclins, ckd5 and regulators, and prolyl hydroxylases did not show significant correlation with iASPP modification pattern, except for p53 and MAGE-C2. While MAGE-C2 showed relatively weak correlation with iASPP modification pattern, p53 showed a strong correlation with iASPP modification pattern in both 18 melanomas and 7 prostate cancer cells. p53 cDNA were then amplified from melanomas and their statuses were sequenced. As a result (FIG. 10C and FIG. 11C), cells with a low ratio of modified iASPP universally host mutated p53 (6/7 for melanomas, 5/5 for prostate. Me248.3 is the only exception; it hosts wild type p53 mRNA, but exhibits null p53 protein level for an unknown reason. Cells with high ratio of modified iASPP universally host wt p53 (10/11 for melanomas, 2/2 for prostate). IGR37, the only exception with mutated p53 but a high iASPP modification ratio, is derived from a same patient with primary IGR39. IGR37 is established to be a malignant melanoma cell line, described to be very metastatic and tumorigenic in nude model and confirmed in human. It shows high iASPP modify ratio comparing with primary IGR39 (~80% vs ~15%). It implied that iASPP might also be preferentially modified in metastatic cells. This implication was confirmed in prostate LNCaP3, the cell line derived from LNCaP after 3 times metastasis in mouse. Consistent with IGR37/39 couple, LNCaP3 show significantly increased iASPP modify ratio comparing with LNCaP (FIG. 10C, ~75% vs ~35%, FIG. 11C). The trend was also partially fit in head and neck cell couples, though it is not as dramatic as in melanomas or prostate (data not shown).

Example 5—S84/S113 Phosphorylation of iASPP Promotes iASPP Nuclear Localization by Preventing N- and C-Terminal Self-Interaction In our recently solved crystal structure of C-terminus of iASPP, we observed that a peptide (GSPRKARR) within iASPP (residues 615-622 of SEQ ID NO: 2) was able to efficiently bind C-terminal iASPP and mask the p53 binding space (Robinson et al., 2008). Interestingly, this peptide shares high sequence similarity with the N-terminal region of iASPP where S84 (GSPRKAAT, amino acids 83-90 of SEQ ID NO: 2) is located. This led us to the hypothesis that the N-terminal of iASPP interacts with its C-terminus, and phosphorylation of iASPP at Ser84 and Ser113 may interfere with this interaction. Indeed, purified iASPP(1-240) but not iASPP(249-482) can interact with purified iASPP C-terminal fragment, iASPP(626-828), which contains the ankryin repeats and SH3 domain. Under the same conditions, iASPP (1-240) did not interact with the C-terminus of ASPP2 (905-1128, containing ARDs and SH3 domain) (FIG. 7A). Using a number of iASPP variants singly and doubly mutated at Ser84, Ser113 and Ser120 sites it was observed that residues S84 and S113, but not S120, are involved in this N- and C-terminal interaction of iASPP as Ala mutation of Ser84 and Ser113 largely weaken the interaction (FIG. 7A, lower panel: compare lanes 2 versus 5 and 6). Phosphorylation mimic mutations Ser84D and Ser113D efficiently abrogated this interaction (FIG. 7A, lower panel: compare lanes 2 versus 9).

The involvement of S84/S113 phosphorylation in iASPP N- and C-term self-interaction in vivo was further tested by transfecting N-terminal iASPP(1-478) into Ras and E1A immortalized iASPP (−/−) mouse embryonic fibroblasts (MEFs) and the transfected cells were treated with nocodazole to induce post-translational modification and slow migration of the transfected iASPP(1-478). The transfected and treated cell lysates were incubated with the purified recombinant iASPP C-terminal fragment, iASPP(625-828). Consistent with the prediction that phosphorylation at Ser84/Ser113 disrupts the N- and C-terminal self-interaction of iASPP, the iASPP(625-828) selectively bound the non-modified, fast migrating N-terminal iASPP (FIG. 7B). Similarly, when purified recombinant iASPP(1-240) was incubated with nocodazole treated H1299 cell lysates, it specifically bound to nocodazole-induced modified, slow-migrating endogenous iASPP (with exposed C-terminus, FIG. 7B).

To understand whether iASPP forms N- and C-terminal self-interacting monomers or anti-parallel homodimers, iASPP migration was compared between non-denaturing or denaturing gels using H1299 cell lysates derived from nocodozale treated or non-treated cells. In a denaturing SDS-page gel, iASPP migrated as a single 100 kd band in normal growing H1299, but migrates as double bands in nocodazole treated H1299 cells. In a non-denaturing gel, iASPP from normal growing H1299 cells migrated as a single band but with a molecular weight almost double the size detected in SDS denaturing gel (FIG. 7B). The iASPP expressed in Nocodazole treated H1299 cells migrated as two bands that differed dramatically in size, one was about 90 kd whereas the other migrated at about 180 kd, almost double the size of the fast migrating iASPP (FIG. 7B). This result suggests that in normal growing H1299 cells, iASPP exists as an anti-parallel homodimer. However, in mitosis and upon Ser84/Ser113 phosphorylation, the N- and C-termini self interaction is disrupted and results in the formation of an iASPP monomer.

Figure 8:
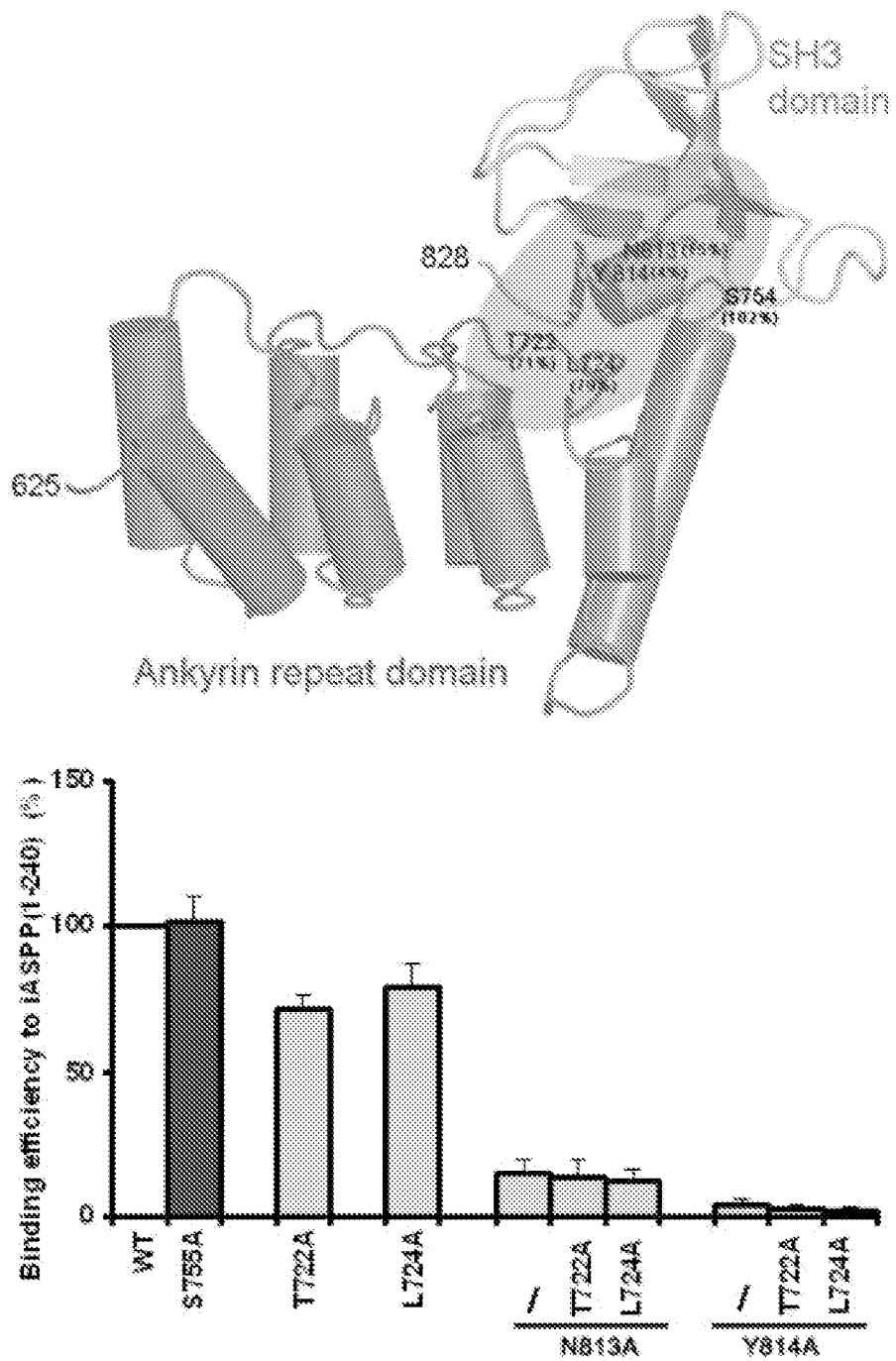
FIG. 8. N-terminal iASPP binds N813 and Y814 of C-terminal iASPP. The bar graph (according to FIG. 4C in manuscript) shows the calculated binding efficiency between iASPP (1-240)-GST and iASPP (625-828)-V5 mutants from two individual experiments. Binding efficiency=bound iASPP (625-828) signal/input iASPP (625-828) signal. The upper cartoon figure (modified from Robinson's publication) shows the residues (in red) involved in iASPP self-interaction according to the current assay; the percentages under residues represent the remaining bind signal after Alanine point mutation; the grey area represents the putative p53 binding space of iASPP, according to our recently determined iASPP (625-828) structure (Robinson et al., 2008).

Based on the crystal structure of iASPP and the sequence similarity between two iASPP peptides, (GSPRKAAT, amino acids 83-90 of SEQ ID NO: 2) and (GSPRKARR, amino acids 615-622 of SEQ ID NO: 2), it was suggested that T722, L724, N813, and Y814 might be contact residues located at the C-terminal end of iASPP. Single and double mutants were generated on these four residues and their ability to interact with N-terminal iASPP(1-240) was tested in vitro. We observed that iASPP(625-828)/T722A and iASPP(625-828)/L724A can bind N-terminal iASPP slightly less efficiently than wild type iASPP(625-828). However iASPP(625-828)/N813A or iASPP(625-828)/Y814A have a much reduced ability to bind iASPP(1-240). Additionally, iASPP(625-828)/T722A/N813A, iASPP(625-828)/T722A/Y814A, iASPP(625-828)/T724A/N813A or iASPP(625-828)/T724A/Y814A almost lost their ability to interact with iASPP(1-240). This identifies N813 and Y814 as two key residues that interact with N-terminal iASPP (FIG. 7C, and FIG. 8).

To test the hypothesis that N- and C-terminal self-interaction prevents iASPP nuclear entry, digitonin permeabilized H1299 cells (with permeable cellular membrane and intact nuclear membrane) were used to carry out an in vitro nuclear entry assay using FITC labeled iASPP C-terminal fragment; iASPP(625-828). FITC labeled ASPP2 C-terminus; ASPP2(905-1128) was used as a negative control. As reported previously (Slee et al., 2004), both C-terminal iASPP and ASPP2 can enter the nucleus with high efficiency. Interestingly, a pre-incubation with increasing amount of non-labeled N-terminal iASPP(1-240) effectively prevented the nuclear entry of FITC labeled iASPP(625-828). Under the same conditions, a pre-incubation of iASPP phosphor-mimic mutant, iASPP(1-240)S84D/S113D, failed to have any impact on the nuclear entry efficiency of FITC labeled iASPP(625-828). Furthermore, iASPP(1-240) only affected the nuclear entry of iASPP(625-828) since it had no impact on the nuclear entry of ASPP2(905-1128)(FIG. 7D). In agreement with this, iASPP(S84D/S113D), showed more nuclear localization comparing with wild type iASPP in iASPP(-/-) MEFs (FIG. 7E).

Example 6—Phosphor-Mimic iASPP, iASPP(S84D/S113D), is More Active than Wild Type iASPP in Binding and Inhibiting p53

Figure 9A:
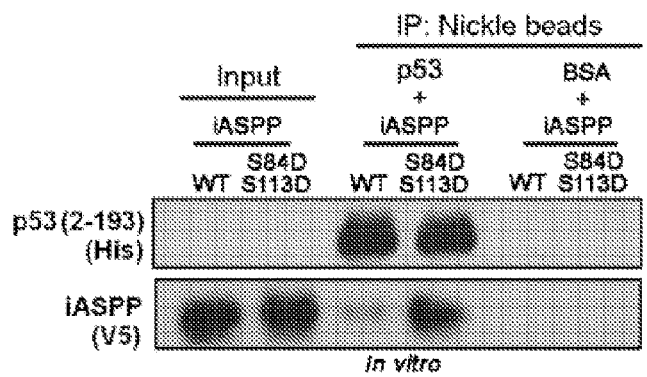
FIG. 9. Phospho-mimic iASPP, iASPP(S84D/S113D), is more potent than wild type iASPP in binding and inhibiting p53. A. iASPP S84D/S113D binds p53 better than WT iASPP in vitro. in vitro translated iASPP-V5 (WT) or its mutant iASPP(S84D/S113D) (S84D/S113D) (Input) were incubated with nickel beads that were pre-bound with either p53(2-193)-His (p53) or BSA (BSA) to carry out an immunoprecipitation assay (IP). The amount of iASPP that was co-immunoprecipitated with p53 was detected by an anti-V5 antibody (iASPP V5 panel) whereas the amount of p53 immunoprecipitated was detected by an anti-His antibody (p53(2-193)-His panel). B iASPP S84D/S113D binds p53 better than WT iASPP in transfected cells. iASPP-V5 (WT) or its mutant iASPP(S84D/S113D) (S84D/S113D) and p53 were co-transfected in H1299 cells (Input). Cell lysate was prepared in NP40 buffer; p53 antibody (Do-1) was applied to co-immunoprecipitate co-transfected iASPP and its mutant. The amount of p53 pulled down is shown in (p53 panel) whereas p53 bound iASPP was determined by anti-V5 antibody (iASPP V5 panel). IgG was used as a negative control. C iASPP S84D/S113D inhibits p53 reporter activity better than wild type iASPP. The bar graph shows the effect of iASPP (WT) or its mutant, iASPP(S84D/S113D) (DD) on the transcriptional activity of p53 on PIG3 in Saos-2 cells. Values are the mean±SD of three independent experiments. Lower panel: the expression levels of various transfected proteins as indicated. Tubulin is used as a loading control. D iASPP S84D/S113D confers iASPP(−/−) MEFs higher resistance to apoptosis than wild type iASPP. Ras and E1A transformed iASPP(−/−) MEFs (Refers as iASPP(−/−) MEFS) stably expressing vector (Vec), iASPP(WT), or iASPP S84D/S113D (84D/113D) were subjected to various treatment as indicated for 24 hours. Cells were dissolved in urea buffer. The expression levels of known apoptosis markers were detected in immunoblotting using D214 or D175 to detect cleaved PARP (c-PARP) or caspase 3 (c-caspase 3) respectively. E. iASPP S84D/S113D confers upon MEFs more resistance to Chemotherapeutic drug induced apoptosis. iASPP knockout MEFs stably expressing vector, iASPP, or iASPP (S84D/S113D) were subjected to apoptosis induced drugs for 24 hours. Cells were dissolved in urea buffer and apoptosis markers (cleaved PARP, caspase-3) were determined by WB.
Figure 9B:
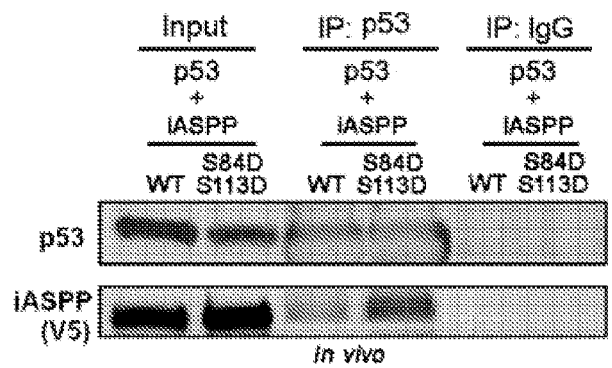
Figure 9C:
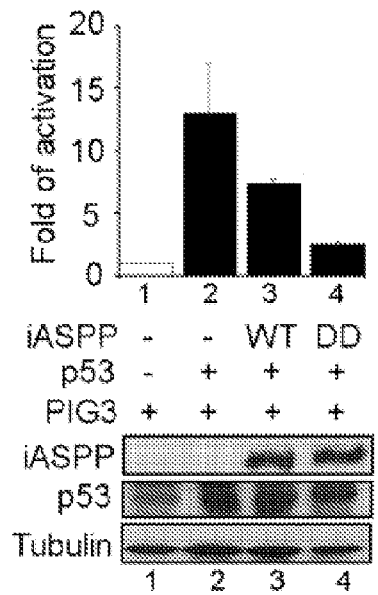

Knowing that modified iASPP unmasks its nuclear localization and p53 binding sites, it was hypothesized that phosphor mimic iASPP double mutant, iASPP(S84D/S113D), would bind p53 more effectively both in vitro and in vivo. This binding affinity between iASPP wild type and iASPP(S84D/S113D) was first compared using in vitro translated iASPP and recombinant p53. The results shown in FIG. 9A illustrate that iASPP(S84D/S113D) was able to bind p53 much better than iASPP wild type. When transfected into H1299 cells, the phosphor-mimic mutant, iASPP(S84D/S113D), was also able to bind co-transfected p53 much more effectively (FIG. 9B). In agreement with these findings, iASPP(S84D/S113D), was observed to be ~3-fold more effective in inhibiting p53 mediated transcription on promoters such as PIG3 (FIG. 9C).

Figure 9D:
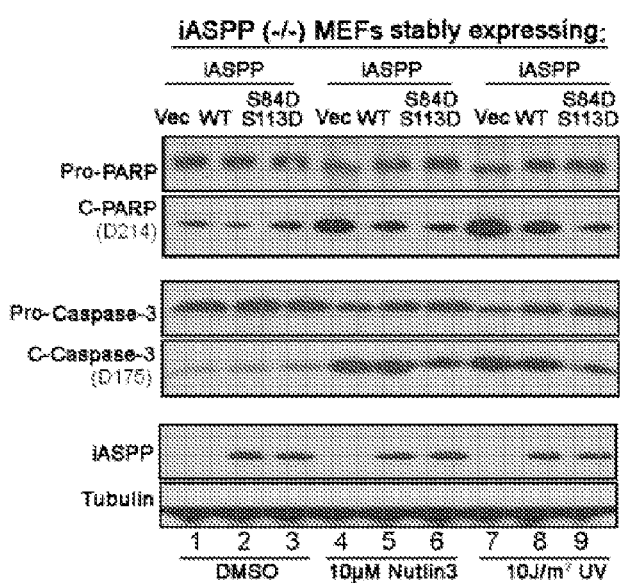
Figure 9E:
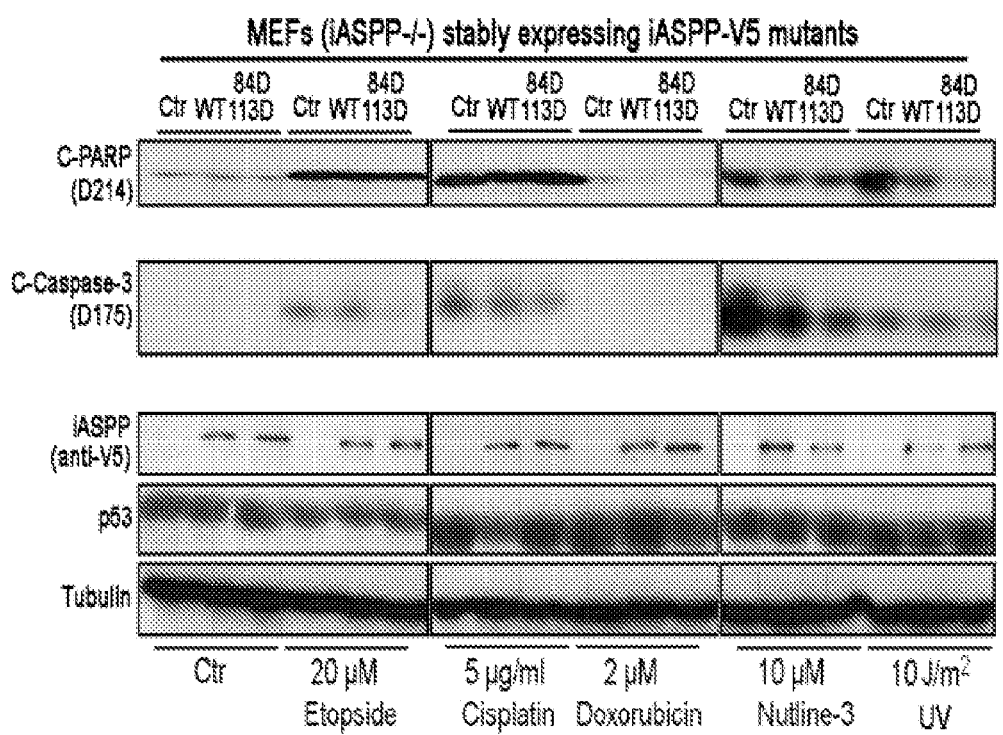

The anti-apoptotic function of iASPP and its mutant iASPP(S84D/S113D) was tested in Ras and E1A transformed iASPP(-/-)MEFs (referred to as iASPP(-/-)MEFs). Cells that stably expressed either vector, iASPP or iASPP (S84D/S113D) were treated with DMSO, Nutlin3 or 10 J/m2 of UV light. Apoptosis was measured by the presence of cleaved PARP (c-PARP) or active caspase 3 (c-Caspase 3). The expression levels of iASPP and its mutant are similar and comparable to that of endogenous iASPP (data not shown). The presence of iASPP or iASPP(S84D/S113D) had little impact on cell survival in DMSO treated cells. However, when the panel of cells were treated with Nutlin3 to induce endogenous p53, apoptosis was detected in vector transfected iASPP(-/-)MEFs, based on an increase in c-PARP and c-Caspase 3 and a decrease in pro-PARP and pro-caspase (FIG. 9D, compare lane 1 versus lane 4). The presence of iASPP caused a small decrease in c-PARP expression but had minimal impact on c-caspase 3 expression (compare lanes 4 and 5). The presence of iASPP(S84D/S113D), however, decreased the expression levels of both c-PARP and c-caspase 3 (FIG. 9D, compare lanes 4 and 6). A decrease in c-caspase 3 was also observed for Cisplatin or Etopside treatment (FIG. 9E). These results suggest that iASPP(S84D/S113D) is more potent than wild type iASPP in inhibiting p53 induced apoptosis in response to Nutlin3, Cisplatin, or Etopside treatment. Similarly, the presence of iASPP(S84D/S113D) also resulted in the highest reduction in the levels of c-PARP and c-caspase 3 in comparison to that detected in vector or iASPP expressing cells exposed to 10 J/m2 UV (FIG. 9D, compare lanes 7-9).

Example 7—Ser84/Ser113 Phosphorylated iASPP is Enriched in Wild Type p53 Expressing Tumor Cells with High Metastatic Potential Based on the findings presented above, it was hypothesized that nuclear iASPP is associated with cancer malignancy. This hypothesis was tested in a human melanoma tissue microarray (FIG. 10A). It was observed that iASPP is predominantly distributed in the nucleus in most melanoma metastases, while it is relatively equally distributed between the nucleus and the cytoplasm in primary melanomas. Further, the overall nuclear iASPP level is significantly higher in lymph node metastases (Mdn70.0) compared to primary tumours (Mdn40.0) (U=1740.000, r=-0.21, p<0.01).

Figure 11A:
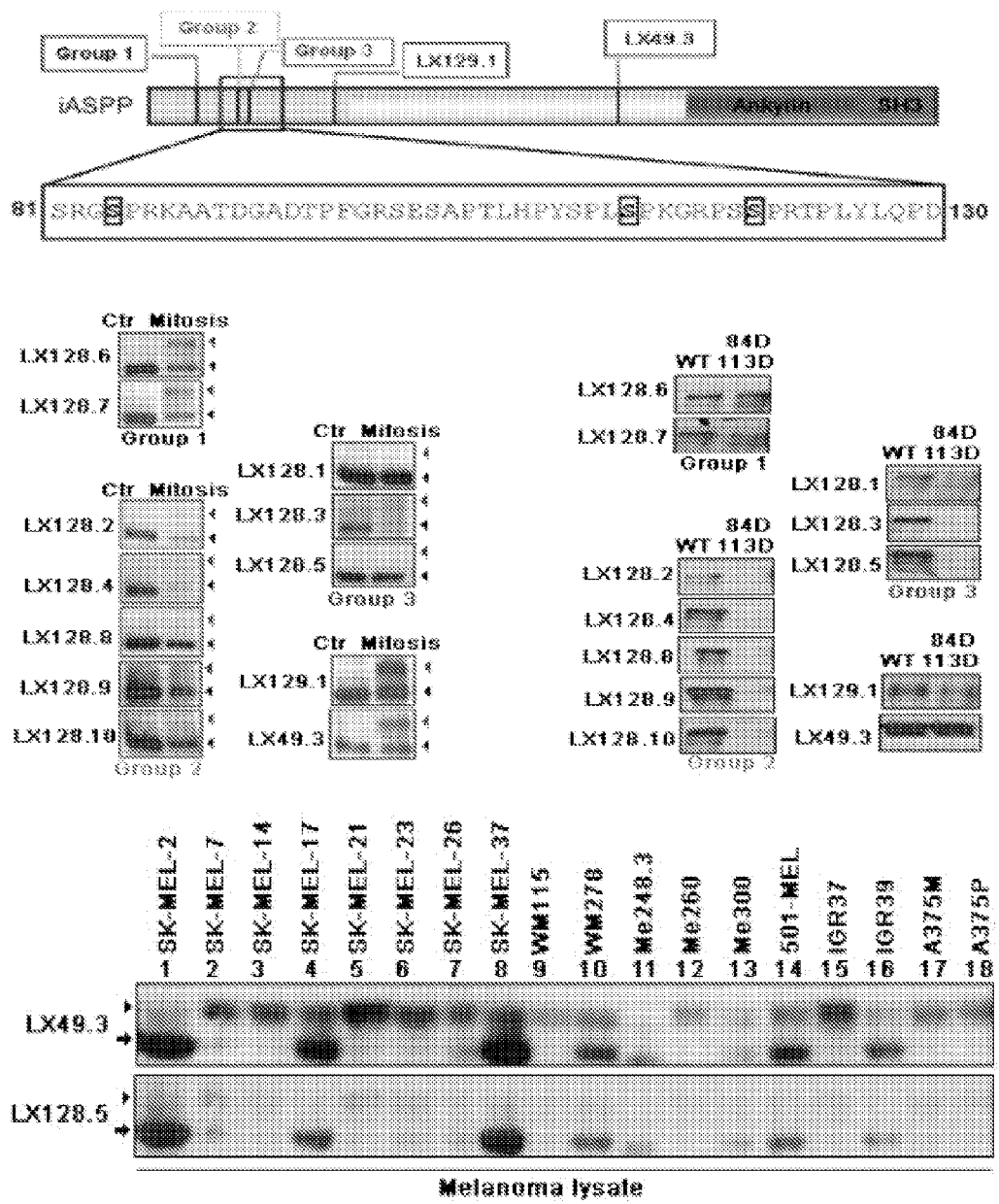
FIG. 11A. Panels of iASPP antibodies lose epitopes in slow-migrating iASPP and iASPP S84D/S113D. Upper cartoon figure: epitope locations of iASPP antibodies. H1299 lysate panel: H1299 cells were treated with nocodazole overnight, and cell lysate in urea buffer was probed using panels of iASPP antibodies as indicated by immunoblotting. iASPP IVT panel: in vitro translated wild type iASPP and iASPP S84D/S113D were probed using panels of iASPP antibodies by immunoblotting. Melanomas panel: melanoma lysate in urea buffer was probed with iASPP antibody LX49.3 by Western blot (WB). After stripping, the membrane was re-probed with LX128.5.

To confirm that the observed alterations in iASPP location and function are at least partly caused by modifications on the identified region of iASPP that contains Ser84 and Ser113, we generated a panel of mouse monoclonal anti-iASPP antibodies with epitopes mapped within the identified modification region of iASPP (Residues 81-130 of SEQ Id NO: 2, FIG. 11A). Only fast-migrating cytoplasmic iASPP was recognized by LX128.5 antibody (FIG. 10B). LX49.3 recognizes iASPP outside the modified region whereas LX128.5 has an epitope that locates within the modified region (i.e., amino acids 81-130 of SEQ ID NO: 2) and modification of iASPP on S84 and 5113 destroy its epitope. Thus, LX49.3 and LX128.5 indirectly allowed us to study the phosphorylation status of iASPP in vivo. Using these mouse monoclonal antibodies it was confirmed that both nuclear iASPP and slow-migrating iASPP (also iASPPS84D/S113D) lost the epitope of LX128.5, which was recognized by LX49.3 previously (FIG. 11A). By comparing to the expression patterns of iASPP in the same panel of 18 melanoma cell lines we were able to conclude that the slow migrating iASPP detected by LX49.3 all lost their LX128.5 epitope. Thus, the slow migrating iASPP detected in this panel of cell lines are likely to be phosphorylated nuclear iASPP that is modified in the region that contains Ser84 and Ser113 (FIG. 11A, lower panels).

Figure 11B:
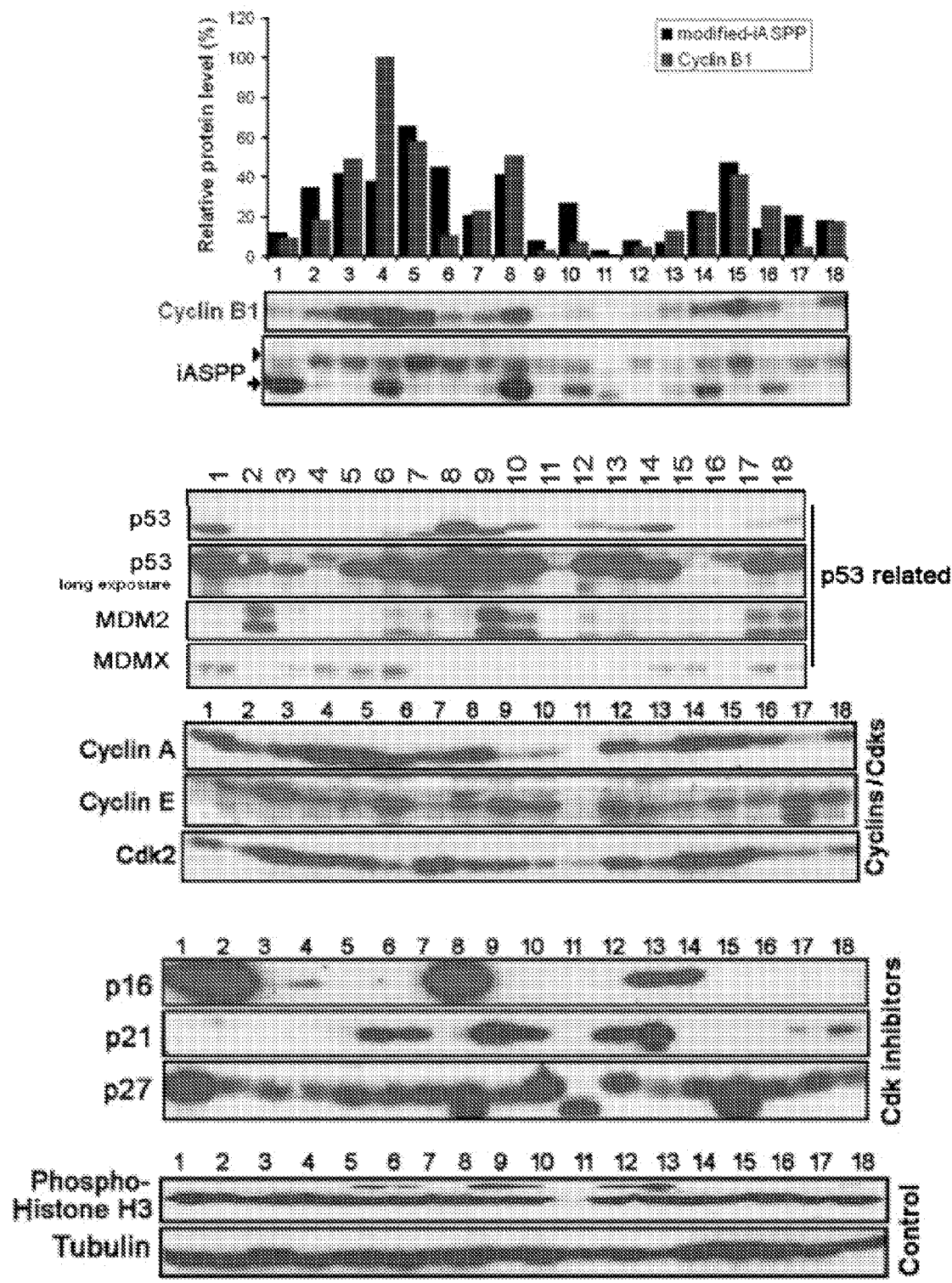
FIG. 11B. Cyclin B1 levels show association with slow-migrating iASPP levels in 18 melanoma cell lines. Upper panel: bar graph shows the relative levels of modified iASPP (bar on left side of each lane) and cyclin B1 (bar on right side of each lane) in 18 melanoma cell lines.
Figure 11C:
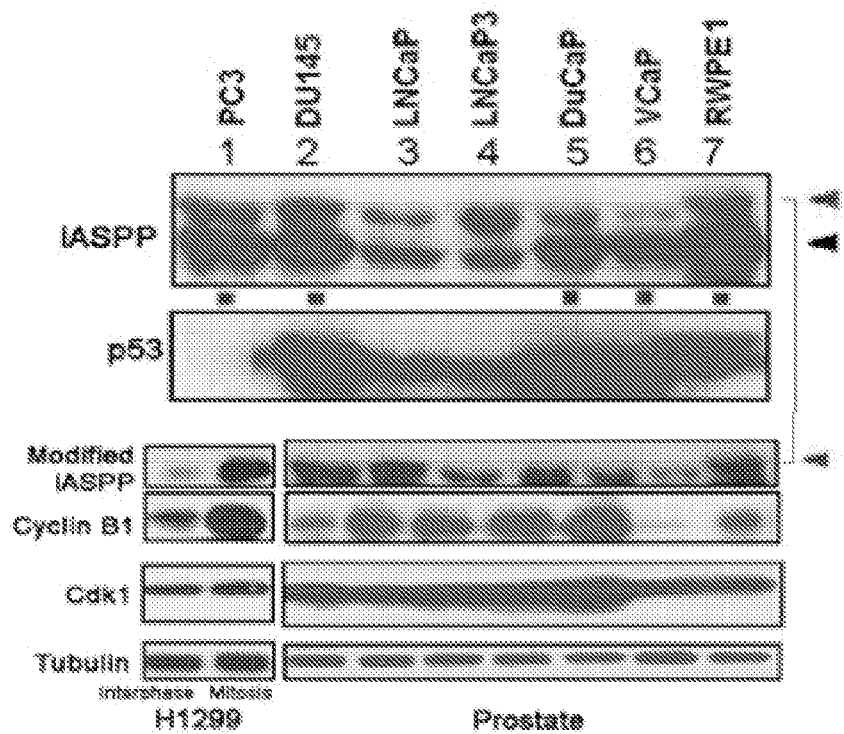
FIG. 11C. iASPP modification show positive correlation with cyclin B1 level and p53 status in prostate cancer cells; Left panel; Cell lysate from panel of prostate cancer cell lines was prepared in UREA buffer and indicated proteins were determined by WB. Right bar graph: the association between iASPP modification and cyclin B1 level/p53 status.
Figure 11C:
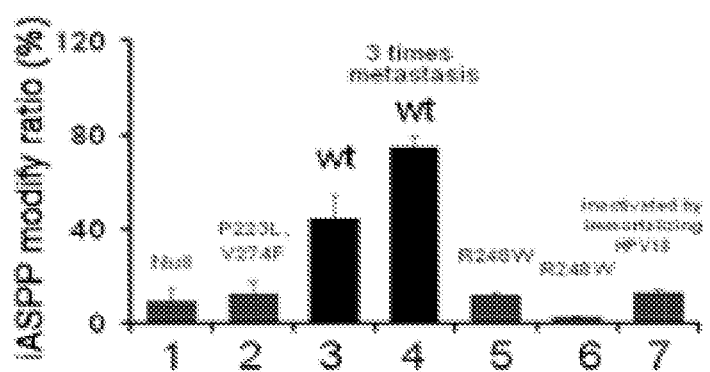
Figure 11C:
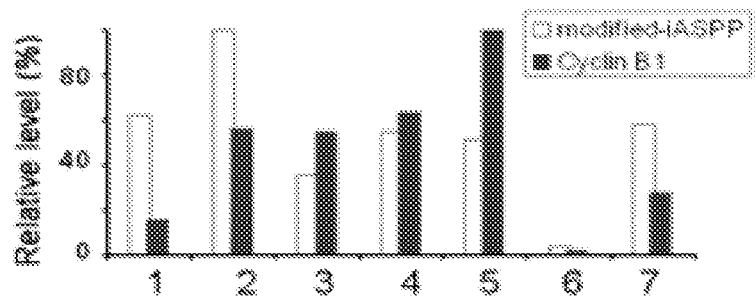

Knowing that phosphorylated nuclear iASPP is more potent in binding to p53 and inhibiting its function, we tested whether cyclinB/cdk1 phosphorylated nuclear iASPP contributes to the inactivation of p53 in highly metastatic melanomas. The panel of 18 melanoma cell lines used above were analyzed for iASPP, p53, and cyclin B1 expression. Strikingly, 91% (10/11) of the wild type p53-expressing melanoma cell lines also expressed a high ratio of phosphorylated iASPP (>50%). In contrast, 86% (6/7) of the mutated p53-expressing melanoma cell lines expressed low ratios of phosphorylated iASPP (<20%, FIG. 6A). Additionally, around 80% (9/11) of the wild type p53 cells also expressed detectable to high levels of mdm2. However, only around 45% of wild type p53 melanoma cell lines expressed detectable mdmX (5/11) under the same conditions. Importantly, around 70% of the wild type p53 melanoma cell lines express relatively high levels of mdm2 and phosphorylated nuclear iASPP. Many of the wild type p53 cell lines that expressed high levels of phosphorylated iASPP also expressed relatively high levels of cyclin B1 (FIG. 11B, bar graph). In contrast to the cyclin B1 level, the levels of phosphorylated iASPP were not linked to the expression levels of other cell cycle regulating proteins such as cdk1, cdk2, cyclin A, cyclin E, p16, p21 and p27 (FIG. 11B). The elevated cyclin B1 expression in a large number of cell lines is not simply due to an increase in the number of cells in mitosis, as the expression levels of phospho-histone H3 were different from those of cyclin B1 (FIG. 11B, lower panel), indicating that some of the melanoma cell lines have deregulated cyclin B1. Together the results suggest that deregulated cyclin B1/cdk1 may phosphorylate iASPP in interphase and enhance its ability to inhibit p53. Thus, p53 in melanoma cells is likely to be inactivated by both mdm2 and phosphorylated nuclear iASPP.

Figure 10D:
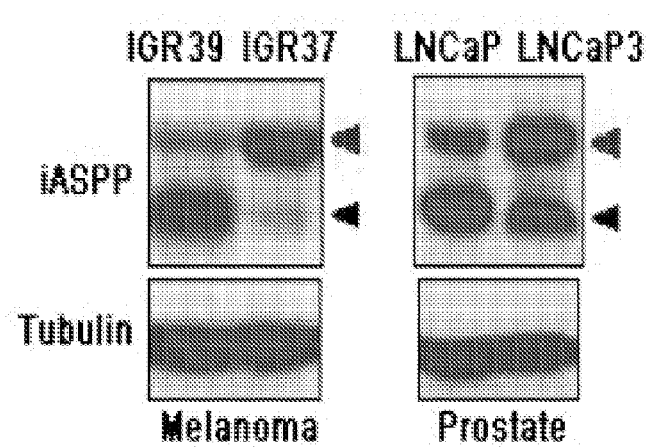
FIG. 10D. iASPP expression pattern in paired primary/metastatic cell lines. Paired human tumor cell line. IGR39 (primary) IGR37 (metastatic) LNCaP (primary) LNCaP3 (metastatic). Level of slow-migrating nuclear iASPP correlates with metastasis. Red (top) arrow heads=slow migrating modified iASPP. Black (bottom) arrow heads=fast migrating unmodified iASPP.

Using a number of paired human tumor cell lines derived from primary and metastatic tumors from the same patients, it was observed that modified iASPP is enriched in metastatic tumor cells (FIG. 10D). High levels of modified iASPP were also observed in a panel of prostate cancer cell lines PC3, DU145, LNCaP, LNCaP3, DuCaP, VCaP, RWPE1 (FIG. 11C). There was also a close association between modified iASPP level and cyclin B1 level in panels of 7 prostate cancer cell lines (FIG. 11C).

Figure 12A:
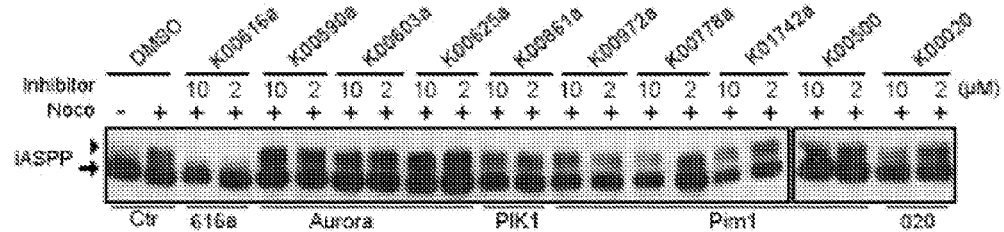
FIG. 12A. H1299 cells were co-treated with 10 µM nocodazole and indicated inhibitors against mitosis related kinase overnight. Total cells were collected and lysed in urea buffer and iASPP express pattern was determined by immunoblotting.
Figure 13A:
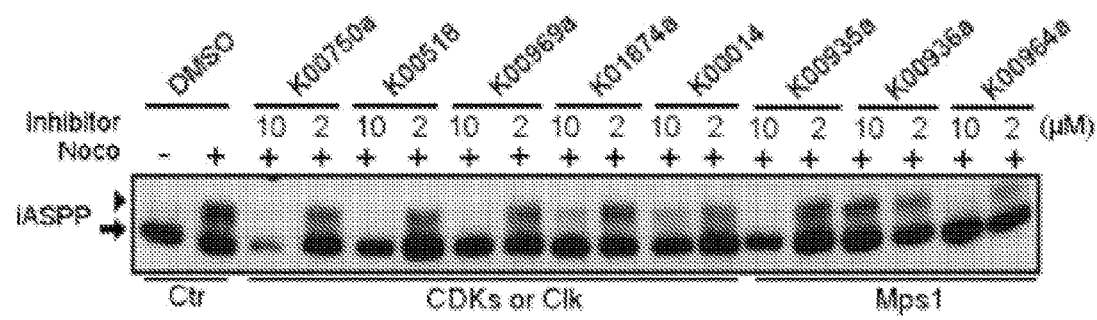
FIG. 13A. H1299 cells were co-treated with 10 µM nocodazole and indicated inhibitors against mitosis related kinase overnight. Total cells were collected and lysed in urea buffer and iASPP express pattern was determined by WB. The table shows information of inhibitors. (+)=iASPP modification is blocked (−)=iASPP modification is not blocked; (±)=iASPP modification is partially blocked. Inhibitors were supplied by Structural Genomics Consortium (Fedorov et al., 2007).

Example 8—Restoring the Tumor Suppressive Function of p53 and Inhibiting BRAF-V600E Causes Growth Suppression of Melanoma Cells As the majority of melanoma cell lines expressing wild type p53 also express phosphorylated nuclear iASPP, high levels of mdm2 and cyclin B1/cdk1, we hypothesized that cyclin B1/cdk1 inhibition together with Nutlin3 could reactivate p53 function by preventing iASPP and mdm2 from inhibiting p53 in melanoma cells. To achieve this, we needed to identify inhibitors that could prevent iASPP phosphorylation. A panel of 18 G2/M kinase inhibitors were screened for their ability prevent iASPP modification in H1299 cells, in the presence of nocodazole to induce mitosis. The results, shown in FIG. 12A and FIG. 13 and table 2 of FIG. 13, illustrated that at 2-10 µM concentrations, most inhibitors specific to Aurora kinase, Polo like kinase (PLK), Pim1 and Mps1 kinase failed to affect nocodazole-induced iASPP modification. In contrast, several inhibitors that affect the activity of cyclin B/cdk1 are able to prevent iASPP modification to various levels. The most potent inhibitor of iASPP modification in the presence of nocodazole is K00616a, an inhibitor that has the lowest IC50 for cyclin B1/cdk1 kinase activity among the panel (9 nM) (FIG. 12A). This finding is consistent with the fact that Aurora, PLK, Pim1, and Msp1 do not phosphorylate SP sites, whereas all modified iASPP sites are SP sites (Johnson 2011). Interestingly, under the same conditions, the cdk2 inhibitor roscovitine (CYC202/K0020) failed to affect iASPP modification, supporting the notion that iASPP modification in mitosis is predominantly caused by cyclin B1/cdk1. Hence, the LX128.5 negative and slow-migrating iASPP induced in mitosis is phosphorylated by cyclin B1/cdk1 in vivo and it can be inhibited by K00616a.

Figure 12B:
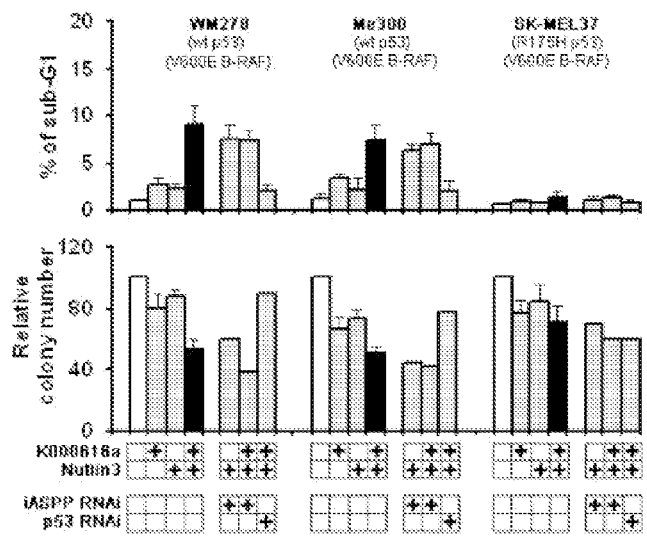
FIG. 12B. Blocking of iASPP modification by K00616a increases apoptosis sensitivity of melanomas to Nutlin3. Cells were transfected with siRNA as shown and pre-seeded on 6 well plates ON, 0.3 µM cyclin B1/cdk1 inhibitors K00616a were then added for 48 hours to block iASPP modification. Cells were then treated with 0.3 µM K00616a, 20 µM nutlin3, or combinations of these drugs for another 72 hours. Cells were collected and cell cycle status, growth potential, and protein expression pattern were then determined by PI staining/FACS analysis, colony formation assay, and WB, respectively. The upper bar graph shows the averaged sub-G1 ratio after drug treatment from 3 separated experiments; the lower bar graph shows the averaged cell colony number by seeding treated cells for 1-2 weeks.
Figure 13B:
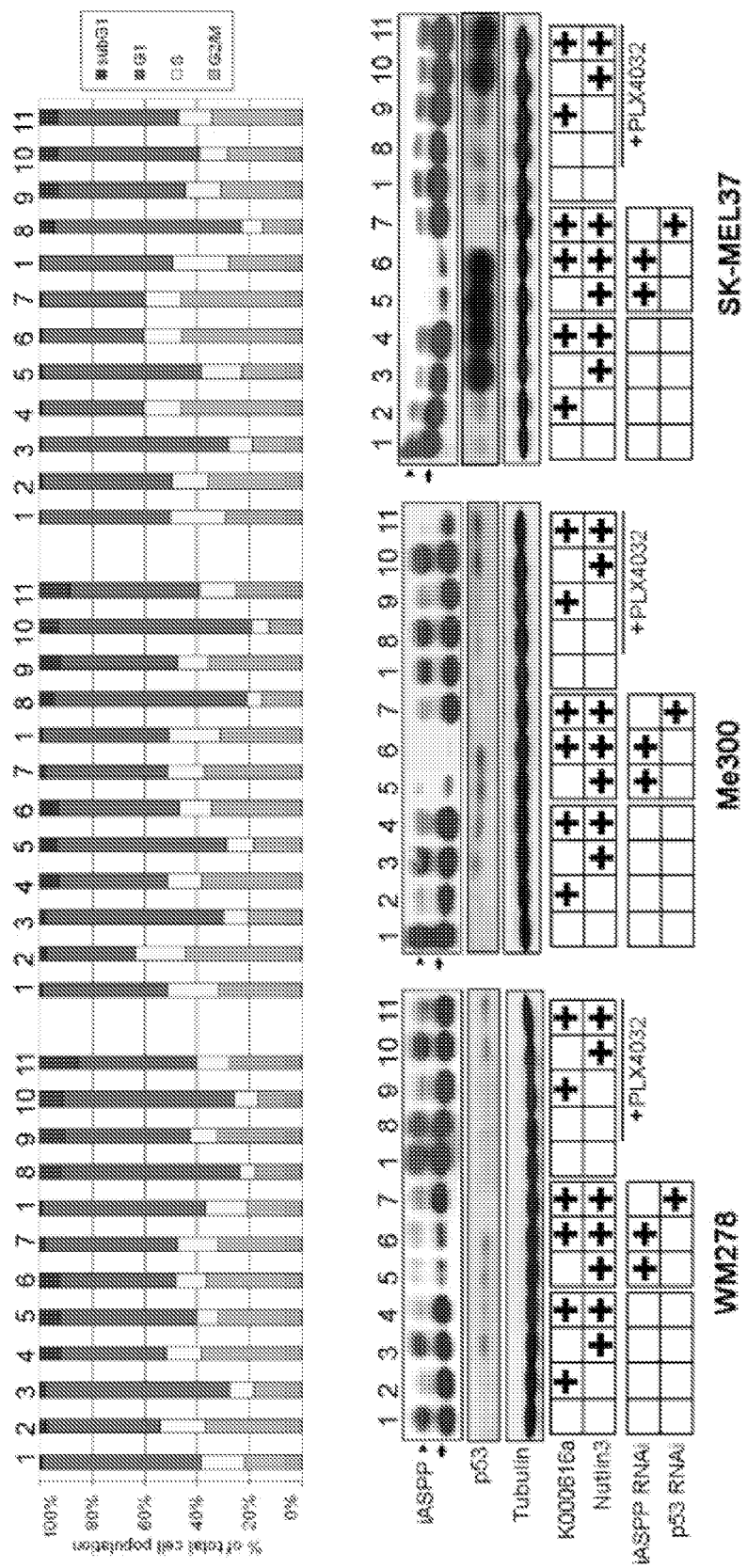
FIG. 13B. Cellular population and protein expression patterns in melanoma cells after treatments indicated in FIG. 13A. Bar graph shows the corresponding cell population in different phases of the cell cycle. SubG1 is the uppermost portion of the bars, being barely visible in lanes 1 in the first two bar graphs and is also barely visible in lanes 1-7 of the third bar graph. Lower panel shows iASPP and p53 expression patterns after indicated treatments.
Figure 14:
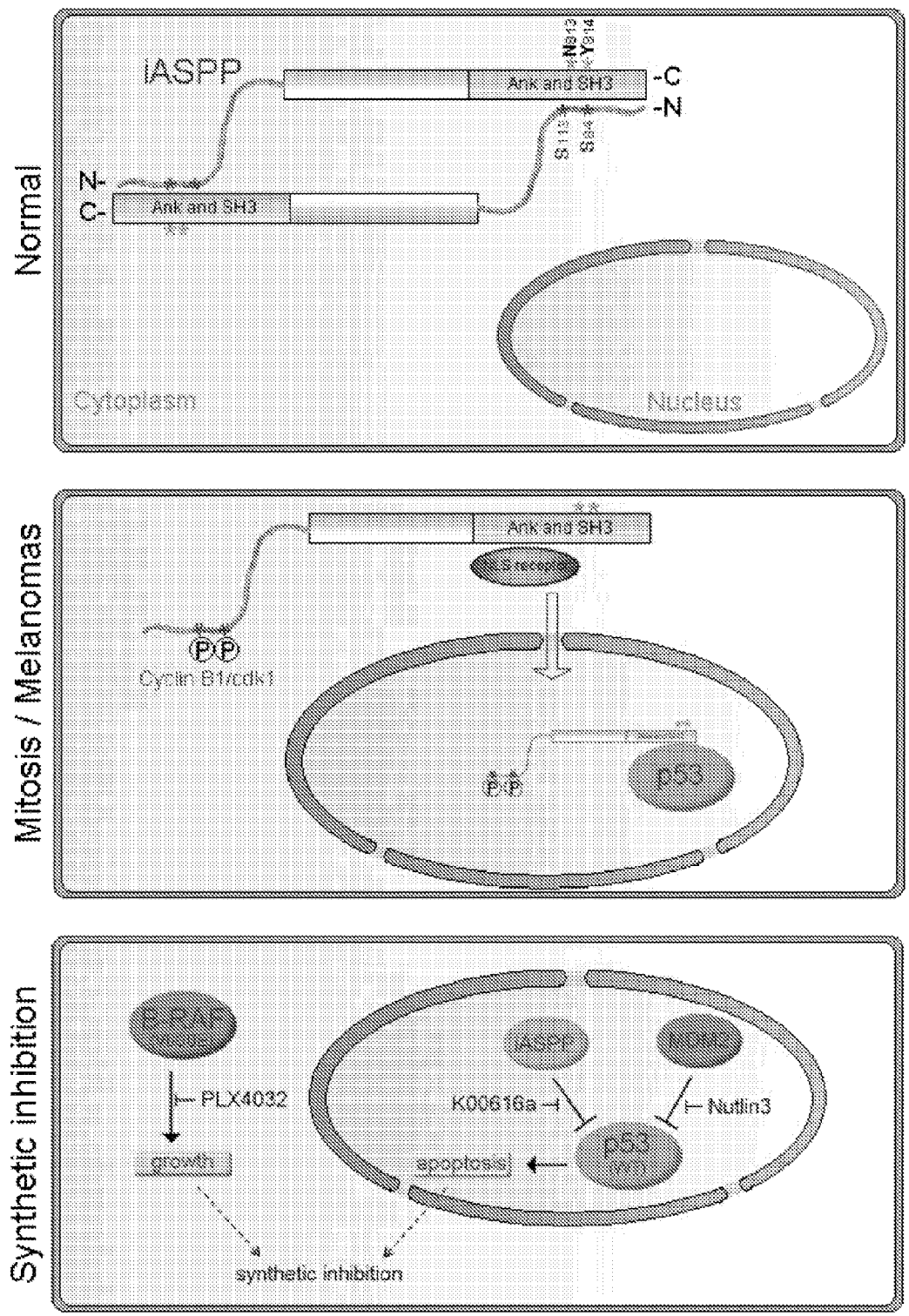
FIG. 14. S84 and S113 phosphorylation increase potential of iASPP in inhibiting p53. Normal: C-terminus of iASPP (625-828) binds N-terminus (1-240), forming iASPP dimer (or self-folded iASPP monomer). The key C-terminal nuclear localization signal (NLS, located in Ankyrin repeat domain) and p53 binding epitope (involving N813) are masked, leading to cytoplasmic localization of iASPP. Mitosis/melanoma: with cellular overexpression of cyclin B1/cdk1 (during mitosis or in some melanomas), N-terminal Ser84 and S113 are phosphorylated. This disrupts iASPP self-interaction, exposing the C-terminal NLS and p53 binding epitope. The exposed C-terminal NLS drives phosphorylated iASPP into the nucleus, where it binds to and inhibits p53. Synthetic inhibition: restoration of p53 by blocking iASPP and MDM2 increases the apoptosis sensitivity of melanoma cells that express wild type p53; blocking of the B-RAF pathway by PLX4032 suppresses the proliferation of melanoma hosting B-RAF V600E. Reactivation of p53-induced apoptosis with concurrent inhibition of the B-RAF proliferation pathway induces synthetic inhibition in melanomas.

The ability of K00616a to reactivate wild type p53 function in melanoma cells was tested in three melanoma cell lines that all express B-RAFV600E. WM278 and Me300 also express wild type p53, whereas SK-MEL37 expresses mutant p53. Cells were first treated with various combinations of Nutlin3 and K00616a in the presence or absence of RNAi of iASPP and of p53. Wild type p53 function was measured by a p53-dependent apoptosis assay, detecting the percentage of cells containing subG1 DNA content and growth suppression in a clonogenic survival assay. Under the conditions used, Nutlin3 or K00616a alone resulted in very low rates of apoptotic cell death. Similarly, their ability to suppress cell growth was also limited. The activities of Nutlin3 and K00616a were confirmed by an increase in the expression of p53 as well as the percentage of G1 or G2/M cells after the treatment (FIG. 13B). Interestingly, iASPP RNAi resulted in a two-fold increase in apoptosis, accompanied by a clear reduction in the number of colonies. This illustrates that iASPP is able to inhibit p53 independently of mdm2. Additionally, a treatment with K00616a plus Nutlin3a resulted in a two- to three-fold increase in apoptosis in both Me300 and WM278 cells. This was again accompanied with a decrease in the number of colonies detected. Importantly, the apoptosis induced by K00616a and Nutlin3 is iASPP and p53-dependent. RNAi of iASPP had little effect on K00616a and Nutlin3 induced apoptosis whereas p53RNAi prevented both the apoptosis and growth suppression induced by K00616a+Nutlin3. Consistent with this, K00616a+Nutlin3 had minimal impact in inducing apoptosis and growth suppression in SK-MEL37, which expresses mutant p53 (FIG. 12B).

Figure 12C:
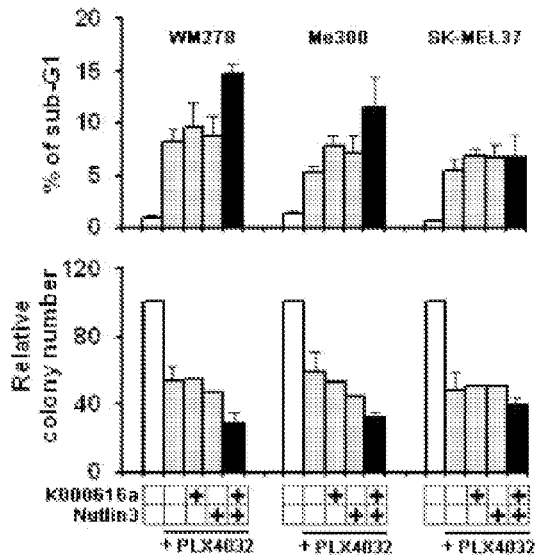
FIG. 12C. Restoring of p53 function by K00616a and nutlin3 increase apoptosis sensitivity of melanomas to PLX4032. Cells were pre-seeded on 6 well plates for overnight, 0.3 µM cyclin B1/cdk1 inhibitors K00616a were then added for 48 hours to block iASPP modification. Cells were then treated with 0.3 µM K00616a, 20 µM nutlin3, 1 µM PLX4032, or combinations of these drug for another 72 hours. Cells were collected and cell cycle status, growth potential, and protein expression pattern were then determined by PI staining/FACS analysis, colony formation assay, and WB, respectively. The upper bar graph shows the averaged sub-G1 ratio after drug treatment from 3 separate experiments; the lower bar graph shows the averaged cell colony number by seeding treated cells for 1-2 weeks.

Since K00616a+Nutlin3 is able to restore wild type p53 function in BRAFV200E expressing melanoma cell lines, WM278 and Me300, we examined whether restoring wild type p53 function and concurrently inhibiting B-RAFV600E can cause synthetic lethality. WM278, Me300 and SK-MEL37 were treated either with PLX4032, K00616a, Nutlin3 or in combination as labelled. In agreement with previous reports (Poulikakos et al., 2011), PLX4032 alone is able to induce apoptosis and growth suppression in all three cell lines tested regardless of their p53 status. K00616a or Nutlin3 alone had minimal effect on the growth suppression effects of PLX4032. High levels of apoptosis and growth suppression were observed in WM278 and Me300 cells, but not in SK-MEL37 cells, when K00616a, Nutlin3 and PLX4032 were used together (FIG. 12C). These data illustrate that the tumour suppressive function of wild type p53 can be reactivated in melanoma cells by inhibiting phosphorylated nuclear iASPP and mdm2. Restoring wild type p53 and inhibiting B-RAFV600E may cause enhanced killing of melanoma cells and could therefore provide a new strategy to treat melanomas.

Discussion:

Acquired drug resistance is the major challenge for molecularly targeted cancer therapy. Thus, the identification of ways to treat cancer cells with combined agents is of great interests. Here we show that restoring wild type p53 function and inhibiting B-RAFV600E represents a novel approach to causing synthetic inhibition in human melanoma cells. Detailed understanding of the loss of tumour suppressive function by wild type p53 in human melanoma cells led us to discover that, in addition to mdm2, p53 is inhibited by phosphorylated nuclear iASPP in melanoma cells. Knowing that deregulated cyclin B1/cdk1 may phosphorylate iASPP and cause its nuclear localisation, which increases its binding and inhibition of p53, led us to identify a cyclinB/cdk1 inhibitor, K00616a, as a potential agonist of p53. When used together with Nutlin3, it acted synergistically to restore wild type p53 function in melanoma cells. We also observed that activating p53 using K00616a plus Nutlin3 with concurrent inhibition of BRAFV600E with PLX4032 resulted in the highest observed levels of apoptosis and growth suppression in melanoma cells.

These studies are consistent with our finding that nuclear iASPP is significantly associated with lymph node metastasis melanomas in vivo. It is likely that all these observations relate to a deregulation of cyclin B1/cdk1 and an increase in iASPP Ser84 and Ser113 phosphorylation.

Besides cyclinB1 and cdk1, we further screened the expression pattern of other 24 key proteins involved in tumorgenesis of melanomas. Among these 24 proteins, the interested ASPP2, MDM2 family members, melanoma-associated antigens, familial melanomas candidate p16ink4a, Braf-Brn2-MITF-TBX2 pathway components, mitosis related cdks and cyclins, cdk5 and regulators, and prolyl hydroxylases do not show significant correlation with iASPP modify pattern, except for p53 and MAGE-C2. While MAGE-C2 show relatively weak correlation with iASPP modify pattern, p53 show strong correlation with iASPP modify pattern in both 18 melanomas and 7 prostate cancer cells. p53 cDNA were thus amplified from melanomas and their statuses were sequenced. As a result cells with a low ratio of modified iASPP universally host mutated p53 (6/7 for melanomas, 5/5 for prostate. Me248.3 is the only exception; it hosts wild type p53 mRNA, but exhibits null p53 protein level for an unknown reason. Cells with high ratio of modified iASPP universally host wt p53 (10/11 for melanomas, 2/2 for prostate). IGR37, the only exception with mutated p53 but a high iASPP modification ratio, is derived from a same patient with primary IGR39. IGR37 is established to be a malignant melanoma cell line, described to be very metastatic and tumorigenic in nude model and confirmed in human. It show high iASPP modify ratio comparing with primary IGR39 (~80% vs ~15%). It implied that iASPP might also be preferentially modified in metastatic cells. This implication was confirmed in prostate LNCaP3, the cell line derived from LNCaP after 3 times metastasis in mouse. Consistent with IGR37/39 couple, LNCaP3 show significantly increased iASPP modify ratio comparing with LNCaP (FIG. 6d, ~75% vs ~35%). The trend was also partially fit in head and neck cell couples, though it is not as dramatic as in melanomas or prostate (FIG. 6d).

Metastatic melanoma has historically been one of the most treatment refractory types of cancer due to its resistance to apoptosis (Soengas Lowe 2003) and high metastatic potential (Flaherty, 2011). Mutation of p53 is a common feature of cancer, and there is emerging evidence that mutant p53 promotes cancer metastasis, but a large percentage of melanomas are highly metastatic while expressing wild type p53. It is currently estimated that around 80% of melanomas express wild type p53 and around 50% are highly metastatic. In an attempt to understand why wild type p53 loses its tumour suppressive function in metastatic melanoma, Avery-Kiejda et al. identified abnormal expression of a large number of p53 downstream target genes, including a failure to upregulate p53 induced pro-apoptotic genes such as Bax and PIG3 in melanomas (Avery-Kiejda et al., 2011). Similarly, Houben et al. also reported defects in the transcriptional activity of p53 using reporters of p53 target genes (Houben et al., 2011). All these studies agree with our finding here that the transcriptional activity, and in particularly the apoptotic function, of p53 is largely inactivated in melanomas. The tight association between the expression levels of phosphorylated nuclear iASPP and wild type p53 status (over 90%) supports the notion that the identified phosphorylated nuclear iASPP represents a key inhibitor of p53 in melanomas, in addition to mdm2, mdm4 and other cellular inhibitors (Polsky et al., 2002; Schittek et al., 2007). This is supported by the finding that the tumour suppressive function of p53 in melanomas can only be restored by inhibiting both mdm2 and iASPP phosphorylation, using Nutlin3 and K00616a, respectively.

The results demonstrated herein is a proof of principle that targeting two independent pathways that are important in melanoma development and maintenance may prove to be fertile ground for the development of strategies to treat malignant melanoma. Furthermore, the identified mechanism by which cyclin B1/cdk1 phosphorylated nuclear iASPP is a potent inhibitor of p53 suggests that nuclear iASPP may be a good biomarker for the tumour suppressive function of p53 in tumours that express wild type p53.

Example 9—Phosphorylation of iASPP at S84/S113 by Cyclin B1/Cdk1 Contributes to iASPP Slow Migration and Nuclear Localization in Multiple Melanoma Cell Lines It has been shown in human NSCLC H1299 cells that the phosphorylation of iASPP at Ser84/Ser113 by cyclin B1/cdk1 contributes to iASPP slow migration (see Example 4). Similar experiments were performed to assess iASPP phosphorylation in other cell lines. In addition to those reported observations in human NSCLC H1299 cells, the phosphorylation of iASPP at S84/S113 by cyclin B1/cdk1 contributes to iASPP slow migration and nuclear localization in SK-MEL37, B16, and WM278 melanoma cells. These experimental results confirm that the observed regulation of iASPP migration is a general phenomenon in melanoma cells.

Example 10—JNJ-7706621, an Inhibitor of Cyclin B1/CDK1, Nocodazole-Induced iASPP Modification Nocodazole was used to induce cells to enter into mitosis, a cellular state in which CDK kinases are active. To determine if other kinase or CDK-specific inhibitors could inhibit nocodazole-induced iASPP modification in H1299 cells, experiments were carried out with a panel of 15 G2/M kinase inhibitors.

Immunohistochemistry Staining and Patient Survival Analysis.

Immunohistochemical staining was similar to that described previously (Notari et al., Proc. Natl. Acad. Sci. USA 108, 16645-50, 2011). Tissue sections were dewaxed, rehydrated and incubated with 3% hydrogen peroxide in methanol to block endogenous peroxidase activity (10 min). Prior to incubation, antigen retrieval was carried out in microwaved sodium citrate buffer (pH 6.0) for 10 min for cyclin B1 staining only. Sections were then blocked with normal goat serum (NGS), incubated overnight at 4° C. with the primary antibody, followed by the biotinylated secondary antibody for 40 min at room temperature. Avidin-Biotin Immunoperoxidase-Complex Vectasatin Elite Reagent was used to amplify the signal and the peroxidase substrate Vector VIP was used to visualize the complexes. Sections were counterstained with Methyl Green, dehydrated, permanently mounted, and photographed. Expression of iASPP in the nucleus was scored as the product of staining intensity (0-none, 1-weak, 2-moderate, 3-strong) and the proportion of cells exhibiting this stain (0-100% in 5-10% increments) to generate an Overall Expression score (0-300). All tumor cells showed cyclin B1 expression. Therefore, expression levels were compared using an intensity score only (1-weak, 2-moderate, 3-strong). Statistical analysis was undertaken in SPSS. Difference between groups were analyzed by the Mann-Whitney test (U) where the effect size is denoted by $r=z/\sqrt{n}$ (>0.3=medium effect, >0.5=large effect). The relationship between nuclear iASPP, dichotomized around the upper quartile, in primary and metastatic tumors was evaluated using a Chi-squared test where the effect size was determined by the odds ratio. For survival analysis, a multivariate Cox proportional hazards model was used, controlling for known prognostic factors (including age, gender, site, thickness, and ulceration).

Xenograft Assay.

Figure 19E:
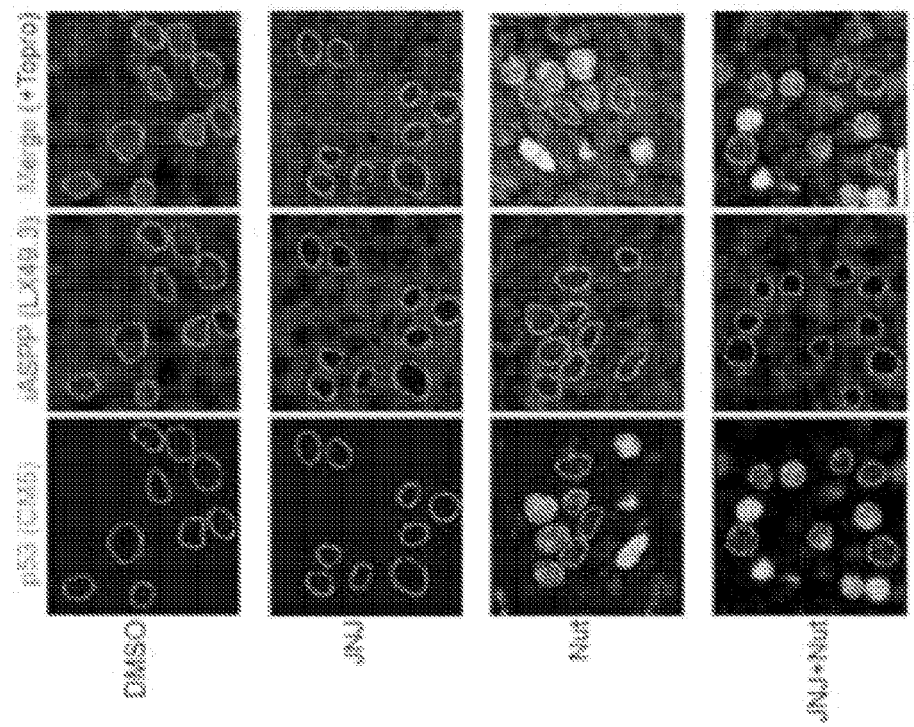
FIG. 19E. Representative immunofluorescence staining of iASPP and p53 in tumor section derived from FIG. 19D. White dotted circles show the representative nuclear rim derived from Topro staining. Bar=20 μm. (C-D), treated or untreated B16 cells (1×10$^6$) were subcutaneously injected into C57BL/6 mice at day 1 and tumor sizes were measured every two days. Tumors were weighted at the end-point (day 13).
Figure 19D:
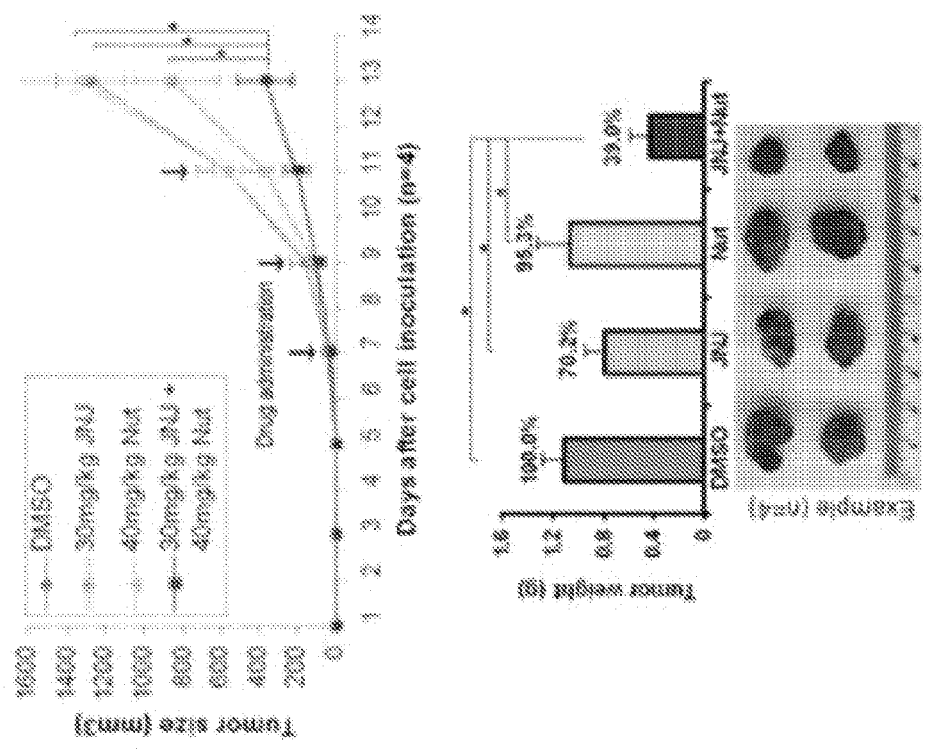
FIG. 19D. Untreated B16 cells were subcutaneously injected into flanks of mice at day 1. At day 7, tumors were visible, and compounds (i.e., JNJ, Nutlin3, JNJ+Nutlin3, and control vehicle (DMSO)) were intraperitoneally (i.p) injected. Compound administration and tumor size measurements were repeated every two days from day 7 onwards. Bar graphs are shown as mean±SD (*p<0.05, n=4). Lower panels show representative image of isolated tumors.
Figure 20B:
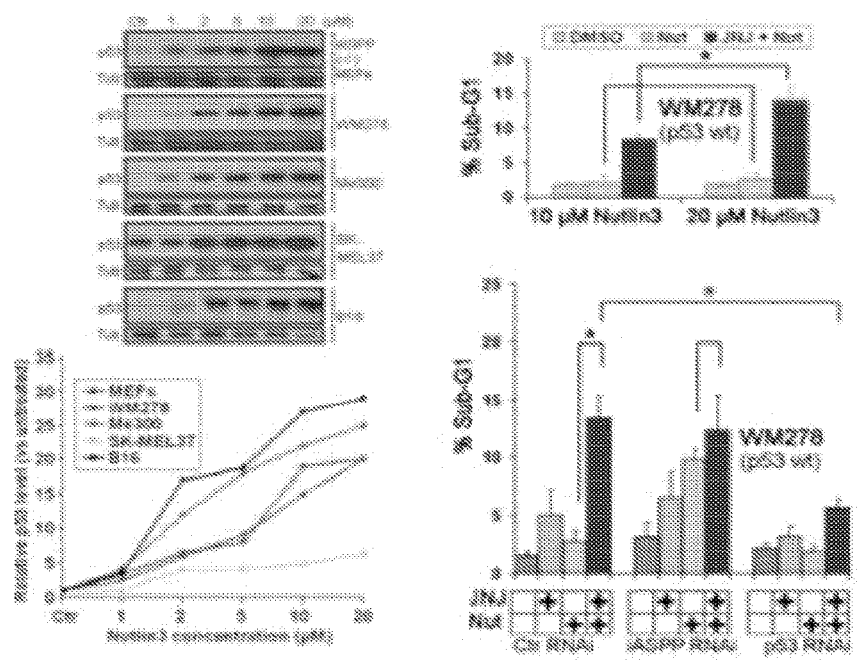
FIG. 20B. Left panel: representative p53 level after Nutlin3 treatment for 24 hours in a variety of cells. Right bar graphs show the sub-G1 proportion of WM278 after treatment as that described in FIG. 19B (in upper panel, 10 μM and 20 μM Nutlin3 were used in parallel for comparison). From left to right of the upper right bar graph of FIG. 20B, the bars correspond to DMSO, Nut and JNJ+Nut, respectively. From left to right of the bottom bar graph of FIG. 20B, the bars correspond to DMSO, JNJ, Nut and JNJ+Nut, respectively.
Figure 20C:
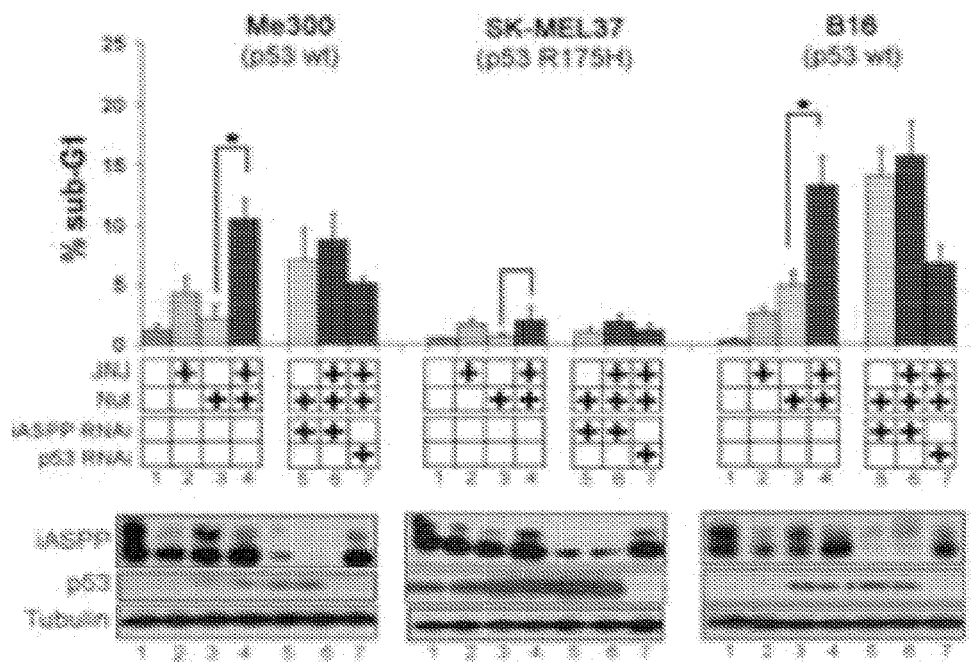
FIG. 20C. Me300, SK-MEL37, and B16 cells were treated as above (For B16 panel, 10 μM Nutlin3 was used) and sub-G1 proportion was analyzed. In (B) and (C), the bar graphs (mean±SD) were derived from three independent experiments. *p<0.05.
Figure 20D:
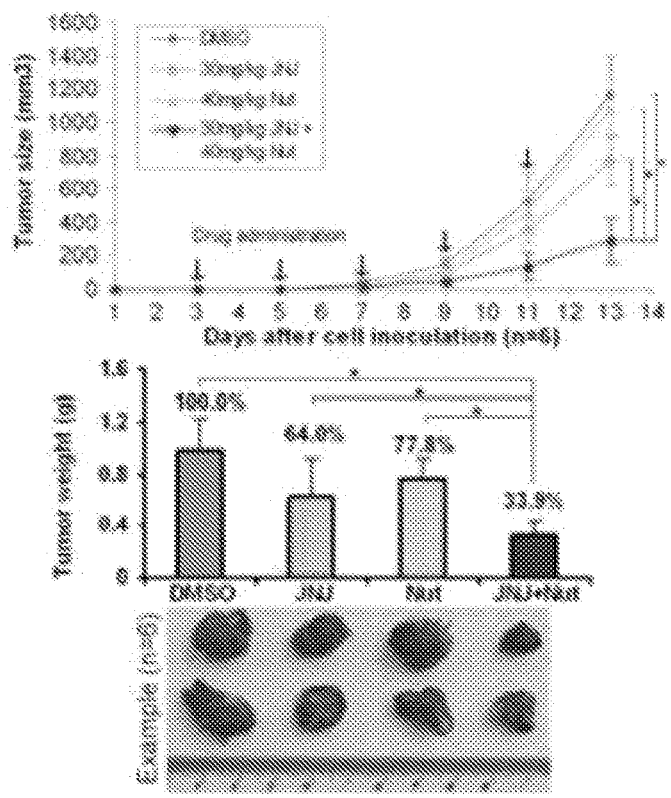
FIG. 20D. Left panel: untreated B16 cells were subcutaneously injected into mice at day 1. At day 3, cells settled down and JNJ, Nutlin3, JNJ+Nutlin3, and control vehicle (DMSO) were intraperitoneally (i.p) injected. Compound administration and tumor size measurement were repeated every two days from day 7 onwards. Bar graphs are shown as mean±SD (*p<0.05, n=6).
Figure 20E:
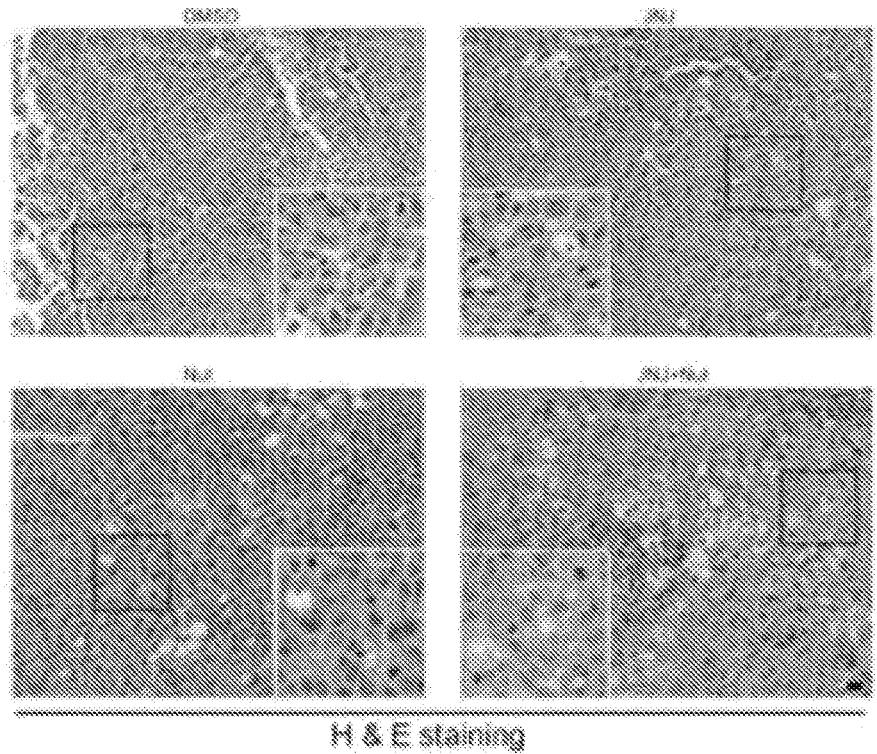
FIG. 20E. Lower panels show representative images of isolated tumors. Right panel: representative H & E staining in B16 tumor section. Bar=20 μm.

At day 1, C57BL/6 mice (7-9 weeks old) were injected s.c. at flanks with $1\times10^6$ B16 melanoma cells in 100 µl PBS (component treated cells for FIG. 19C, untreated cells for FIGS. 19D and 20D). Component (Nutlin3 (40 mg/kg) or JNJ-7706621 (also referred to herein as "JNJ", 30 mg/kg)) was dissolved in DMSO and i.p. administered every two days since day 3, or day 7 (no component administration for FIG. 19C). Tumor size was measured every two days with vernier caliper. Tumor volumes were calculated using the following formula: (L*W*W)/2, in which L represents the larger diameter of the tumor, and W represents the smaller diameter. On day 13 (tumor area reach ~1.2 cm diameter in DMSO group), all mice were sacrificed and tumors were isolated and weighed.

FACS Analysis and Colony Formation Assay.

Cells were incubated with either DMSO or the cyclin B1/cdk1 inhibitor JNJ-7706621 (0.4 µM) for 48 hours to block iASPP modification. Cells were digested and transfected with siRNA using DharmaFECT 1 Transfection Reagent kit (T-2001-02) and seeded on 6-well plates in fresh medium containing DMSO, JNJ (0.4 µM), Nutlin3 (10-20 µM), PLX4032 (1-5 µM), or indicated combinations for 72 hours. Treated cells were collected and used for the following three assays. For Sub-G1 analysis, cells were fixed in ice-cold 70% EtOH. After washing, cells were incubated in PBS containing 0.05 mg/ml RNase A and 0.05 mg/ml propidium iodide (P4864, Sigma) for 30 minutes at room temperature. The percentage of subG1 DNA content-containing cells was determined by FACS analysis using BD FACSCanto Flow Cytometer (BD Biosciences) and was used as indication of apoptosis. For Annexin V/7-AAD analysis, 100 µl PBS washed cells ($1\times10^6$ cells/ml) were incubated in binding buffer (BD Pharmingen, 559763) with 5 µl Annexin V and 5 µl 7-AAD for 15 min at room temperature in the dark. Binding buffer (400 µl) was added and cells were subjected to FACS analysis for 1 hour. The percentage of Annexin V positive cells was used as indication of apoptosis. For colony formation assays, 100, 1000 or 10,000 cells/well were seeded in 6-well plates and kept in culture for 8-14 days. Fresh medium was replaced every three days.

S84/S113 Phosphorylated Nuclear iASPP is Enriched in Wild Type p53 Expressing Melanoma Cells.

Figure 18A:
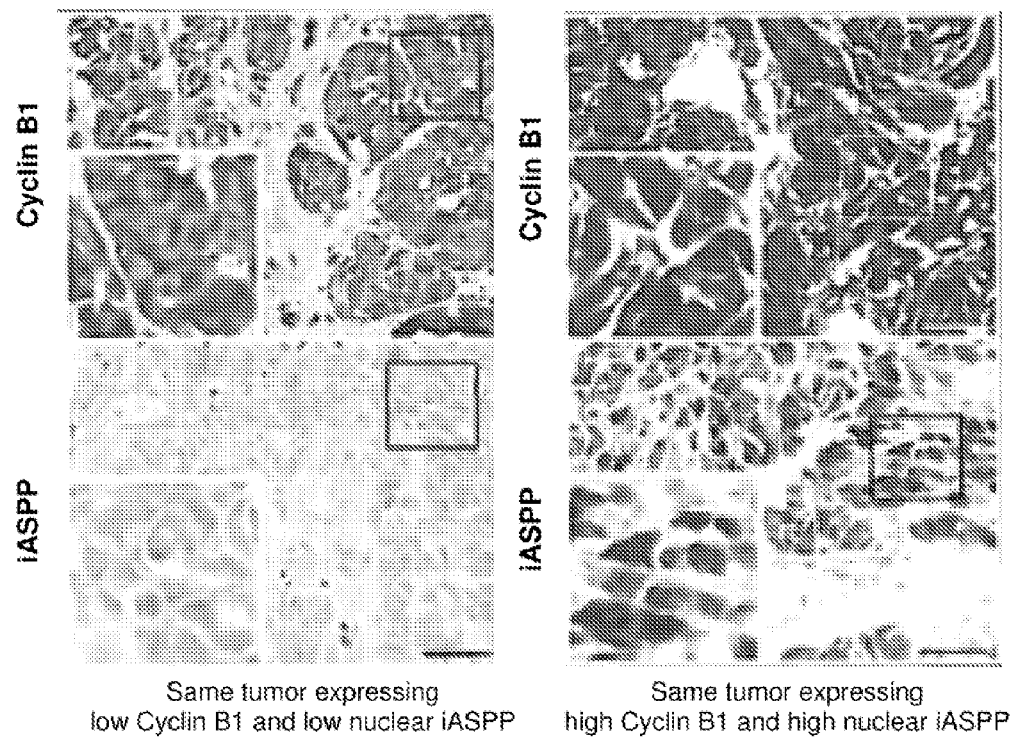
FIG. 18A shows representative iASPP and cyclin B1 staining patterns in 142 human melanoma tissue microarray cores (left panel). Bar=50 μm. Tumors expressing strong cyclin B1 showed significantly higher nuclear iASPP levels (U=340.500, r=−0.28, p<0.05) (right panel).

As demonstrated herein, melanoma cell lines have deregulated cyclin B1 in cells in interphase, which is associated with iASPP modification and nuclear localization. The association between cyclin B1 and nuclear iASPP expression was examined in human melanomas. Consistent with the in vitro finding, a strong correlation between strong cyclinB1 staining and high nuclear iASPP expression was observed in human melanomas (FIG. 18A), which is associated with poorer patient survival.

Figure 18B:
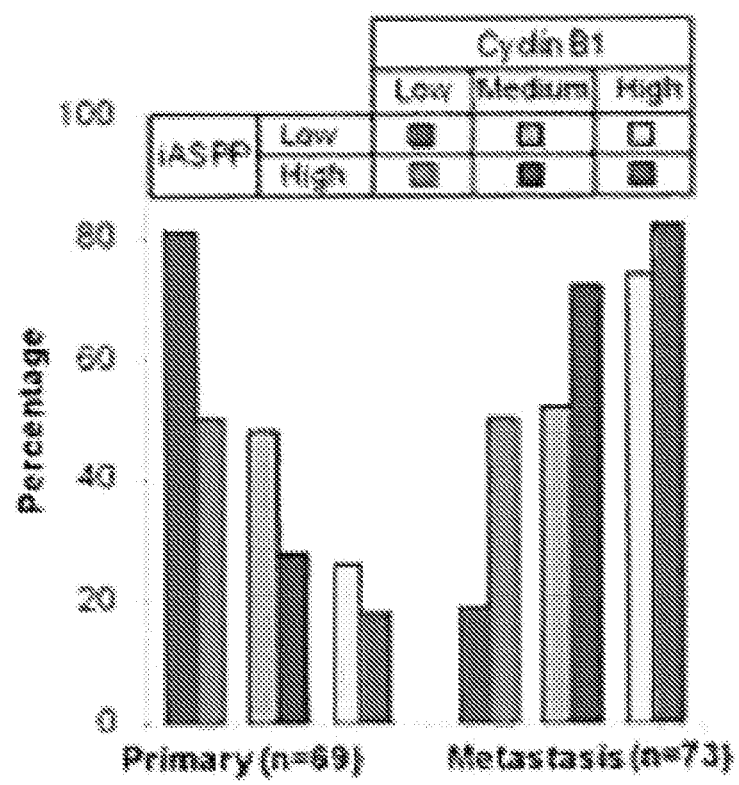
FIG. 18B shows that lymph node metastatic tumors ("metastasis" right panel) demonstrate greater occurrence of high cyclin B1 and high nuclear iASPP expression compared to primary tumors ("primary" left panel). The bars provided in the "primary" panel from left to right are as follows: low iASPP/low cyclin B1; high iASPP/low cyclin B1; low iASPP/medium cyclin B1; high iASPP/medium cyclin B1; low iASPP/high cyclin B1 and high iASPP/high cyclin B1. The bars provided in the "metastasis" panel from left to right are as follows: low iASPP/low cyclin B1; high iASPP/low cyclin B1; low iASPP/medium cyclin B1; high iASPP/medium cyclin B1; low iASPP/high cyclin B1 and high iASPP/high cyclin B1. A survival curve shows that high nuclear iASPP correlates with poor survival in all of three groups of cyclin B, i.e., groups expressing low, medium, and high cyclin B1 (p=0.033).
Figure 18B:
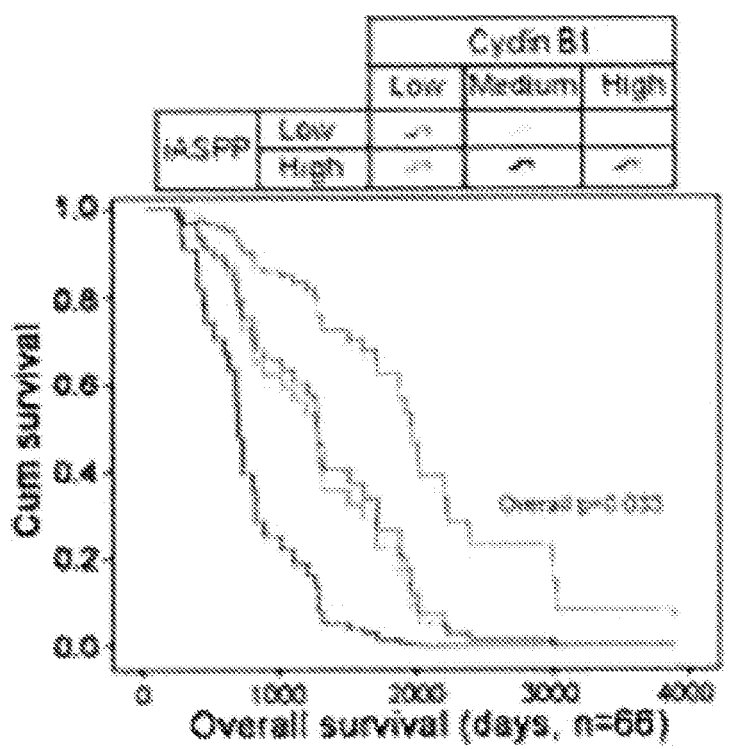

To investigate the relationship between cyclin B1 and nuclear iASPP in primary tumors and in metastasis, samples were divided into six groups depending on how they expressed iASPP and cyclin B (low or high iASPP with either low, medium, or high cyclin B (FIG. 18B)). Tumors that showed weak or low cyclinB1 and low nuclear iASPP expression were shown to be predominantly primary melanomas. Tumors that showed strong or high cyclin B1 staining/expression and high nuclear iASPP expression were mainly found in metastasis (FIG. 18B, bar graph). In a cohort of 66 melanoma patients, high nuclear iASPP was significantly associated with poor survival, whereas strong cyclinB1/low nuclear iASPP was not associated with poor survival. The data therefore indicates that deregulated cyclin B1 alone may not be sufficient to affect survival (FIG. 18C, survival curve). Without being bound by theory, these results suggest that deregulated cyclin B1/cdk1 may phosphorylate iASPP in interphase and enhance its ability to inhibit p53.

Restoring p53 by Inhibiting Mdm2 and iASPP Suppresses Melanoma Growth In Vitro and In Vivo.

Knocking down cyclin B1 with RNAi abolished the slow-migrating iASPP in the presence of nocodazole. Increased expression of cyclin B1, but not cdk1, induced nuclear localization of iASPP in H1299 cells, confirming that cdk1 is present in excess in cells and cyclin B1 dictates the kinase activity of cyclin B1/cdk1 and cyclin B1/cdk1 phosphorylates iASPP and causes its nuclear entry (FIG. 19A).

A panel of 15 G2/M kinase inhibitors was tested for their ability to prevent nocodazole induced iASPP modification in H1299 cells. At 2-10 µM concentrations, most inhibitors against Aurora kinase, Polo-like kinase (PLK), Pim1, or Mps1 kinase failed to abrogate nocodazole-induced iASPP modification. In contrast, several inhibitors that are known to affect the activity of cyclin B1/cdk1 were able to inhibit iASPP modification. The most potent inhibitor of iASPP modification in the presence of nocodazole was JNJ-7706621 (JNJ) (Emanuel et al., *Cancer Res.* 65(19):9038-46, 2005, incorporated herein by reference in its entirety), a cdk1 inhibitor with an in vitro IC50 of 9 nM for cyclin B/cdk1. Under the same conditions, the cdk2 inhibitor Roscovitine only weakly affected iASPP modification (FIG. 19A and FIG. 20A: Table 2). To provide supporting evidence that p53 selectively binds cyclinB1/cdk1 phosphorylated nuclear iASPP, WM278 cells were treated with DMSO (control), nocodazole, or JNJ. The treated cell lysates were incubated in the presence or absence of a Ser/Thr phosphatase (calf intestine phosphatase, CIP) for 1 hour before immunoprecipitation. JNJ alone reduced the amount of modified iASPP whereas nocodazole induced iASPP modification. CIP treatment was able to abolish nocodazole induced iASPP modification. Importantly, p53 failed to co-immunoprecipitate iASPP in JNJ, control+CIP and Nocodazole+CIP-treated lysates, even though p53 was efficiently co-immunoprecipitated with modified iASPP in both control and nocodazole treated WM278 cells (FIG. 20A). These data illustrate that p53 selectively binds phosphorylated iASPP in vivo.

JNJ demonstrated activity similar to activity of K00616a. For example, JNJ was able to prevent iASPP from binding to p53. Knowing that JNJ blocks iASPP from binding to p53, the ability of JNJ to reactivate wild type p53 function in melanoma cells was tested in four melanoma cell lines: B16, WM278, Me300, and SK-MEL37. B16, WM278, and Me300 express wild type p53, whereas SK-MEL37 expresses mutant p53. Cells were first treated with various concentrations of Nutlin3 to prevent degradation of p53. Optimal concentrations of Nutlin3 to induce maximal p53 expression were identified as 2 µM for SK-MEL37, 10 µM for B16, and 20 µM for both WM278 and Me300 cells (FIG. 20B). Cells were then treated with various combinations of Nutlin3 and JNJ in the presence or absence of RNAi for iASPP and for p53. Nutlin3 or JNJ alone induced apoptosis in only a small percentage of cells. The ability of Nutlin3 or JNJ to suppress cell growth was also limited, even though both Nutlin3 and JNJ were able to induce p53 expression or G2/M arrest, respectively. In B16, Me300, and WM278 cells, treatment with iASPP RNAi or JNJ resulted in a 3-4 fold increase in Nutlin3-induced apoptosis, which was determined by the presence of cells expressing Annexin V (FIG. 19B) or containing Sub-G1 DNA content (FIGS. 20B and 20C). Apoptosis induced by JNJ+Nutlin3 was iASPP- and p53-dependent. In the presence of iASPP RNAi, JNJ failed to further enhance Nutlin3 induced apoptosis. p53 RNAi largely prevented both apoptosis and growth suppression induced by JNJ+Nutlin3. JNJ+Nutlin3 had minimal impact in inducing apoptosis and growth suppression in SK-MEL37 melanoma cells (FIG. 20C).

Mouse B16 melanoma cells are known to form highly aggressive melanoma in vivo in immune competent C57BL/6 syngeneic mice. Because regulation of p53 by iASPP and mdm2 exists in both human WM278 cells and mouse B16 cells, experiments were carried out to determine if restoring p53 function in B16 cells is able to suppress tumor growth in C57BL/6 mice in vivo. B16 cells, treated with (1) DMSO, (2) Nutlin3, (3) JNJ, or (4) Nutlin3+JNJ, were injected into the flank of 7-9 week-old female C57BL/6 mice. At 13 days after injection, tumor size and weight in mice injected with JNJ, Nutlin3 or JNJ+Nutlin3-treated B16 cells was around 40%, 60% or 15%, respectively, of control (tumor size and weight in DMSO-treated B16 cell group (FIG. 19C). JNJ was a more potent inhibitor of B16 growth in vivo than in the colony assay.

The ability of Nutlin3+JNJ to inhibit B16 melanoma growth in vivo was further tested by inoculating untreated B16 cells into C57BL/6 mice three or seven days prior to the intraperitoneal administration of DMSO, Nutlin3, JNJ or Nutlin3+JNJ, every two days as indicated. Treatment with Nutlin3+JNJ together was able to suppress tumor weight/size of B16 melanomas by 61-66% compared to that of control (DMSO). Administration of Nutlin3 at day 3 or day 7 after B16 inoculation suppressed B16 melanoma growth by 22% or 5%, respectively. JNJ treatment at both time points suppressed B16 melanoma growth by 36% or 30%, respectively in vivo (FIGS. 19D and 20D). Without being bound by theory, these results indicate that the timing to inhibit mdm2 in vivo may affect the efficacy of Nutlin3. However, the efficacy of JNJ or JNJ+Nutlin3 in inhibiting B16 melanoma growth was less sensitive to administration time.

Both cytoplasmic and nuclear iASPP were detected in DMSO-treated B16 tumors, and under the same conditions, p53 expression was almost undetectable. Treatment with JNJ clearly reduced nuclear iASPP expression in B16 tumors, while it had no effect on p53 expression. Nutlin3 treatment induced nuclear p53 expression and had minimal impact on iASPP expression. Treatment with JNJ+Nutlin3 resulted in a reduction in nuclear iASPP and an increase in nuclear p53 (FIG. 19E). Thus, it was found that the tumor-suppressive effect of JNJ is associated with a reduction in nuclear iASPP expression in B16 tumor cells in vivo. Combined treatment with JNJ and Nutlin3 is able to restore the tumor suppressor function of p53 and to inhibit melanoma growth in vivo.

Restoring the Apoptotic Function of p53 Cooperates with BRAFV600E Inhibition to Suppress Human Melanoma Cell Growth.

Figure 21B:
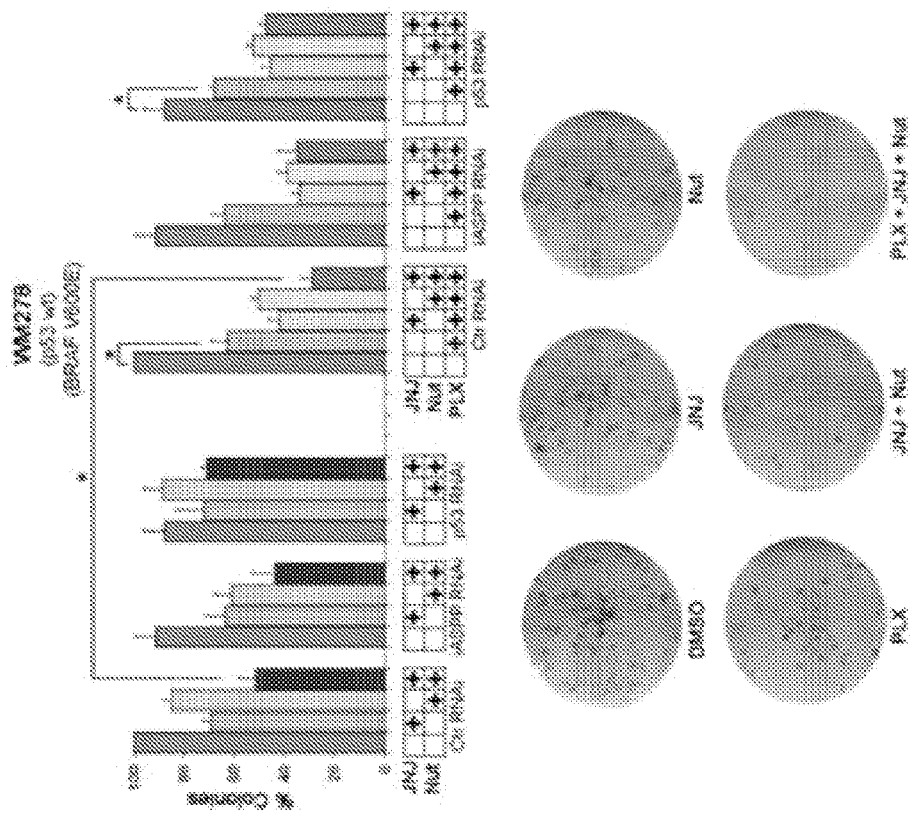
FIG. 21. Restoring apoptotic function of p53 cooperates with BRAFV600E inhibition to suppress human melanoma cell growth. WM278 cells were treated with 0.4 μM JNJ, 20 μM Nutlin3, 1 μM PLX4032, or combinations as indicated in the presence or absence of control, iASPP or p53 RNAi as indicated. The upper bar graph (FIG. 21A) shows the percentage of Annexin V positive cells and the lower bar graph (FIG. 21B) shows the percentage of treated cells that formed colonies. The bar graphs (mean±SD) were derived from three independent experiments. *p<0.05. Lower images show representative Annexin V/7-AAD profile and dishes, respectively.
FIG. 21C. Diagrams showing how cyclinB1/cdk1 phosphorylation controls iASPP localization in interphase (interphase) or mitosis or tumor cells (mitosis/melanomas). Blue and red stars (*) indicate the C- and N-terminal contact residues and the phosphorylation status is labeled as (P). The bottom diagram summarizes the pathways that PLX4032, Nutlin3 and JNJ used to suppress melanoma cell growth.
Figure 21A:
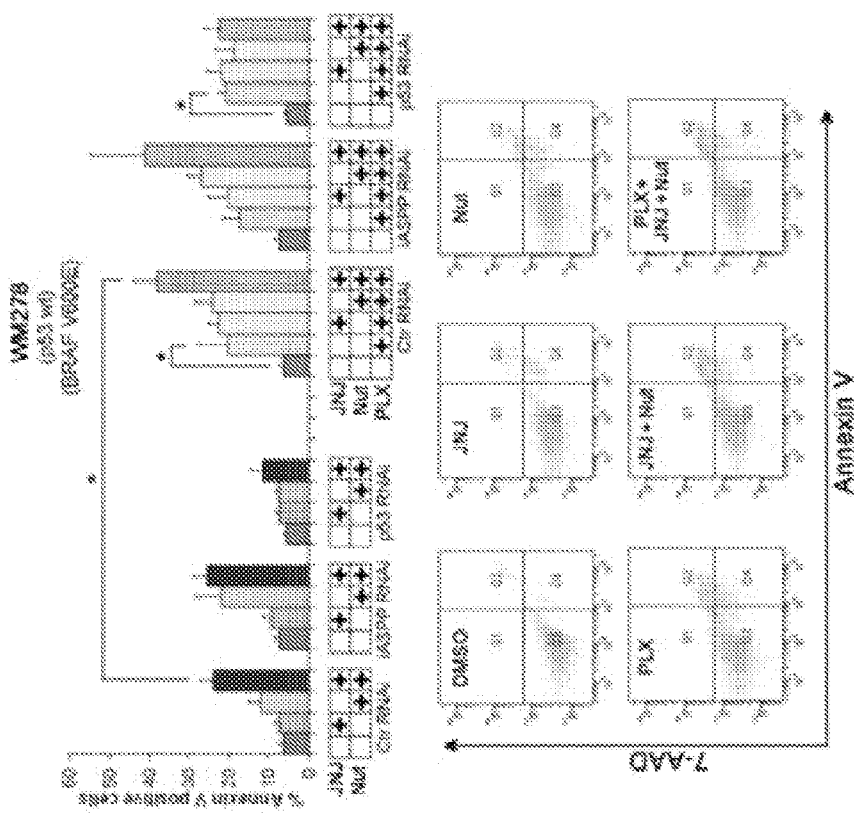
Figure 21C:
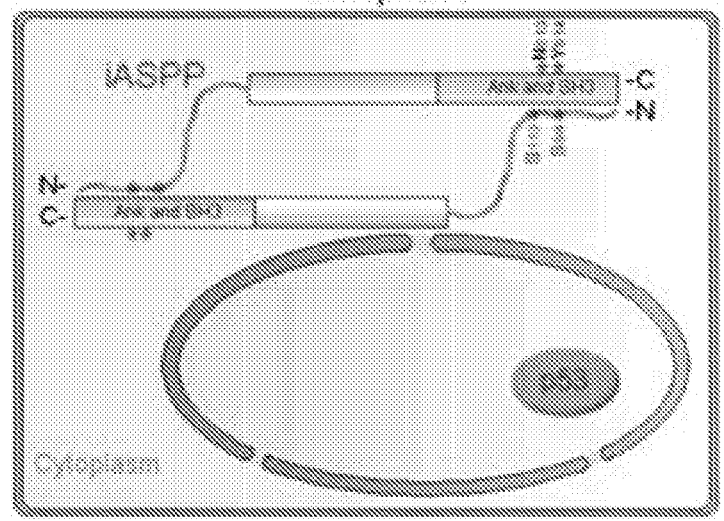
Figure 21C:
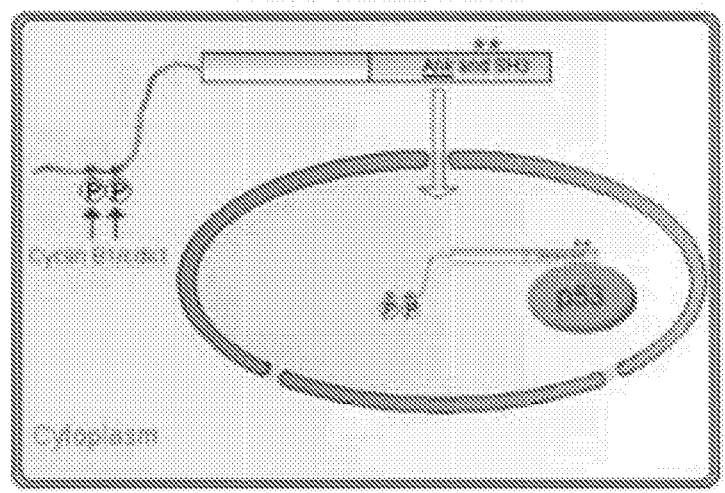
Figure 21C:
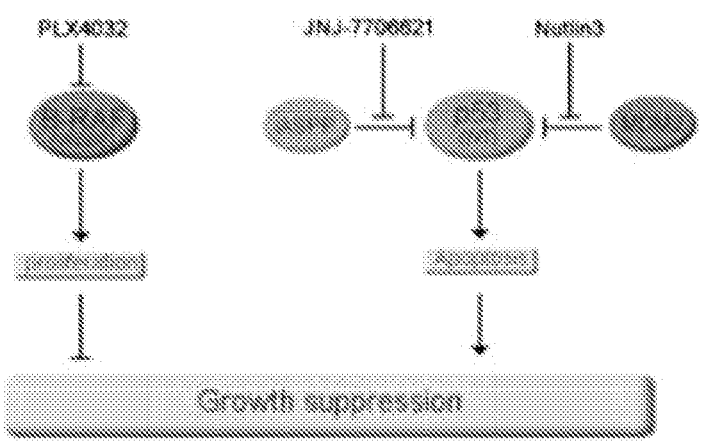
Figure 22A:
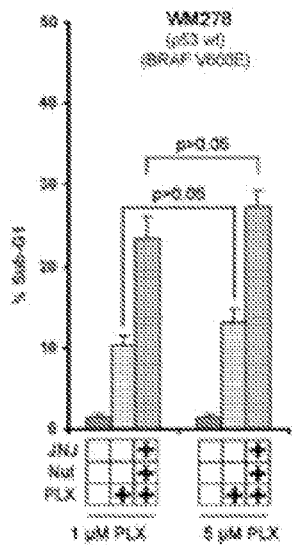
FIG. 22A. Bar graph shows the sub-G1 proportion of WM278 after treatment as described in FIG. 21A. 1 µM and 5 µM PLX4032 were used in parallel for comparison.
Figure 22B:
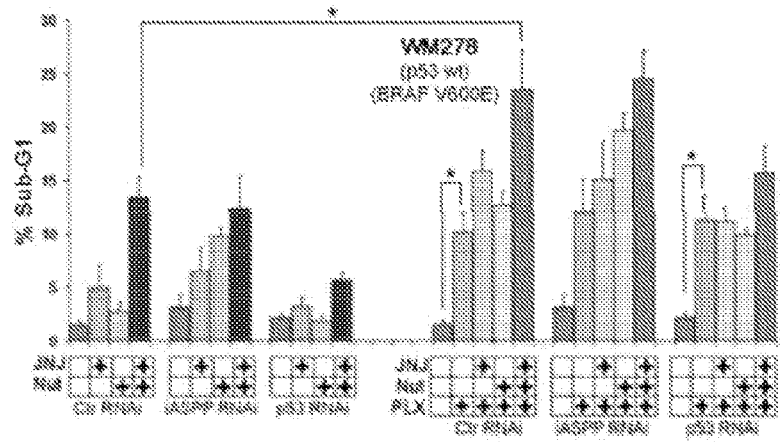
FIG. 22B. WM278 cells were treated as described for FIG. 21A. From left to right, the bars correspond to DMSO, JNJ, Nut and JNJ+Nut, respectively. The bar shows the percentage of Sub-G1 cells.
Figure 22C:
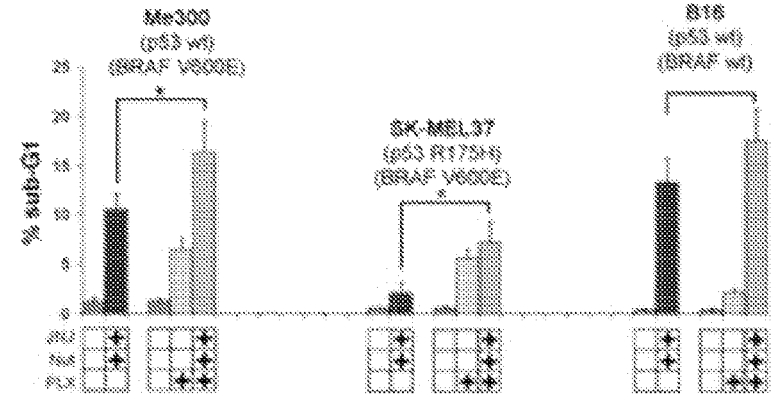
FIG. 22C. The bar graphs (mean±SD) were derived from three independent experiments. *p<0.05. C. Me300, SK-MEL37, and B16 cells were treated as described herein and sub-G1 cells were analyzed as described herein.

WM278, Me300 and SK-MEL37 express BRAFV600E, whereas B16 express wild type BRAF. Experiments were carried out to examine whether restoring wild type p53 function and concurrently inhibiting BRAFV600E shows cooperative effects. WM278, Me300, and SK-MEL37 cells were first treated with increasing amounts of PLX4032. One µM PLX4032 was identified as the optimal concentration to induce apoptosis in these cells (FIG. 22A). PLX4032 alone was able to induce apoptosis and growth suppression in WM278, Me300 and SK-MEL37 cells, regardless of their p53 status, but had minimal effect in B16 cells (FIG. 21A, FIGS. 22B and C). Highest levels of apoptosis and growth suppression were observed in WM278 and Me300 cells when JNJ, Nutlin3 and PLX4032 were used together. Restoring the apoptotic function of p53 together with BRAFV600E inhibition can achieve additive effects in suppressing melanoma growth. In some aspects, targeting two independent pathways represents a new strategy for the treatment of melanoma.

The invention has been described in terms of particular embodiments found or proposed to comprise specific modes for the practice of the invention. Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

Avery-Kiejda, K. A., Bowden, N. A., Croft, A. J., Scurr, L. L., Kairupan, C. F., Ashton, K. A., Talseth-Palmer, B. A., Rizos, H., Zhang, X. D., Scott, R. J., et al. (2011). P53 in human melanoma fails to regulate target genes associated with apoptosis and the cell cycle and may contribute to proliferation. BMC cancer 11, 203.

Batycka, M., Inglis, N. F., Cook, K., Adam, A., Fraser-Pitt, D., Smith, D. G., Main, L., Lubben, A., and Kessler, B. M. (2006). Ultra-fast tandem mass spectrometry scanning combined with monolithic column liquid chromatography increases throughput in proteomic analysis. Rapid Commun Mass Spectrom 20, 2074-2080.

Bergamaschi, D., Samuels, Y., O'Neil, N. J., Trigiante, G., Crook, T., Hsieh, J. K., O'Connor, D. J., Zhong, S., Campargue, I., Tomlinson, M. L., et al. (2003). iASPP oncoprotein is a key inhibitor of p53 conserved from worm to human. Nature genetics 33, 162-167.

Chapman, P. B., Hauschild, A., Robert, C., Haanen, J. B., Ascierto, P., Larkin, J., Dummer, R., Garbe, C., Testori, A., Maio, M., et al. (2011). Improved survival with vemurafenib in melanoma with BRAF V600E mutation. The New England journal of medicine 364, 2507-2516.

Cox, A. D., and Der, C. J. (2012). The RAF Inhibitor Paradox Revisited. Cancer cell 21, 147-149.

Curtin, J. A., Fridlyand, J., Kageshita, T., Patel, H. N., Busam, K. J., Kutzner, H., Cho, K. H., Aiba, S., Brocker, E. B., LeBoit, P. E., et al. (2005). Distinct sets of genetic alterations in melanoma. The New England journal of medicine 353, 2135-2147.

de Lange, J., Ly, L. V., Lodder, K., Verlaan-de Vries, M., Teunisse, A. F., Jager, M. J., and Jochemsen, A. G. (2011). Synergistic growth inhibition based on small-molecule p53 activation as treatment for intraocular melanoma. Oncogene.

Fedorov, O., Marsden, B., Pogacic, V., Rellos, P., Muller, S., Bullock, A. N., Schwaller, J., Sundstrom, M., and Knapp, S. (2007). A systematic interaction map of validated kinase inhibitors with Ser/Thr kinases. Proceedings of the National Academy of Sciences of the United States of America 104, 20523-20528.

Flaherty, K. T. (2011). Targeting Metastatic Melanoma. Annual review of medicine.

Forbes, S., Clements, J., Dawson, E., Bamford, S., Webb, T., Dogan, A., Flanagan, A., Teague, J., Wooster, R., Futreal, P. A., et al. (2006). Cosmic 2005. British journal of cancer 94, 318-322.

Georgieva, J., Sinha, P., and Schadendorf, D. (2001). Expression of cyclins and cyclin dependent kinases in human benign and malignant melanocytic lesions. Journal of clinical pathology 54, 229-235.

Houben, R., Hesbacher, S., Schmid, C. P., Kauczok, C. S., Flohr, U., Haferkamp, S., Muller, C. S., Schrama, D., Wischhusen, J., and Becker, J. C. (2011). High-level expression of wild-type p53 in melanoma cells is frequently associated with inactivity in p53 reporter gene assays. PLoS one 6, e22096.

Ji, Z., Njauw, C. N., Taylor, M., Neel, V., Flaherty, K. T., and Tsao, H. (2011). p53 Rescue through HDM2 Antagonism Suppresses Melanoma Growth and Potentiates MEK Inhibition. The Journal of investigative dermatology.

Johannessen, C. M., Boehm, J. S., Kim, S. Y., Thomas, S. R., Wardwell, L., Johnson, L. A., Emery, C. M., Stransky, N., Cogdill, A. P., Barretina, J., et al. (2010). COT drives resistance to RAF inhibition through MAP kinase pathway reactivation. Nature 468, 968-972.

Joseph, E. W., Pratilas, C. A., Poulikakos, P. I., Tadi, M., Wang, W., Taylor, B. S., Halilovic, E., Persaud, Y., Xing, F., Viale, A., et al. (2010). The RAF inhibitor PLX4032 inhibits ERK signaling and tumor cell proliferation in a V600E BRAF-selective manner. Proceedings of the National Academy of Sciences of the United States of America 107, 14903-14908.

Kamath, K. S., Vasavada, M. S., and Srivastava, S. (2011). Proteomic databases and tools to decipher post-translational modifications. Journal of proteomics 75, 127-144.

Muthusamy, V., Hobbs, C., Nogueira, C., Cordon-Cardo, C., McKee, P. H., Chin, L., and Bosenberg, M. W. (2006). Amplification of CDK4 and MDM2 in malignant melanoma. Genes, chromosomes & cancer 45, 447-454.

Nazarian, R., Shi, H., Wang, Q., Kong, X., Koya, R. C., Lee, H., Chen, Z., Lee, M. K., Attar, N., Sazegar, H., et al. (2010). Melanomas acquire resistance to B-RAF(V600E) inhibition by RTK or N-RAS upregulation. Nature 468, 973-977.

Notari, M., Hu, Y., Koch, S., Lu, M., Ratnayaka, I., Zhong, S., Baer, C., Pagotto, A., Goldin, R., Salter, V., et al. (2011). Inhibitor of apoptosis-stimulating protein of p53 (iASPP) prevents senescence and is required for epithelial stratification. Proceedings of the National Academy of Sciences of the United States of America 108, 16645-16650.

Polsky, D., Bastian, B. C., Hazan, C., Melzer, K., Pack, J., Houghton, A., Busam, K., Cordon-Cardo, C., and Osman, I. (2001). HDM2 protein overexpression, but not gene amplification, is related to tumorigenesis of cutaneous melanoma. Cancer research 61, 7642-7646.

Polsky, D., Melzer, K., Hazan, C., Panageas, K. S., Busam, K., Drobnjak, M., Kamino, H., Spira, J. G., Kopf, A. W., Houghton, A., et al. (2002). HDM2 protein overexpression and prognosis in primary malignant melanoma. Journal of the National Cancer Institute 94, 1803-1806.

Poulikakos, P. I., Persaud, Y., Janakiraman, M., Kong, X., Ng, C., Moriceau, G., Shi, H., Atefi, M., Titz, B., Gabay, M. T., et al. (2011). RAF inhibitor resistance is mediated by dimerization of aberrantly spliced BRAF(V600E). Nature 480, 387-390.

Poulikakos, P. I., and Rosen, N. (2011). Mutant BRAF melanomas—dependence and resistance. Cancer cell 19, 11-15.

Poulikakos, P. I., and Solit, D. B. (2011). Resistance to MEK inhibitors: should we co-target upstream? Science signaling 4, pe16.

Robinson, R. A., Lu, X., Jones, E. Y., and Siebold, C. (2008). Biochemical and structural studies of ASPP proteins reveal differential binding to p53, p63, and p73. Structure 16, 259-268.

Sachdev, S., Hoffmann, A., and Hannink, M. (1998). Nuclear localization of IkappaB alpha is mediated by the second ankyrin repeat: the IkappaB alpha ankyrin repeats define a novel class of cis-acting nuclear import sequences. Molecular and cellular biology 18, 2524-2534.

Samuels-Lev, Y., O'Connor, D. J., Bergamaschi, D., Trigiante, G., Hsieh, J. K., Zhong, S., Campargue, I., Naumovski, L., Crook, T., and Lu, X. (2001). ASPP proteins specifically stimulate the apoptotic function of p53. Molecular cell 8, 781-794.

Schittek, B., Psenner, K., Sauer, B., Meier, F., Iftner, T., and Garbe, C. (2007). The increased expression of Y box-binding protein 1 in melanoma stimulates proliferation and tumor invasion, antagonizes apoptosis and enhances chemoresistance. International journal of cancer 120, 2110-2118.

Slee, E. A., Gillotin, S., Bergamaschi, D., Royer, C., Llanos, S., Ali, S., Jin, B., Trigiante, G., and Lu, X. (2004). The N-terminus of a novel isoform of human iASPP is required for its cytoplasmic localization. Oncogene 23, 9007-9016.

Song, Y., Zhao, C., Dong, L., Fu, M., Xue, L., Huang, Z., Tong, T., Zhou, Z., Chen, A., Yang, Z., et al. (2008). Overexpression of cyclin B1 in human esophageal squamous cell carcinoma cells induces tumor cell invasive growth and metastasis. Carcinogenesis 29, 307-315.

Tseng, H. Y., Jiang, C. C., Croft, A., Tay, K. H., Thorne, R. F., Yang, F., Liu, H., Hersey, P., and Zhang, X. D. (2010). Contrasting effects of nutlin-3 on TRAIL- and docetaxel-induced apoptosis due to upregulation of TRAIL-R2 and Mcl-1 in human melanoma cells. Molecular cancer therapeutics 9, 3363-3374.

Van Impe, K., Hubert, T., De Corte, V., Vanloo, B., Boucherie, C., Vandekerckhove, J., and Gettemans, J. (2008). A new role for nuclear transport factor 2 and Ran: nuclear import of CapG. Traffic (Copenhagen, Denmark) 9, 695-707.

Yang, J. P., Hori, M., Sanda, T., and Okamoto, T. (1999). Identification of a novel inhibitor of nuclear factor-kappaB, RelA-associated inhibitor. The Journal of biological chemistry 274, 15662-15670.

What is claimed is:

1. A method of measuring inhibitory Apoptosis-Stimulating Protein of p53 (iASPP) phosphorylation in a cancer comprising:
   (a) contacting a cancer cell from a human subject, or protein from the cancer cell, with an antibody, or antigen-binding fragment of the antibody, that binds iASPP and that differentially binds iASPP that has been phosphorylated at an iASPP serine residue corresponding to serine 113 (Ser113) in the human iASPP amino acid sequence of SEQ ID NO: 2, compared to iASPP unphosphorylated at said iASPP serine residue;
   (b) measuring the amount of complex formed between the binding partner and the iASPP.

2. The method of claim 1, wherein the antibody, or antigen-binding fragment thereof, comprises a detectable label.

3. The method according to claim 1, wherein the contacting is performed in situ in a tumor biopsy.

4. The method according to claim 1, wherein the antibody, or antigen-binding fragment thereof, binds to an epitope comprising all or some of amino acids 107-118 of SEQ ID NO: 2.

5. The method according to claim 1, wherein (a) comprises contacting the cancer cell from a human subject, or the protein from the cancer cell, with an antibody, or antigen-binding fragment of the antibody, that preferentially binds iASPP that has been phosphorylated at the iASPP serine residue corresponding to Ser113 in the human iASPP amino acid sequence of SEQ ID NO: 2.

6. The method according to claim 5, wherein the antibody, or antigen-binding fragment thereof, binds an epitope of iASPP that includes the iASPP serine residue corresponding to Ser113 in the human iASPP amino acid sequence of SEQ ID NO: 2 and selectively binds iASPP when said serine in said epitope is phosphorylated.

7. The method according to claim 5, wherein (b) comprises quantifying the amount of phosphorylated iASPP from the measurement of the complex.

8. The method according to claim 7, further comprising measuring total iASPP in the cell, wherein the measures of phosphorylated iASPP and total iASPP provide an indication of the phosphorylation state of iASPP in the cell.

9. The method according to claim 1, wherein (a) comprises contacting the cancer cell from a human subject, or the protein from the cancer cell, with an antibody, or antigen-binding fragment of the antibody, that preferentially binds iASPP that is unphosphorylated at the iASPP serine residue corresponding to Ser113 in the human iASPP amino acid sequence of SEQ ID NO: 2.

10. The method according to claim 9, wherein the antibody, or antigen-binding fragment thereof, binds an epitope of iASPP that includes the iASPP serine residue corresponding to Ser113 in the human iASPP amino acid sequence of SEQ ID NO: 2 and selectively binds iASPP when said serine in said epitope is unphosphorylated.

11. The method according to claim 9 that comprises measuring total iASPP in the cell, and measuring unphosphorylated iASPP in the cell, wherein a difference between total iASPP and unphosphorylated iASPP provides an indication of the amount of phosphorylated iASPP in the cell.

12. The method of claim 1, further comprising:
   screening the cancer cell for at least one parameter selected from the group consisting of: a p53 mutation that reduces a tumor suppressive function of p53, an elevated measurement of mdm2 protein or mRNA, and a B-RafV600E mutation.

13. A method of measuring inhibitory Apoptosis-Stimulating Protein of p53 (iASPP) phosphorylation in a cancer comprising:
   (a) contacting a cancer cell from a human subject, or protein from the cancer cell, with an antibody, or antigen-binding fragment of the antibody, that binds iASPP and that differentially binds iASPP that has been phosphorylated at an iASPP serine residue corresponding to serine 113 (Ser113) in the human iASPP amino acid sequence of SEQ ID NO: 2, compared to iASPP unphosphorylated at said iASPP serine residue;
   (b) measuring the amount of complex formed between the binding partner and the iASPP; and
   (c) measuring total iASPP in the cancer cell or the protein from the cancer cell.

14. The method according to claim 13, wherein the measuring of total iASPP comprises contacting the cancer cell, or the protein from the cancer cell, with an antibody that binds to an epitope comprising all or some of amino acids 501-510 of SEQ ID NO: 2.

15. The method according to claim 13, further comprising
   (d) comparing the measurements of (b) and (c) to determine a relative measure of the fraction of iASPP that is phosphorylated, or the fraction that is unphosphorylated, at said iASPP serine residue.

16. The method according to claim 15, wherein the cancer cell is from a primary tumor from the subject, and the method further comprises:
(e) diagnosing metastatic potential of the cancer based on the phosphorylation state of the iASPP in the cancer cell measured.

17. The method of claim 16, comprising measuring phosphorylation of iASPP in a plurality of cancer cells from a primary tumor from the human subject, and diagnosing metastatic potential of the cancer based on an average measurement from the plurality of the cells, or from a percentage of the cells that exceed a cutoff or reference measurement.

18. The method of claim 16, further comprising diagnosing metastatic potential of the cancer from the percentage of total iASPP that is phosphorylated in the cancer cell.

19. The method according to claim 16, wherein the diagnosing comprises comparing the amount of phosphorylated iASPP in the cancer cell with a measurement of phosphorylated iASPP from healthy cells of the same type as the cancer cell, wherein increased iASPP phosphorylation in the cancer cell indicates that the cancer is at increased risk for metastases.

20. The method of claim 16, further comprising:
screening the cancer cell for at least one parameter selected from the group consisting of: a p53 mutation that reduces a tumor suppressive function of p53, an elevated measurement of mdm2 protein or mRNA, and a B-RafV600E mutation; and
diagnosing metastatic potential of the cancer based on the phosphorylation state of iASPP in the cancer cell and from the presence or absence of the at least one parameter.

21. The method according to claim 16, wherein the cancer cell is from a cancer selected from the group consisting of melanoma, prostate cancer and head and neck cancer.

22. The method according to claim 16, further comprising:
identifying elevated metastatic potential for the cancer based on the phosphorylation state of iASPP, and
administering a therapeutic regimen that includes an inhibitor of iASPP phosphorylation.

23. A therapeutic regimen for treating a cancer in a human subject, the method comprising:
(a) measuring phosphorylation state of iASPP according to claim 1,
(b) screening the cancer cell for at least one parameter selected from the group consisting of: a p53 mutation that reduces a tumor suppressive function of p53, an elevated measurement of mdm2 protein or mRNA, and a B-RafV600E mutation; and
(c) for a subject with a cancer characterized by elevated iASPP phosphorylation, prescribing and/or administering a therapeutic regimen that includes an inhibitor of iASPP phosphorylation.

24. The therapeutic regimen according to claim 23, wherein the cancer is selected from melanoma, prostate cancer and head and neck cancer.

25. The therapeutic regimen of claim 23 that comprises:
prescribing and/or administering a therapeutic regimen that includes an inhibitor of iASPP phosphorylation and an inhibitor of mdm2-induced degradation of p53, for a subject with a cancer characterized by elevated iASPP phosphorylation and the absence of a p53 mutation that reduces the tumor suppressive function of p53.

26. The therapeutic regimen of claim 25, wherein the inhibitor of mdm2-induced degradation of p53 is Nutlin3.

27. The therapeutic regimen of claim 23 that comprises:
prescribing and/or administering a therapeutic regimen that includes an inhibitor of iASPP phosphorylation and an inhibitor B-RafV600E, for a subject with a cancer characterized by elevated iASPP phosphorylation and the presence of the B-Raf-V600E mutation.

28. The therapeutic regimen of claim 27, wherein the inhibitor of B-RafV600E is Vemurafenib.

29. The therapeutic regimen of claim 23, wherein the inhibitor if iASPP phosphorylation is an inhibitor of cyclin B1/cdk1.

30. The therapeutic regimen of claim 29, wherein the inhibitor of cyclin B1/cdk1 is JNJ-7706621.

31. A method comprising:
(a) measuring the intracellular localization of inhibitory Apoptosis-Stimulating protein of p53 (iASPP) in a cancer cell from a human subject;
(b) detecting elevated levels of iASPP in the nucleus of the cancer cell;
(c) identifying elevated metastatic potential for the cancer based on the elevated levels of iASPP in the nucleus of the cell; and
(d) prescribing and/or administering to the subject a therapeutic regimen that includes an inhibitor of iASPP phosphorylation.

32. The method of claim 31, wherein (d) comprises administering to the subject a therapeutic regimen that includes an inhibitor of iASPP phosphorylation.

33. The method according to claim 32, further comprising:
screening the cancer cell for at least one parameter selected from the group consisting of: a p53 mutation that reduces a tumor suppressive function of p53, an elevated measurement of mdm2 protein or mRNA, and a B-RafV600E mutation; and
administering to the subject a therapeutic regimen that includes an inhibitor of mdm2-induced degradation of p53, for a subject with a cancer characterized by the absence of a p53 mutation that reduces the tumor suppressive function of p53 or an elevated measurement of mdm2 protein or mRNA; and/or prescribing and/or administering a therapeutic regimen that includes an inhibitor B-RafV600E, for a subject with a cancer characterized by the presence of the B-Raf-V600E mutation.

34. A method of treating a mammalian subject with cancer, the method comprising:
administering to the subject an inhibitor of cyclin B1/cdk1-induced phosphorylation of iASPP; an inhibitor of mdm2-induced degradation of p53; and an inhibitor B-RafV600E; wherein the cancer comprises cancer cells having a wild-type p53 free of p53 mutations that reduce the tumor suppressor functions of p53, elevated levels of MDM2, and B-Raf having a V600Emutation; and wherein the inhibitors are administered in amounts effective to inhibit proliferation or induce cell death in the cancer.

35. The method according to claim 34, wherein the cancer is selected from melanoma, prostate cancer and head and neck cancer.

36. An iASPP binding partner selected from the group consisting of:
(a) antibody that specifically binds iASPP polypeptide and preferentially binds to iASPP having a phosphorylated serine compared to binding to iASPP without the phosphorylated serine, wherein said serine residue corresponds to Ser113 of the human iASPP amino acid sequence of SEQ ID NO: 2;
(b) a fragment of (a) that specifically binds iASPP polypeptide and preferentially binds to iASPP having the phosphorylated serine; and
(c) a polypeptide that comprises (b) and that specifically binds iASPP polypeptide and preferentially binds to iASPP having the phosphorylated serine.

37. The iASPP binding partner of claim 36 that binds to an epitope of the phosphorylated peptide comprising a portion of amino acids 81-130 of SEQ ID NO: 2, wherein the serine at position 113 of SEQ ID NO: 2 is phosphorylated.

38. The iASPP binding partner of claim 36 that binds to an epitope of the phosphorylated peptide comprising at least a portion of amino acids 107-118 of SEQ ID NO: 2, wherein the serine at position 113 of SEQ ID NO: 2 is phosphorylated.

39. The iASPP binding partner of claim 36 that is a monoclonal antibody.

40. The iASPP binding partner of claim 36, wherein the antibody or antigen binding fragment does not bind to unphosphorylated iASPP.

41. The iASPP binding partner of claim 40 that comprises an antigen binding fragment of the antibody.

42. The iASPP binding partner of claim 41 that comprises a Fab, Fab', F(ab')$_2$, Fv or an ScFv antibody.

43. A hybridoma cell line that produces the antibody of claim 39.

44. A kit comprising
a first antibody that differentially recognizes an iASPP polypeptide having a phosphorylated serine residue at a serine residue corresponding to serine 113 (Ser113) in the human iASPP amino acid sequence of SEQ ID NO: 2, compared to iASPP unphosphorylated at said iASPP serine residue; and
a second antibody that binds to iASPP at an epitope distinct from that recognized by the first antibody, wherein the second antibody binds both phosphorylated and unphosphorylated iASPP.

45. The kit of claim 44, wherein the first antibody binds to an epitope comprising amino acids 107-118 of SEQ ID NO: 2, wherein the serine at position 113 of SEQ ID NO: 2 is phosphorylated.

* * * * *

SEQUENCE LISTING

<160> NUMBER OF SEQ ID NOS: 15

<210> SEQ ID NO 1
<211> LENGTH: 2487
<212> TYPE: DNA
<213> ORGANISM: Homo sapiens

<400> SEQUENCE: 1

| | | | | | | |
|---|---|---|---|---|---|---|
| atggacagcg | aggcattcca | gagcgcgcgg | gactttctgg | acatgaactt | ccagtcgctg | 60 |
| gccatgaaac | acatggatct | gaagcagatg | gagctggaca | cggcggcggc | caaggtggat | 120 |
| gaactgacca | agcagctgga | gtcgctgtgg | tcagactctc | ccgcgcctcc | tggcccgcag | 180 |
| gccggacccc | cttctaggcc | gccccggtac | agctccagct | cgatccctga | gcccttcggc | 240 |
| agccgagggt | cccccggaa | ggcggccacc | gacggcgcag | acacccgtt | cggacgatca | 300 |
| gagagtgccc | caaccctaca | cccctacagc | ccgctgtccc | ccaagggacg | gccgtcgtcg | 360 |
| ccgcgcaccc | cgctctacct | gcagccggac | gcctacggca | gcctggaccg | cgcgacctcg | 420 |
| ccccggcccc | gcgccttcga | tggcgcaggc | agctccctcg | gccgtgcgcc | ctccccgcgg | 480 |
| cccgggccag | gcccgctccg | ccagcagggt | cccccacgc | ctttcgactt | cctgggccgc | 540 |
| gcaggctccc | cccgcggcag | ccccctggcg | gaggggcccc | aggccttctt | ccccgagcgt | 600 |
| gggccgtcac | cgcgccccc | tgccacagcc | tacgacgcgc | cagcgtccgc | cttcgggagc | 660 |
| tccctgctag | gctccggcgg | cagcgcattc | gccccgcctc | tgcgcgcgca | agacgacctg | 720 |
| acgctgcgcc | ggcggcctcc | gaaagcctgg | aacgagtctg | acctggacgt | ggcgtacgag | 780 |
| aagaagcctt | cgcagacagc | gagctatgaa | cgcctggacg | tcttcgcaag | gcctgcctcg | 840 |
| ccgagcctgc | agctgttgcc | ttgagggag | agcagcctgg | atggactggg | gggcaccggc | 900 |
| aaggacaacc | tcactagcgc | caccctgccg | cgcaattaca | aggtctctcc | tctggccagc | 960 |
| gaccggcgtt | cagacgcggg | cagctaccgg | cgctcgctgg | gctccgcggg | gccgtcgggc | 1020 |
| actttgcctc | gcagctggca | gcccgtcagc | cgcatcccca | tgccccctc | cagccccag | 1080 |
| ccccgcgggg | ccccgcgcca | gcgtcccatc | cccctcagca | tgatcttcaa | gctgcagaac | 1140 |
| gccttctggg | agcacggggc | cagccgcgcc | atgctccctg | ggtccccct | cttcacccga | 1200 |
| gcaccccgc | ctaagctgca | gccccaacca | caaccacagc | cccagccaca | atcacaacca | 1260 |
| cagccccagc | tgccccaca | gccccagacc | caaccccaaa | ccctaccc | agcccccag | 1320 |
| catccccaac | agacatggcc | cctgtgaac | gaaggacccc | ccaaaccccc | caccgagctg | 1380 |
| gagcctgagc | cggagataga | ggggctgctg | acaccagtgc | tggaggctgg | cgatgtggat | 1440 |
| gaaggccctg | tagcaaggcc | tctcagcccc | acgaggctgc | agccagcact | gccaccggag | 1500 |
| gcacagtcgg | tgcccgagct | ggaggaggtg | gcacgggtgt | tggcggaaat | tccccggccc | 1560 |
| ctcaaacgca | ggggctccat | ggagcaggcc | cctgctgtgg | ccctgccccc | tacccacaag | 1620 |
| aaacagtacc | agcagatcat | cagccgcctc | ttccatcgtc | atgggggcc | agggcccggg | 1680 |
| gggccggagc | cagagctgtc | ccccatcact | gagggatctg | aggccagggc | agggcccct | 1740 |
| gctcctgccc | caccagctcc | cattccaccc | ccggcccgt | cccagagcag | cccaccagag | 1800 |
| cagccgcaga | gcatggagat | gcgctctgtg | ctgcggaagg | cgggctcccc | gcgcaaggcc | 1860 |
| cgccgcgcgc | gcctcaaccc | tctggtgctc | ctcctggacg | cggcgctgac | cggggagctg | 1920 |
| gaggtggtgc | agcaggcggt | gaaggagatg | aacgacccga | gccagcccaa | cgaggagggc | 1980 |

-continued

```
atcactgcct tgcacaacgc catctgcggc gccaactact ctatcgtgga tttcctcatc    2040
accgcgggtg ccaatgtcaa ctcccccgac agccacggct ggacacccct tgcactgcgcg   2100 gcgtcgtgca acgacacagt catctgcatg gcgctggtgc agcacggcgc tgcaatcttc    2160
gccaccacgc tcagcgacgg cgccaccgcc ttcgagaagt gcgaccctta ccgcgagggt    2220
tatgctgact gcgccaccta cctggcagac gtcgagcaga gtatgggggct gatgaacagc    2280 ggggcagtgt acgctctctg ggactacagc gccgagttcg gggacgagct gtccttccgc    2340
gagggcgagt cggtcaccgt gctgcggagg gacgggccgg aggagaccga ctggtggtgg   2400
gccgcgctgc acggccagga gggctacgtg ccgcggaact acttcgggct gttccccagg    2460
gtgaagcctc aaaggagtaa agtctag                                        2487
```

<210> SEQ ID NO 2
<211> LENGTH: 828
<212> TYPE: PRT
<213> ORGANISM: Homo sapiens

<400> SEQUENCE: 2

```
Met Asp Ser Glu Ala Phe Gln Ser Ala Arg Asp Phe Leu Asp Met Asn
1               5                   10                  15

Phe Gln Ser Leu Ala Met Lys His Met Asp Leu Lys Gln Met Glu Leu
            20                  25                  30

Asp Thr Ala Ala Ala Lys Val Asp Glu Leu Thr Lys Gln Leu Glu Ser
        35                  40                  45

Leu Trp Ser Asp Ser Pro Ala Pro Pro Gly Pro Gln Ala Gly Pro Pro
    50                  55                  60

Ser Arg Pro Pro Arg Tyr Ser Ser Ser Ile Pro Glu Pro Phe Gly
65                  70                  75                  80

Ser Arg Gly Ser Pro Arg Lys Ala Ala Thr Asp Gly Ala Asp Thr Pro
                85                  90                  95

Phe Gly Arg Ser Glu Ser Ala Pro Thr Leu His Pro Tyr Ser Pro Leu
            100                 105                 110

Ser Pro Lys Gly Arg Pro Ser Ser Pro Arg Thr Pro Leu Tyr Leu Gln
        115                 120                 125

Pro Asp Ala Tyr Gly Ser Leu Asp Arg Ala Thr Ser Pro Arg Pro Arg
    130                 135                 140

Ala Phe Asp Gly Ala Gly Ser Ser Leu Gly Arg Ala Pro Ser Pro Arg
145                 150                 155                 160

Pro Gly Pro Gly Pro Leu Arg Gln Gln Gly Pro Pro Thr Pro Phe Asp
                165                 170                 175

Phe Leu Gly Arg Ala Gly Ser Pro Arg Gly Ser Pro Leu Ala Glu Gly
            180                 185                 190

Pro Gln Ala Phe Phe Pro Glu Arg Gly Pro Ser Pro Pro Ala
        195                 200                 205

Thr Ala Tyr Asp Ala Pro Ala Ser Ala Phe Gly Ser Ser Leu Leu Gly
    210                 215                 220

Ser Gly Gly Ser Ala Phe Ala Pro Pro Leu Arg Ala Gln Asp Asp Leu
225                 230                 235                 240

Thr Leu Arg Arg Arg Pro Pro Lys Ala Trp Asn Glu Ser Asp Leu Asp
                245                 250                 255

Val Ala Tyr Glu Lys Lys Pro Ser Gln Thr Ala Ser Tyr Glu Arg Leu
            260                 265                 270

Asp Val Phe Ala Arg Pro Ala Ser Pro Ser Leu Gln Leu Leu Pro Trp
        275                 280                 285
```

```
Arg Glu Ser Ser Leu Asp Gly Leu Gly Gly Thr Gly Lys Asp Asn Leu
    290                 295                 300
Thr Ser Ala Thr Leu Pro Arg Asn Tyr Lys Val Ser Pro Leu Ala Ser
305                 310                 315                 320
Asp Arg Arg Ser Asp Ala Gly Ser Tyr Arg Arg Ser Leu Gly Ser Ala
                325                 330                 335
Gly Pro Ser Gly Thr Leu Pro Arg Ser Trp Gln Pro Val Ser Arg Ile
            340                 345                 350
Pro Met Pro Ser Ser Pro Gln Pro Arg Gly Ala Pro Arg Gln Arg
            355                 360                 365
Pro Ile Pro Leu Ser Met Ile Phe Lys Leu Asn Ala Phe Trp Glu
370                 375                 380
His Gly Ala Ser Arg Ala Met Leu Pro Gly Ser Pro Leu Phe Thr Arg
385                 390                 395                 400
Ala Pro Pro Pro Lys Leu Gln Pro Gln Pro Gln Pro Gln Pro
                405                 410                 415
Gln Ser Gln Pro Gln Pro Gln Leu Pro Pro Gln Pro Gln Thr Gln Pro
            420                 425                 430
Gln Thr Pro Thr Pro Ala Pro Gln His Pro Gln Thr Trp Pro Pro
            435                 440                 445
Val Asn Glu Gly Pro Pro Lys Pro Pro Thr Glu Leu Glu Pro Glu Pro
450                 455                 460
Glu Ile Glu Gly Leu Leu Thr Pro Val Leu Glu Ala Gly Asp Val Asp
465                 470                 475                 480
Glu Gly Pro Val Ala Arg Pro Leu Ser Pro Thr Arg Leu Gln Pro Ala
                485                 490                 495
Leu Pro Pro Glu Ala Gln Ser Val Pro Glu Leu Glu Val Ala Arg
            500                 505                 510
Val Leu Ala Glu Ile Pro Arg Pro Leu Lys Arg Arg Gly Ser Met Glu
            515                 520                 525
Gln Ala Pro Ala Val Ala Leu Pro Pro Thr His Lys Lys Gln Tyr Gln
530                 535                 540
Gln Ile Ile Ser Arg Leu Phe His Arg His Gly Gly Pro Gly Pro Gly
545                 550                 555                 560
Gly Pro Glu Pro Glu Leu Ser Pro Ile Thr Glu Gly Ser Glu Ala Arg
                565                 570                 575
Ala Gly Pro Pro Ala Pro Ala Pro Ala Pro Ile Pro Pro Ala
            580                 585                 590
Pro Ser Gln Ser Ser Pro Pro Glu Gln Pro Gln Ser Met Glu Met Arg
            595                 600                 605
Ser Val Leu Arg Lys Ala Gly Ser Pro Arg Lys Ala Arg Arg Ala Arg
            610                 615                 620
Leu Asn Pro Leu Val Leu Leu Asp Ala Ala Leu Thr Gly Glu Leu
625                 630                 635                 640
Glu Val Val Gln Gln Ala Val Lys Glu Met Asn Asp Pro Ser Gln Pro
                645                 650                 655
Asn Glu Glu Gly Ile Thr Ala Leu His Asn Ala Ile Cys Gly Ala Asn
            660                 665                 670
Tyr Ser Ile Val Asp Phe Leu Ile Thr Ala Gly Ala Asn Val Asn Ser
            675                 680                 685
Pro Asp Ser His Gly Trp Thr Pro Leu His Cys Ala Ala Ser Cys Asn
            690                 695                 700
```

```
Asp Thr Val Ile Cys Met Ala Leu Val Gln His Gly Ala Ala Ile Phe
705                 710                 715                 720

Ala Thr Thr Leu Ser Asp Gly Thr Ala Phe Glu Lys Cys Asp Pro
                725                 730                 735

Tyr Arg Glu Gly Tyr Ala Asp Cys Ala Thr Tyr Leu Ala Asp Val Glu
            740                 745                 750

Gln Ser Met Gly Leu Met Asn Ser Gly Ala Val Tyr Ala Leu Trp Asp
        755                 760                 765

Tyr Ser Ala Glu Phe Gly Asp Glu Leu Ser Phe Arg Glu Gly Glu Ser
        770                 775                 780

Val Thr Val Leu Arg Arg Asp Gly Pro Glu Glu Thr Asp Trp Trp Trp
785                 790                 795                 800

Ala Ala Leu His Gly Gln Glu Gly Tyr Val Pro Arg Asn Tyr Phe Gly
                805                 810                 815

Leu Phe Pro Arg Val Lys Pro Gln Arg Ser Lys Val
            820                 825

<210> SEQ ID NO 3
<211> LENGTH: 18
<212> TYPE: DNA
<213> ORGANISM: Artificial Sequence
<220> FEATURE:
<223> OTHER INFORMATION: Synthetic primer

<400> SEQUENCE: 3
cggggacact ttgcgttc                                                 18

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
ttctgacgca cacctattgc                                               20

<210> SEQ ID NO 5
<211> LENGTH: 18
<212> TYPE: DNA
<213> ORGANISM: Artificial Sequence
<220> FEATURE:
<223> OTHER INFORMATION: Synthetic primer

<400> SEQUENCE: 5
gctttccacg acggtgag                                                 18

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
caagggttca aagacccaaa                                               20

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (10)..(10)
<223> OTHER INFORMATION: Xaa can be any naturally occurring amino acid

<400> SEQUENCE: 7

Gln Glu Thr Phe Ser Asp Leu Trp Lys Xaa Leu Pro
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide

<400> SEQUENCE: 8

Met Pro Arg Phe Met Asp Tyr Trp Glu Gly Leu Asn
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Phe Met Asp Tyr Trp Glu Gly Leu Asn
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: Xaa is alpha-aminoisobutyric acid
<220> FEATURE:
<221> NAME/KEY: MOD_RES
<222> LOCATION: (6)..(6)
<223> OTHER INFORMATION: Xaa is alpha-aminoisobutyric acid
<220> FEATURE:
<221> NAME/KEY: MOD_RES
<222> LOCATION: (9)..(9)
<223> OTHER INFORMATION: Xaa is alpha-aminoisobutyric acid
<220> FEATURE:
<221> NAME/KEY: MOD_RES
<222> LOCATION: (11)..(11)
<223> OTHER INFORMATION: Xaa is alpha-aminoisobutyric acid

<400> SEQUENCE: 10

Glu Thr Phe Xaa Asp Xaa Trp Lys Xaa Leu Xaa Glu
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is alpha-aminoisobutyric acid
```

```
<220> FEATURE:
<221> NAME/KEY: MOD_RES
<222> LOCATION: (7)..(7)
<223> OTHER INFORMATION: Xaa is 1-aminocyclopropanecarboxylic acid

<400> SEQUENCE: 11

Phe Met Xaa Tyr Trp Glu Xaa Leu Asn
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is alpha-aminoisobutyric acid
<220> FEATURE:
<221> NAME/KEY: MOD_RES
<222> LOCATION: (4)..(4)
<223> OTHER INFORMATION: Xaa is phosphonomethylphenylalanine
<220> FEATURE:
<221> NAME/KEY: MOD_RES
<222> LOCATION: (7)..(7)
<223> OTHER INFORMATION: Xaa is 1-aminocyclopropanecarboxylic acid

<400> SEQUENCE: 12

Phe Met Xaa Xaa Trp Glu Xaa Leu Asn
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is alpha-aminoisobutyric acid
<220> FEATURE:
<221> NAME/KEY: MOD_RES
<222> LOCATION: (4)..(4)
<223> OTHER INFORMATION: Xaa is phosphonomethylphenylalanine
<220> FEATURE:
<221> NAME/KEY: MOD_RES
<222> LOCATION: (5)..(5)
<223> OTHER INFORMATION: Xaa is 6-chloro-tryptophan
<220> FEATURE:
<221> NAME/KEY: MOD_RES
<222> LOCATION: (7)..(7)
<223> OTHER INFORMATION: Xaa is 1-aminocyclopropanecarboxylic acid

<400> SEQUENCE: 13

Phe Met Xaa Xaa Xaa Glu Xaa Leu Asn
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: PHOSPHORYLATION
```

```
<400> SEQUENCE: 14

His Pro Tyr Ser Pro Leu Ser Pro Lys Gly Arg Pro Ser
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: PHOSPHORYLATION

<400> SEQUENCE: 15

Pro Glu Pro Phe Gly Ser Arg Gly Ser Pro Arg Lys Ala Ala Thr
1               5                   10                  15
```